United States Patent [19]
Bard et al.

[11] Patent Number: 5,861,309
[45] Date of Patent: Jan. 19, 1999

[54] DNA ENDODING HUMAN ALPHA 1 ADRENERGIC RECEPTORS

[75] Inventors: Jonathan A. Bard, Wyckoff, N.J.; Richard L. Weinshank, New York, N.Y.; Carlos Forray, Paramus, N.J.

[73] Assignee: Synaptic Pharmaceutical Corporation, Paramus, N.J.

[21] Appl. No.: 406,855

[22] PCT Filed: Sep. 24, 1993

[86] PCT No.: PCT/US93/09187

§ 371 Date: Aug. 21, 1995

§ 102(e) Date: Aug. 21, 1995

[87] PCT Pub. No.: WO94/08040

PCT Pub. Date: Apr. 14, 1994

Related U.S. Application Data

[63] Continuation-in-part of Ser. No. 952,798, Sep. 25, 1992, abandoned.

[51] Int. Cl.$^6$ ............................. C12N 15/85; C07H 21/04
[52] U.S. Cl. .................... 135/325; 435/69.1; 435/172.3; 435/320.1; 536/23.1; 536/23.5
[58] Field of Search ................................. 536/23.1, 23.5; 435/320.1, 325, 69.1, 172.3

[56] References Cited

U.S. PATENT DOCUMENTS

| | | | |
|---|---|---|---|
| 4,616,017 | 10/1986 | Baldwin | 514/452 |
| 4,661,491 | 4/1987 | Regnier | 435/172.3 |
| 4,873,191 | 10/1989 | Wagner | 514/260 |
| 5,155,128 | 10/1992 | Weinshank | 514/252 |

OTHER PUBLICATIONS

Schwinn et al., Molecular cloning and expression of the cDNA for a novel alpha 1–adrenergic receptor subtype, J. Biol. Chem., vol. 265(14), pp. 8183–8189, May 1990.
Bruno et al., Molecular cloning and sequencing of a cDNA encoding a human alpha 1a adrenergic receptor, Biochem. Biophys. Res. Comm., vol. 179(3), pp. 1485–1490, Sep. 1991.
Cotecchia et al., Molecular cloning and expression of the cDNA for the hamster alpha 1–adrenergic receptor, Proc. Natl. Acad. Sci., vol. 85, pp. 7159–7163, Oct. 1988.
Lerner, R.A., Nature 1982 299:592–596.
Glover, D.M., Gene Cloning, Chapman & Hall, London 1984, pp. 1–20.
DiBona, G.F., FASEB 1989 3:1993–1994.
Yakubov, L.A., et al., Proc. Natl. Acad. Sci. USA 1989 86:6454–6458.
Cotton, M. and Birnstiel, M.L., EMBO J. 1989 8 (12):3861–3866.
Waspe, L.E. et al., J. Clin. Invest. 1990 85(4):1206–1214.
Voight, M.M., et al., Nucleic Acids. Res. 1990 18(4):1053.
Lomasney, L.W. et al., J. Biol. Chem. 266 (10):6365–6369.
Wagner, E. et al., Proc. Natl. Acad. Sci. USA 1991 88:4255–4259.
Bruno, J.F. et al., Biochem. Biophys. Res. Com. 1991 179(3):1485–1490.
Roemer, K. and Friedman T., Eur. J. Biochem. 1992 208:211–225.
Karson, E.M., et al., J. Reproduct. Med. 1992 37(6):508–514.
Schwinn, D.A., and Lomasney, J.W., Eur. J. Pharmacol. 1992 227(4):433–436.
Link, R., et al., Molec. Pharmacol. 1992 42:;16–27.
Adham, N., et al., *Proc. Natl. Acad. Sci* . USA 1993 90: 408–412.
Forray, C., et al., *Molecular Pharmacol.* 1994 45: 703–708.
Gao, et al., *Gene* 1993 131: 243–247.
Jones, C.R., et al., *Progress In Brain Research* 1991 88: 271–291.
Laz, T.M., et al., *Molecular Pharmacol.* 1994 46: 414–422.
Perala, M., et al., *Molecular Brain Research* 1992 16: 57–63.
Weinshank, R.L., et al., *Proc. Natl. Acad. Sci.* USA 1992 89: 3630–3634; and.
Yang–Feng, T.L., et al., *Proc. Natl. Acad. Sci.* USA 1990 87: 1516–1520.

*Primary Examiner*—John L. LeGuyader
*Assistant Examiner*—Andrew Wang
*Attorney, Agent, or Firm*—John P. White; Cooper & Dunham LLP

[57] ABSTRACT

This invention provides an isolated nucleic acid, vectors, transformed mammalian cells and non-human transgenic animals that encode and express normal or mutant alpha 1*a*, alpha 1*b* and alpha 1*c* adrenergic receptor genes. This invention also provides a protein, and an antibody directed to the protein and pharmaceutical compounds related to alpha 1*a*, alpha 1*b* and alpha 1*c* adrenergic receptors. This invention provides nucleic acid probes, and antisense oligonucleotides complementary to alpha 1*a*, alpha 1*b* and alpha 1*c* adrenergic receptor genes. This invention further provides methods for determining ligand binding, detecting expression, drug screening, and treatments for alleviating abnormalities associated with human alpha 1*a*, alpha 1*b* and alpha 1*c* adrenergic receptors.

15 Claims, 37 Drawing Sheets

FIG. 1A

```
-176  CCGGGCCAGGCACGTCCGCTCTCGGACAGCCGCGTCCGCGTCACAGGAACTGGGCAGGAC  -117
           -170              -150              -130

-116  CCGACGGGACCCGTGCGGAGCTGCATCTGGAGCCCCGGCTATGCCCTGTGCTCCCC      -57
           -110              -90               -70

-56  TCCTGCCCGGCCCGTCGTTCTGTGCCCCCGGCCACCGACGGCCGCGTTGAGATG          3
 -18                                                      M         1
            -50               -30               -10

4  ACTTTCCGCGATCTCCTGAGCGTCAGTTTCGAGGACCCCGCCCGGACAGCAGCGGCAGGG  63
   2   T  F  R  D  L  L  S  V  S  F  E  G  P  R  P  D  D  S  S  A  G   21
             10                30                50
```

FIG. 1B

```
      70              90             110
64   GGCTCCAGCGCGGGGGCGGGGGCAGCGCGGGGCGCGCCCCTCGGAGGCCCG   123
22    G  S  S  A  G  G  G  G  G  S  A  G  G  A  A  P  S  E  G  P    41

130             150            170
124  GCGGTGGGCGGCGTGCCGGGCGGCGCGGGGGGCGGCGTGGTGGGCAGGCAGC  183
42    A  V  G  G  V  P  G  G  A  G  G  G  G  V  V  G  A  G  S    61

190             210            230
184  GGCGAGGACAACCGGAGCTCCGCGGGCGAGCCCGGCTCGGCCGGCGACGTG  243
62    G  E  D  N  R  S  S  A  G  E  P  G  S  A  G  D  V    81

250             270            290
244  AATGGCACGGCCGTCGGGGGACTGGTTGTGAGCGCGCAGGGCGTGGGCGTC  303
82    N  G  T  A  A  V  G  G  L  V  V  S  A  Q  G  V  G  V    101
```

FIG. 1C

```
304  TTCCTGGCAGCCTTCATCCTTATGGCCGTGGCAGGTAACCTGCTTGTCATCCTCTCAGTG  363
102   F  L  A  A  F  I  L  M  A  V  A  G  N  L  L  V  I  L  S  V   121

364  GCCTGCAACCGCCACCTGCAGACCGTCACCAACTATTTCATCGTGAACCTGGCCGTGGCC  423
122   A  C  N  R  H  L  Q  T  V  T  N  Y  F  I  V  N  L  A  V  A   141

424  GACCTGCTGCTGAGCGCCACCGTACTGCCCTTCTCGGCCACCATGGAGGTTCTGGGCTTC  483
142   D  L  L  L  S  A  T  V  L  P  F  S  A  T  M  E  V  L  G  F   161

484  TGGGCCTTTGGCCGCGCCTTCTGCGACGTATGGGCCGCCGTGGACGTCTGTGCTGCACG  543
162   W  A  F  G  R  A  F  C  D  V  W  A  A  V  D  V  L  C  C  T   181
```

FIG. 1D

```
544  GCCTCCATCCTCAGCCTCTGCACCATCTCCGTGGACCGGTACGTGGGCGTGCGCCACTCA  603
182  A  S  I  L  S  L  C  T  I  S  V  D  R  Y  V  G  V  R  H  S    201

604  CTCAAGTACCCAGCCATCATGACCGAGCGCAAGGCGGCCGCCATCCTGGCCCTGCTCTGG  663
202  L  K  Y  P  A  I  M  T  E  R  K  A  A  A  I  L  A  L  L  W    221

664  GTCGTAGCCCTGGTGGTCTCCGTAGGCCCCCTGCTGGGCTGGAAGGAGCCCGTGCCCCCT  723
222  V  V  A  L  V  V  S  V  G  P  L  L  G  W  K  E  P  V  P  P    241

724  GACGAGGCGCTTCTGCGGTATCACCGAGGAGGCGGGCTACGCTGTCTTCTCCTCCGTGTGC  783
242  D  E  R  F  C  G  I  T  E  E  A  G  Y  A  V  F  S  S  V  C    261
```

FIG. 1E

```
784  TCCTTCTACCTGCCCCATGGGCGGTGTCATCGTGGTGGTCATGTACTGCCGCGTGTACGTGGTGGTCGCG  843
262   S   F   Y   L   P   M   A   V   I   V   V   M   Y   C   R   V   Y   V   V   V   A    281

844  CGCAGCACCACCGGCCAGCCTCGAGGCGGTCAAGGCGAGGCAGGCAAGGCCTCCGAG                903
282   R   S   T   T   R   S   L   E   A   G   V   K   R   E   R   G   K   A   S   E        301

904  GTGGTGCTGCGCATCCACTGTCGCGGGGCCGCCACGGGGCCGACGGCGCACGGCATG                963
302   V   V   L   R   I   H   C   R   G   A   A   T   G   A   D   G   A   H   G   M        321

964  CGCAGCGCCAAGGGCCACACCTTCCGCAGCTCCTCCCTGTCCGTGCGCCTGCTCAAGTTCTCC         1023
322   R   S   A   K   G   H   T   F   R   S   S   L   S   V   R   L   L   K   F   S        341
```

FIG. 1F

```
1024  CGTGAGAAGAAAGCGGCCAAGACTCTGGCCATCGTCGTGGGTGTCTTCGTGCTCTGCTGG  1083
342   R   E   K   K   A   A   K   T   L   A   I   V   V   G   V   F   V   L   C   W    361

1084  TTCCCCTTCTTCTTTGTCCTGCCGCTCCTGTTCCCGCAGCTGAAGCCATCGGAG  1143
362   F   P   F   F   F   V   L   P   L   G   S   L   F   P   Q   L   K   P   S   E    381

1144  GGCGTCTTCAAGGTCATCTTCTGGCTCGGCTACTTCAACAGCTGCGTGAACCCGCTCATC  1203
382   G   V   F   K   V   I   F   W   L   G   Y   F   N   S   C   V   N   P   L   I    401

1204  TACCCCTGTTCCAGCCGGAGTTCAAGCGGCCTTCCTGCGCTCCGTCCTGCGCTGCCAGTGC  1263
402   Y   P   C   S   S   R   E   F   K   R   A   F   L   R   L   L   R   C   Q   C    421
```

FIG. 1G

```
                        1270                  1290                 1310
                          .                     .                    .
1264  CGTCGTCGCCGGCGGCCGCCCCTCTCTGGCGTGTCTACGGCCACCACTGGGGCCTCC.  1323
 422  R   R   R   R   R   R   P   L   W   R   V   Y   G   H   H   W   R   A   S    441

1330                  1350                 1370
                          .                     .                    .
1324  ACCAGGGCTCGCCAGGACTGCGCCCCCAGTTCGGGGCGCCCCCGACGCCCCCGAGCCCG  1383
 442  T   S   G   L   R   Q   D   C   A   P   S   S   G   D   A   P   P   G   A   P    461

1390                  1410                 1430
                          .                     .                    .
1384  CTGGCCCTCACCGCGCTCCCCGACCCCGAACCCCCAGGCACGCCCGAGATGCAG       1443
 462  L   A   L   T   A   L   P   D   D   P   E   P   P   P   G   T   P   E   M   Q    481

1450                  1470                 1490
                          .                     .                    .
1444  GCTCCGGTGGCCAGCCGTCGAAAGCCACCCAGCGCCTTCCGCGAGTGGAGGCTGCTGGGG  1503
 482  A   P   V   A   S   R   R   K   P   P   S   A   F   R   E   W   R   L   L   G    501
```

FIG. 1H

```
1504  CCGTTCCGGAGACCCACGACCCCAGCTGCGGCCAAAGTCTCCAGCCTGTCGCACAAGATC  1563
 502   P  F  R  R  P  T  T  Q  L  R  A  K  V  S  S  L  S  H  K  I   521

1564  CGGCGCCCGGGGGCGCGCAGAGGCAGCCCAGCGTGCGCCCAGCGCTCAGAGGTGGAGGCT  1623
 522   R  A  G  G  A  Q  R  A  E  A  A  C  A  Q  R  S  E  V  E  A   541

1624  GTGTCCCTAGGCGTCCCACACGAGGTGGCCGAGGGCGCCACCTGCCAGGCCTACGAATTG  1683
 542   V  S  L  G  V  P  H  E  V  A  E  G  A  T  C  Q  A  Y  E  L   561

1684  GCCGACTACAGCAACCTACGGGAGACCGATATTTAAGGACCCCAGAGCTAGGCCCGGGAG  1743
 562   A  D  Y  S  N  L  R  E  T  D  I  *                            572
```

FIG. 1I

```
          1750            1770              1790              1803
1744 TGTGCTGGGCTTGGGGGTAAGGGGACCAGAGAGGGCGGGCTGGTGTGTTCTAAGAGCCCCCG
          1810            1830              1850              1863
1804 TGCAAATCGGAGACCCGGAAACTGATCAGGGCAGCTGCTCTGTGACATCCCTGAGGAACT
          1870            1890              1910              1923
1864 GGGCAGAGCTTGAGGCTGGAGCCCCTTGAAAGTGAAAAGTAGTGGGGCCCCCTGCTGGAC
          1930            1950              1963
1924 TCAGGTGCCCCAGAACTCTTTTCTTAGAAGGGAGAGGCTGC
```

FIG. 2A

```
-122                                                                                  -63
      GCCAGGAGGGCGCCTCTGGGAAGAAGACCACGGGGAAGCAAGTTTCAGGGCAGCTGAG
     120              -100              -80

-62                                                                                   -3
      GAGCCTTCGCCGCAGCCCTTCCGAGCCCAATCATCCCCCAGGCTATGGAGGGCGACTCT
      -60               -40               -20

-2                                                                                   57
   0  AAGATGAATCCCGACCTGGACACCGGCCACAACACATCAGCACCTGCCCACTGGGAGAG  19
       M  N  P  D  L  D  T  G  H  N  T  S  A  P  A  H  W  G  E
                        20                40

58                                                                                  117
  20  TTGAAAAATGCCAACTTCACTGGCCCCAACCAGACCTGAGCAACTCCACACTGCCCCAG  39
       L  K  N  A  N  F  T  G  P  N  Q  T  S  S  N  S  T  L  P  Q
                        80                100
```

FIG. 2B

```
                          120                 140                 160
118  CTGGACATCACCAGGGCCATCTCTGTGGGCCTGGTGCTGGGCGCCTTCATCCTCTTTGCC  177
 40   L  D  I  T  R  A  I  S  V  G  L  V  L  G  A  F  I  L  F  A   59

180                 200                 220
178  ATCGTGGGCAACATCCTAGTCATCTTGTCTGTGGCCTGCAACCGGCACCTGCGGACGCCC  237
 60   I  V  G  N  I  L  V  I  L  S  V  A  C  N  R  H  L  R  T  P   79

240                 260                 280
238  ACCAACTACTTCATTGTCAACCTGGCCATGGCCGACCTGCTGTTGAGCTTCACCGTCCTG  297
 80   T  N  Y  F  I  V  N  L  A  M  A  D  L  L  L  S  F  T  V  L   99

300                 320                 340
298  CCCTTCTCAGCGGCCCTAGAGGTGCTCGGCTACTGGGGCGTGCTGGGGCGATCTTCTGTGAC  357
100   P  F  S  A  A  L  E  V  L  G  Y  W  V  L  G  R  I  F  C  D  119
```

FIG. 2C

```
            360         380         400
358  ATCTGGGCAGCCGTGGATGTCCTGTGCTGCACAGCGTCCATTCTGAGCCTGTGCGCCATC  417
120   I  W  A  A  V  D  V  L  C  C  T  A  S  I  L  S  L  C  A  I   139

420         440         460
418  TCCATCGATCGCTACATCGGGGTGCGCTACTCTCTGCAGTATCCCACGCTGGTCACCCGG  477
140   S  I  D  R  Y  I  G  V  R  Y  S  L  Q  Y  P  T  L  V  T  R   159

480         500         520
478  AGGAAGGCCATCTTGGCGCTGCTCAGTGTCTGGTCTTGTTCCACCGTCATCTCCATCGGG  537
160   R  K  A  I  L  A  L  L  S  V  W  V  L  S  T  V  I  S  I  G   179

540         560         580
538  CCTCTCCTTGGGTGGAAGGAGCCGGCACCCAACGATGACAAGGAGTGCGGGGTCACCGAA  597
180   P  L  G  W  K  E  P  A  P  N  D  D  K  E  C  G  V  T  E   199
```

FIG. 2D

```
                    600                           620                           640
                      .                             .                             .
   598  GAACCCTTCTATGCCCTCCTTCTCCTCTCTGGCTCCTTCTACATCCCTCTGGCGGTCATT  657
   200    E  P  F  Y  A  L  F  S  S  L  G  S  F  Y  I  P  L  A  V  I     219

660                           680                           700
                      .                             .                             .
   658  CTAGTCATGTACTGCCGTGTCTATATAGTGGCCAAGAGAACCACCAAGAACCTAGAGGCA  717
   220    L  V  M  Y  C  R  V  Y  I  V  A  K  R  T  T  K  N  L  E  A     239

720                           740                           760
                      .                             .                             .
   718  GGAGTCATGAAGGAGATGTCCAACTCCAAGGAGCTGACCCTGAGGATCCATTCCAAGAAC  777
   240    G  V  M  K  E  M  S  N  S  K  E  L  T  L  R  I  H  S  K  N     259

780                           800                           820
                      .                             .                             .
   778  TTTCACGAGGACACCCTTAGCAGTACCAAGGCCAAGGGCCACAACCCCAGGAGTTCCATA  837
   260    F  H  E  D  T  L  S  S  T  K  A  K  G  H  N  P  R  S  S  I     279
```

FIG. 2E

```
                           840                       860                       880
                            .                         .                         .
 838  GCTGTCAAACTTTTTAAGTTCTCCAGGAAAAGAAAGCAGCTAAGACGTTGGGCATTGTG  897
 280   A  V  K  L  F  K  F  S  R  E  K  K  K  A  A  K  T  L  G  I  V   299

900                       920                       940
                            .                         .                         .
 898  GTCGGTATGTTCATCTTGTGCTGGCTACCCTTCTTCATCGCTCTACCGCTTGGCTCCTTG  957
 300   V  G  M  F  I  L  C  W  L  P  F  F  I  A  L  P  L  G  S  L   319

960                       980                      1000
                            .                         .                         .
 958  TTCTCCACCCTGAAGCCCCCAGACGCCGTGTTCAAGGTGGTGTTCTGGCTGGGCTACTTC 1017
 320   F  S  T  L  K  P  P  D  A  V  F  K  V  V  F  W  L  G  Y  F   339

1020                      1040                      1060
                            .                         .                         .
1018  AACAGCTGCCTCAACCCCATCATCTACCCCATGCTCCAGCAAGGAGTTCAAGGCGCTTTC 1077
 340   N  S  C  L  N  P  I  I  Y  P  C  S  S  K  E  F  K  R  A  F   359
```

FIG. 2F

```
1078  GTGCGCATCCTCGGGGTGCCAGTGCCGCAGTGCCGCCGACGCCGCCGT  1137
360    V  R  I  L  G  C  Q  C  R  G  R  R  R  R  R  R    379

1138  CGCCTGGGCGGCTGCGCCTACACCTACCGGCCGTGGACGCGTCGCTGGAGCGC  1197
380    R  L  G  G  C  A  Y  T  Y  R  P  W  T  R  G  G  S  L  E  R    399

1198  TCGCAGTCGCGCAAGGACTCGCTGGACGACAGCTGCCTGAGCGGCAGCCAGCGG  1257
400    S  Q  S  R  K  D  S  L  D  D  S  G  S  C  L  S  G  S  Q  R    419

1258  ACCCTGCCCTCGGCCTCGCCCAGCCCGGGCTACCTGGGCCGGGCGCCACCGCCAGTC  1317
420    T  L  P  S  A  S  P  S  P  G  Y  L  G  R  G  A  P  P  P  V    439
```

FIG. 2G

```
1318  GAGCTGTGCGCCTTCCCCGAGTGGAAGGCGCCCGGCGCCCTCCTGAGCCTGCCCGCGCCT  1377
 440  E   L   C   A   F   P   E   W   K   A   P   G   A   L   L   S   L   P   A   P   459

1378  GAGCCCCCCGGCCGACGCCGCCGCCACGACTCGGGCCCGCTCTTCACCTTCAAGCTCCTG  1437
 460  E   P   P   G   R   R   G   R   H   D   S   G   P   L   F   T   F   K   L   L   479

1438  ACCGAGCCCGAGAGCCCCGGAACCGACGGCGCCAGCAACGGAGGCTGCGAGGCCGCG     1497
 480  T   E   P   E   S   P   G   T   D   G   G   A   S   N   G   G   C   E   A   A   499

1498  GCCGACGTGGCCAACGGGCAGCCCGGCTTCAAAAGCAACATGCCCCTGGCCCCGGGCAG  1557
 500  A   D   V   A   N   G   Q   P   G   F   K   S   N   M   P   L   A   P   G   Q   519
```

FIG. 2H

```
       1560            1580            1600            1615
1558   TTTTAGGGCCCCCGTGCGCAGCTTTCTTTCCCTGGGAGGAAACATCGTGGGGGGA   520
520    F    *
```

FIG. 3A

```
-124  CCAGCCAAACCACTGGCAGGCTCCCCTCCAGCCGAGACCTTTTATTCCCGGCTCCCGAGCT   -65
                    -120                    -100                     -80

-64  CCGCCTCCGCGCCAGCCCGGGAGGTGCCCTGACCCGGACCCTCGCCCCCGGCCCCCGGCTG    -5
                     -60                     -40                     -20

-4  GGACCATGGTGTTCTCTCGGGAAATGCTTCCGACAGCTCCAACTGCACCCAACCGCCGG     55
   0   M  V  F  L  S  G  N  A  S  D  S  S  N  C  T  Q  P  P  A      19
                       0                      20                      40

56  CACCGGTGAACATTCCAAGGCCATTCTGCTCGGGGTGATCTTGGGGGCCTCATTCTTT     115
  20   P  V  N  I  S  K  A  I  L  L  G  V  I  L  G  G  L  I  L  F   39
                      60                      80                     100
```

FIG. 3B

```
116  TCGGGGTGCTGGGTAACATCCTAGTGATCCTCTCCGTAGCCTGTCACCGACACCTGCACT  175
 40    G  V  L  G  N  I  L  V  I  L  S  V  A  C  H  R  H  L  H  S   59

176  CAGTCACGGCACTACTACATCGTCAACCTGGGGCCGACCTCCTGCTCACCTCCACGG     235
 60    V  T  H  Y  Y  I  V  N  L  A  V  A  D  L  L  L  T  S  T  V   79

236  TGCTGCCCTTCTCCGCCATCTTCGAGGTCCTAGGCTACTGGGCCTTCGGCAGGGTCTTCT  295
 80    L  P  F  S  A  I  F  E  V  L  G  Y  W  A  F  G  R  V  F  C   99

296  GCAACATCTGGGCGGCAGTGGATGTGCTGTGCTGCACCGCGTCCATCATGGGCCTCTGCA  355
100    N  I  W  A  A  V  D  V  L  C  C  T  A  S  I  M  G  L  C  I  119
```

FIG. 3C

```
                 360              380              400
356  TCATCTCCATGACCGCTACATCGGCGTGAGCTACCCGCTGCGCTACCAACCATCGTCA  415
120   I  S  I  D  R  Y  I  G  V  S  Y  P  L  R  Y  P  T  I  V  T   139

420              440              460
416  CCCAGAGGAGGGTCTCATGGCTCTGCTCTGCGTCTGGGCACTCTCCCTGGTCATATCCA  475
140   Q  R  R  G  L  M  A  L  L  C  V  W  A  L  S  L  V  I  S  I   159

480              500              520
476  TTGGACCCCTGTTCGGCTGGAGGCAGCCCGAGGACGAGACCATCTGCCAGATCA  535
160   G  P  L  F  G  W  R  Q  P  A  P  E  D  E  T  I  C  Q  I  N   179

540              560              580
536  ACGAGGAGCCGGGCTACGTGCTCTTCTCAGGCTGGGCTCCTTCTACCTGCCTCTGGCCA  595
180   E  E  P  G  Y  V  L  F  S  A  L  G  S  F  Y  L  P  L  A  I   199
```

FIG. 3D

```
596  TCATCCTGGTCATGTACTGTCGCCGTCTACGTGGTGGCCAAGAGGGAGAGCCGGGGCCTCA  655
200   I  L  V  M  Y  C  R  V  Y  V  V  V  A  K  R  E  S  R  G  L  K   219

656  AGTCTGGCCTCAAGACCGACAAGTCGGACTCGGAGCAAGTGACGCTCCGCATCCATCGGA  715
220   S  G  L  K  T  D  K  S  D  S  E  Q  V  T  L  R  I  H  R  K   239

716  AAAACGCCCCGGCAGGAGGCAGGCGGGATGGCCAGCGCCAAGACCAAGACGCACTTCTCAG  775
240   N  A  P  A  G  G  S  G  M  A  S  A  K  T  K  T  H  F  S  V   259

776  TGAGGCTCCTCAAGTTCTCCCGGGAGAAGAAAGCGGCCAAAACGCTGGGCATCGTGGTCG  835
260   R  L  K  F  S  R  E  K  K  A  A  K  T  L  G  I  V  V  G   279
```

FIG. 3E

```
                      840                          860                           880
836  GCTGCTTCGTCCTCCTCTGCTGCTGGCTGCCTTTTTCTTAGTCATGCCCATTGGGTCTTCTCC  895
280    C   F   V   L   C   W   L   P   F   F   L   V   M   P   I   G   S   F   F   P   299

900                          920                           940
896  CTGATTTCAAGCCCTCTGAAACAGTTTTTAAAATAGTATTTTGGCTCGGATATCTAAACA  955
300    D   F   K   P   S   E   T   V   F   K   I   V   F   W   L   G   Y   L   N   S   319

960                          980                          1000
956  GCTGCATCAACCCCATCATATACCCATGCTCCAGCCAAGAGTTCAAAAGGCCTTTCAGA  1015
320    C   I   N   P   I   I   Y   P   C   S   S   Q   E   F   K   K   A   F   Q   N   339

1020                         1040                          1060
1016 ATGTCTTGAGAATCCAGTGTCTCTGCAGAAAGCAGTCTTCCAAACATGCCCTGGGCTACA  1075
340    V   L   R   I   Q   C   L   C   R   K   Q   S   S   K   H   A   L   G   Y   T   359
```

FIG. 3F

```
                                       1100                    1120
1076 CCCTGCACCCGCCCAGCCAGGCCGTGGAAGGGCAACACAAGGACATGGTGCGCATCCCCG  1135
 360  L   H   P   P   S   Q   A   V   E   G   Q   H   K   D   M   V   R   I   P   V   379

1140                    1160                    1180
1136 TGGGATCAAGAGAGACCTTCTACAGGATCTCCAAGACGGATGGCGTTTGTGAATGGAAAT  1195
 380  G   S   R   E   T   F   Y   R   I   S   K   T   D   G   V   C   E   W   K   F   399

1200                    1220                    1240
1196 TTTTCTCTTCCATGCCCCGTGGATCTGCCAGGATTACAGTGTCCAAAGACCAATCCTCCT  1255
 400  F   S   S   M   P   R   G   S   A   R   I   T   V   S   K   D   Q   S   S   C   419

1260                    1280                    1300
1256 GTACCACAGCCCGGGTGAGAAGTAAAAGCTTTTGCAGGTCTGCTGCTGTGTAGGCCCT  1315
 420  T   T   A   R   V   R   S   K   S   F   L   Q   V   C   C   C   V   G   P   S   439
```

FIG. 3G

```
1316  CAACCCCCAGCCCTTGACAAGAACCAATCAAGTTCCAACCATTAAGGTCCACACCATCTCCC  1375
440    T  P  S  L  D  K  N  H  Q  V  P  T  I  K  V  H  T  I  S  L   459

1376  TCAGTGAGAACGGGGAGGAAGTCTAGGACAGGAAAGATGCAGAGGAAAGGGAATATCTT    1435
460    S  E  N  G  E  E  V  *                                       466

1436  AGGTACCATACCCTGGAGTTCTAGAGGATTCCTCGACAAGCTTATTCCGATCCAGACATG   1495

1496  ATAGATACATTGATGAGTT  1514
```

FIG. 4A

```
                   1
human  alpha1a    mtfrdllsvs fegprpdssa ggssaggggg saggaapseg
H318/3 alpha1a    .......... .......... .......... ..........
Rat    alpha1a    mtfrdilsvt fegprsssst ggsgagggag tvg....peg
       Consensus  MTFRD-LS-- FEGPR--SS- GGS-AGGG-G --G-----EG 41                                      80
human  alpha1a    pavggvpgg- ggggg-vga- sgednrssa. .....gepgs
H318/3 alpha1a    ........m- aalrs-mma- ylsewrtpty rstemvqrlr
Rat    alpha1a    gavggvpg.- tggga-vgt- sgednqsst. ......gepg
       Consensus  --------A- -----V---G ---------- ----------

81                                     120
human  alpha1a    ag-ggdvngt ---------- ----m----- ----------
H318/3 alpha1a    me-vqhstst ---------- ----m----- ----------
Rat    alpha1a    aa-sgevngs ---------- ----t----- ----------
       Consensus  --A------- AAVGGLVVSA QGVGVGVFLA AFIL-AVAGN 121                                     160
human  alpha1a    ---------- ---------- ---t------ ----------
H318/3 alpha1a    ---------- ---------- ---t------ ----------
Rat    alpha1a    ---------- ---------- ---a------ ----------
       Consensus  LLVILSVACN RHLQTVTNYF IVNLAVADLL LSA-VLPFSA
```

FIG. 4B

```
                    161                                                             200
human   alpha1      ----------  ----------  -------a--  ----------  ----------
H318/3  alpha1      ----------  ----------  -------a--  ----------  ----------
Rat     alpha1      ----------  ----------  -------t--  ----------  ----------
        Consensus   TMEVLGFWAF  GR-FCDVWAA  VDVLCCTASI  LSLCTISVDR 201                                                             240
human   alpha1      ----------  ----------  ----------  ------v---  ----------
H318/3  alpha1      ----------  ----------  ----------  ------v---  ----------
Rat     alpha1      ----------  ----------  ----------  ------a---  ----------
        Consensus   YVGVRHSLKY  PAIMTERKAA  AILALLW-VA  LVVSVGPLLG 241                                                             280
human   alpha1      ----------  -------a--  ----------  ---v------  ----------
H318/3  alpha1      ----------  -------a--  ----------  ---v------  ----------
Rat     alpha1      ----------  -------v--  ----------  ---i------  ----------
        Consensus   WKEPVPPDER  FCGITEE-GY  A-FSSVCSFY  LPMAVIVVMY 281                                                             320
human   alpha1      ----------  ------v---  ---r------  ----------  ---------g
H318/3  alpha1      ----------  ------v---  ---r------  ----------  ---------g
Rat     alpha1      ----------  ------i---  ---p------  ----------  ---------s
        Consensus   CRVYVVARST  TRSLEAG-KR  E-GKASEVVL  RIHCRGAAT-
```

FIG. 4C

```
              321                                                           360
human  alpha1a  -d-ah-mr-a  ----f-----  ----------  ----------  ----------
H318/3 alpha1a  -d-ah-mr-a  ----f-----  ----------  ----------  ----------
Rat    alpha1a  -k-yp-tq-s  ----l-----  ----------  ----------  ----------
       Consensus A-G---G---S-  KGHT-RSSLS  VRLLKFSREK  KAAKTLAIVV 361                                                           400
human  alpha1a  ----------  ----------  ----------  ----------  ----------
H318/3 alpha1a  ----------  ----------  ----------  ----------  ----------
Rat    alpha1a  ----------  ----------  ----------  ----------  ----------
       Consensus GVFVLCWFPF  FFVLPLGSLF  PQLKPSEGVF  KVIFWLGYFN 401                                                           440
human  alpha1a  ----------  ----------  ----------  ----.rp-wrv
H318/3 alpha1a  ----------  ----------  ----------  ----.rp-wrv
Rat    alpha1a  ----------  ----------  ----------  ----lws-rpp
       Consensus SCVNPLIYPC  SSREFKRAFL  RLLRCQCRRR  RRR----L----

441                                                           480
human  alpha1a  yg..hhw---  ...stsgl-q  dca----gdap  --ap-alt-1
H318/3 alpha1a  yg..hhw---  ...stsgl-q  dca----gdap  --ap-alt-1
Rat    alpha1a  lasldrr--f  rlrpqpsh-s  prg----phct  --cg-grh-.
       Consensus ------RA-  ------R---  ---PSS----  PG--L----A-
```

FIG. 4D

```
                481                                                      520
human alpha1a   pdpdpeppgt pem-apv--r  -k..ppsafr ewrllgpfr-
H318/3 alpha1a  pdpdpeppgt pem-apv--r  -shpapsasg gcwgrsgdp-
Rat    alpha1a  .....gdag  fgl-qsk--l  -.......lr ewrllgplq-
       Consensus ---------  ---Q---AS-  R--------  --------R 521                                                      560
human alpha1a   -ttqlrakvs slshkiragg  -q-aeaac-q -seveavslg
H318/3 alpha1a  -scapkspac rtrsppgars  -q-qraps-q -wrlcp*...
Rat    alpha1a  -ttqlrakvs slshkirs.g  -r-aetac-l -seveavsln
       Consensus P--------  ---------  --------A- R-----SL- 561                                                      588
human alpha1a   vphevaegat cqayeladys  nlretdi*
H318/3 alpha1a  ..........  ..........  .......
Rat    alpha1a  vpqdgaeavi cqayepgdys  nlretdi*
       Consensus VP---AE---  CQAYE--DYS NLRETDI*
```

FIG. 5A

```
                                                                              40
Rat     alpha1b  ------------  -----------  ------------  -dd---------
Hamster alpha1b  ------------  ------q----  -----------   -da---------
Human   alpha1b  ------------  ------h----  -----------   -na---------
Consensus        MNPDLDTGHN    TSAPA-WGEL   K--NFTGPNQ    TSSNSTLPQL 80
Rat     alpha1b  -v----------  ------------ -----------   ------------
Hamster alpha1b  -v----------  ------------ -----------   ------------
Human   alpha1b  -i----------  ------------ -----------   ------------
Consensus        D-TRAISVGL    VLGAFILFAI   VGNILVILSV    ACNRHLRTPT 120
Rat     alpha1b  ------------  ------------ ---t--------  ------------
Hamster alpha1b  ---i--------  ------------ ---t--------  ------------
Human   alpha1b  ---m--------  ------------ ---a--------  ------------
Consensus        NYFIVNLA-A    DLLLSFTVLP   FSA-LEVLGY    WVLGRIFCDI 160
Rat     alpha1b  ------------  ------------ ------------  ------------
Hamster alpha1b  ------------  ------------ ------------  ------------
Human   alpha1b  ------------  ------------ ------------  ------------
Consensus        WAAVDVLCCT    ASILSLCAIS   IDRYIGVRYS    LQYPTLVTRR
```

FIG. 5B

```
                     161
Rat     alpha1b     ---------- ---------- ---------- ---------- ----------                200
Hamster alpha1b     ---------- ---------- ---------- ---------- ----------                |
Human   alpha1b     ---------- ---------- ---------- ---------- ----------                |
Consensus           KAILALLSVW VLSTVISIGP LLGWKEPAPN DDKECGVTEE 201                                                                  240
Rat     alpha1b     --c---c--- ---------- ---------- ---------- ----------                |
Hamster alpha1b     --y---s--- ---------- ---------- ---------- ----------                |
Human   alpha1b     --y---s--- ---------- ---------- ---------- ----------                |
Consensus           PF-ALF-SLG SFYIPLAVIL VMYCRVYIVA KRTTKNLEAG 241                                                                  280
Rat     alpha1b     ---------- ---------- ---------- ---------- ----------                |
Hamster alpha1b     ---------- ---------- ---------- ---------- ----------                |
Human   alpha1b     ---------- ---------- ---------- ---------- ----------                |
Consensus           VMKEMSNSKE LTLRIHSKNF HEDTLSSTKA KGHNPRSSIA 281                                                                  320
Rat     alpha1b     ---------- ---------- ---------- ---------- ----------                |
Hamster alpha1b     ---------- ---------- ---------- ---------- ----------                |
Human   alpha1b     ---------- ---------- ---------- ---------- ----------                |
Consensus           VKLFKFSREK KAAKTLGIVV GMFILCWLPF FIALPLGSLF
```

FIG. 5C

```
                                                                    360
Rat     alpha1b  ----------  ----------  ----------  ----------  ------m
Hamster alpha1b  ----------  ----------  ----------  ----------  ------m
Human   alpha1b  ----------  ----------  ----------  ----------  ------v
        Consensus  STLKPPDAVF  KVVFWLGYFN  SCLNPIIYPC  SSKEFKRAF- 321
                                                                    400
Rat     alpha1b  ----------  ---..---gg  ----a-----  ----------  -------
Hamster alpha1b  ----------  ---..---sg  ----a-----  ----------  -------
Human   alpha1b  ----------  ----rg---gr  ----g-----  ----------  -------
        Consensus  RILGCQC---R  --RRRRRRRR  LG-CAYTYRP  WTRGGSLERS 361
                                                                    440
Rat     alpha1b  ----------  ----m---qk  ----------  ----------  ---tq--v-
Hamster alpha1b  ----------  ----m---sq  ----------  ----------  ---aq--l-
Human   alpha1b  ----------  ----l---sq  ----------  ----------  ---ap--v-
        Consensus  QSRKDSLDDS  GSC-SG---RT  LPSASPSPGY  LGRG--PP-E 401
                                                                    480
Rat     alpha1b  ---f-----p  ----------  ------l---  ----------  -------g
Hamster alpha1b  ---y----.s  ----------  ------l---  ----------  -------g
Human   alpha1b  ---f----ap  ----pa----  ------h---  ----------  -------t
        Consensus  LCA-PEWK--  GALLSL--PE  PPGRRGR-DS  GPLFTFKLL-

```
                        481                                520
Rat     alpha1b         d------eat  ------dttt  -l-------  ------g--h-
Hamster alpha1b         e------egd  ------datt  -l-------  ------a--h-
Human   alpha1b         e------dgg  ------eaaa  -v-------  ------a--q-
        Consensus       -PESPGT---  ASNGGC----  D-ANGQPGFK SNMPL-PG-F 521
Rat     alpha1b         *
Hamster alpha1b         *
Human   alpha1b         *
        Consensus       *
```

FIG. 6A

```
                   1
Human    alpha1c   ---------- ---------- ----q--a-- ----------      40
Bovine   alpha1c   ---------- ---------- ----h--p-- ----------
         Consensus                       MVFLSGNASD SSNCT-PP-P VNISKAILLG VILGGLILFG 41
Human    alpha1c   ---------- ---------- ---------- ----------      80
Bovine   alpha1c   ---------- ---------- ---------- ----------
         Consensus                       VLGNILVILS VACHRHLHSV THYYIVNLAV ADLLLTSTVL 81
Human    alpha1c   -----v---- ---------- ---------i ----------     120
Bovine   alpha1c   -----i---- ---------- ---------v ----------
         Consensus                       PFSAIFE-LG YWAFGRVFCN -WAAVDVLCC TASIMGLCII 121
Human    alpha1c   ---------- ---------- ---------- r---------     160
Bovine   alpha1c   ---------- ---------- ---------- k---------
         Consensus                       SIDRYIGVSY PLRYPTIVTQ -RGLMALLCV WALSLVISIG
```

FIG. 6B

```
                  161
Human    alpha1c  ---------- ---------- ---------- ---------- ----l---a-    200
Bovine   alpha1c  ---------- ---------- ---------- ---------- ----v---t-
Consensus         PLFGWRQPAP EDETICQINE EPGYVLFSAL GSFY-PL-II 201                                                         240
Human    alpha1c  ---------- ---------- ---------- ---------- ----------
Bovine   alpha1c  ---------- ---------- ---------- ---------- ----------
Consensus         LVMYCRVYVV AKRESRGLKS GLKTDKSDSE QVTLRIHRKN 241
Human    alpha1c  -pa-----ma- --t------- ---------- ---------- ----------    280
Bovine   alpha1c  -qv-----vt- --n------- ---------- ---------- ----------
Consensus         A--GGSG--S AK-KTHFSVR LLKFSREKKA AKTLGIVVGC 281
Human    alpha1c  ---------- ---------- ---------- -k-------- v---------    320
Bovine   alpha1c  ---------- ---------- ---------- -r-------- a---------
Consensus         FVLCWLPFFL VMPIGSFFPD F-PSETVFKI -FWLGYLNSC
```

FIG. 6C

```
                   321                                                              360
Human    alpha1c   -----------  -----------  -----c-----  -----a-----  -----------
Bovine   alpha1c   -----------  -----------  -----r-----  -----t-----  -----------
         Consensus INPIIYPCSS   QEFKKAFQNV   LRIQCL-RKQ   SSKH-LGYTL 361                                                              400
Human    alpha1c   -p---qav---  -----m-----  -----r-----  -----r-----  -----f-----
Bovine   alpha1c   -a---hvl---  -----l-----  -----a-----  -----k-----  -----i-----
         Consensus H-PS---EGQ   HKD-VRIPVG   S-ETFY-ISK   TDGVCEWK-F 401                                                              440
Human    alpha1c   ---m-------  -----i-----  t-sk-q-s---  -----------  -----v-----
Bovine   alpha1c   ---l-------  -----m-----  a-ar-p-a---  -----------  -----l-----
         Consensus SS-PRGSAR-   -V--D-S-CT   TARVRSKSFL   QVCCC-GPST 441                                                              467
Human    alpha1c   --ldk----v-  -----v-----  -----------*
Bovine   alpha1c   --hge----i-  -----i-----  -----------*
         Consensus PS---NHQ-P   TIK-HTISLS   ENGEEV*
```

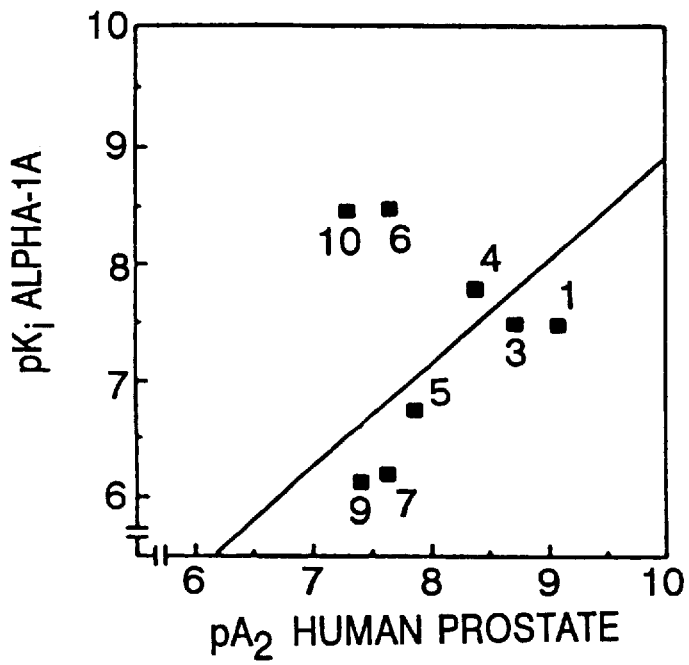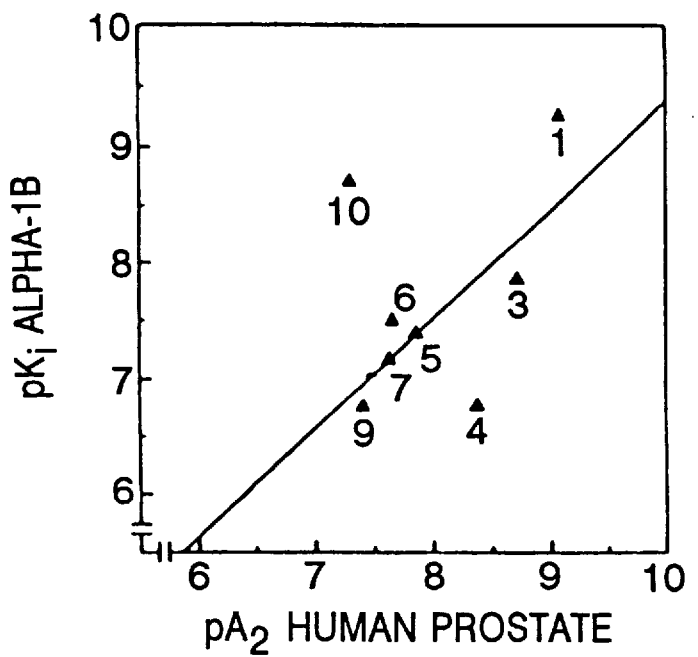

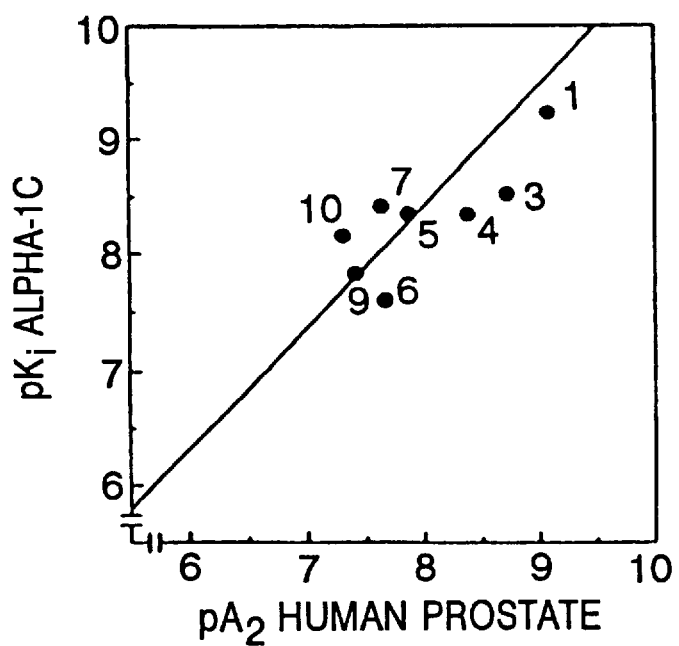

DNA ENDODING HUMAN ALPHA 1 ADRENERGIC RECEPTORS

This application is a 371 national stage filing of PCT/US93/09187, filed Sep. 24, 1993, which is a continuation-in-part of U.S. Ser. No. 07/952,798, filed Sep. 25, 1992, now abandoned.

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which this invention pertains.

Although adrenergic receptors (ARs) bind the same endogenous catecholamines (epinephrine and norepinephrine, NE) their physiological as well as pharmacological specificity is markedly diverse. This diversity is due primarily to the existence of at least nine different proteins encoding three distinct adrenergic receptors types ($\alpha_1$, $\alpha 2$, and $\beta$). These proteins belong to the super-family of G-protein coupled receptors, and are characterized by a single polypeptide chain which span the plasma membrane seven times, with an extracellular amino terminus, and a cytoplasmic carboxyl terminus. The molecular cloning of three genes encoding $\alpha_1$-ARs supports the existence of pharmacologically and anatomically distinct $\alpha_1$-receptor subtypes. The $\alpha_{1b}$-receptor was originally cloned from a hamster smooth muscle cell line cDNA library, and encodes a 515 a.a. peptide that shows 42–47% homology with other ARs. The message for the $\alpha_{1b}$-receptor is abundant in rat liver, heart, cerebral cortex and kidney, and its gene was localized to human chromosome 5 (4). A second cDNA clone from a bovine brain library was found which encoded a 466-residue polypeptide with 72% homology to the $\alpha_{1b}$-AR gene. It was further distinguished from $\alpha_{1b}$ by the finding that its expression was restricted to human hippocampus, and by its localization to human chromosome 8 and it has been designated as the $\alpha_{1c}$-AR (20). The cloning of an $\alpha_{1a}$-AR has been reported recently. This gene, isolated from a rat brain cDNA library, encodes a 560-residue polypeptide that shows 73% homology with the hamster $\alpha_{1b}$-receptor. The message for this subtype is abundant in rat vas deferens, aorta, cerebral cortex and hippocampus, and its gene has been localized to human chromosome 5 (12).

Pharmacological studies have demonstrated the existence of two $\alpha_1$-adrenergic receptor subtypes. The studies of $\alpha_1$-AR-mediated responses in vascular tissue suggested the possible existence of receptor subtypes, based on the potency and efficacy of adrenergic agonists, as well as differential sensitivity of $\alpha_1$ receptor-mediated responses to extracellular calcium and calcium channel blockers (6, 24). Although radioligand binding studies of brain $\alpha_1$-ARs with either [$^3$H]WB4101 and [$^3$H]prazosin showed good agreement with the potency of $\alpha$-adrenergic antagonists on vascular responses (23, 10), subsequent binding studies of rat brain $\alpha_1$-ARs provided strong evidence for the existence of receptor heterogeneity, based on the relative affinities for prazosin and WB4101 (15). These observations were supported by the finding that chloroethylclonidine (CEC) inactivated 50% of the $\alpha_1$ sites from rat cerebral cortex and 80% of the binding sites from liver or spleen ($\alpha_{1b}$), but did not inactivate $\alpha_1$-receptors from the hippocampus or vas deferens ($\alpha_{1a}$) (14). Taken together, these results suggested a classification of the $\alpha_{1a}$-subtype as high affinity for WB4101 and insensitive to alkylation by CEC, and $\alpha_{1b}$-subtype as 10 to 20 fold lower affinity for WB4101, but sensitive to inactivation by CEC. Consistent with this evidence the transfection of the hamster $\alpha_{1b}$ gene into COS-7 cells induced the expression of an $\alpha$1-receptor with high affinity for WB4101, 95% of which could be inactivated by CEC. Conversely, upon expression of the rat $\alpha_{1a}$ receptor gene in COS-7 cells, it showed a 10-fold higher affinity for WB4101 than the $\alpha_{1b}$-receptor, and the binding site was resistant to inactivation by CEC.

The existence of the $\alpha_{1c}$ receptor was not predicted from pharmacological data and upon expression it showed 16 and 30 fold higher affinity for WB4101 and phentolamine respectively, than the $\alpha_{1b}$-receptor and was partially inactivated (65%) by CEC.

Molecular cloning and pharmacological studies have demonstrated the existence of at least three $\alpha_1$-adrenergic receptor subtypes. However, it is not clear whether the pharmacological properties of these three cognates might be due also to species differences. This caveat is particularly relevant in the case of the bovine $\alpha_{1c}$ receptor, due to its restricted species and tissue expression. The cloning and expression of the human $\alpha_1$ adrenergic receptors will allow the further characterization of the pharmacology of the individual human $\alpha_1$ receptor subtypes.

SUMMARY OF THE INVENTION

This invention provides and isolated nucleic acid molecule encoding a human $\alpha_1$ adrenergic receptor. This invention further provides an isolated nucleic acid molecule encoding a human $\alpha_{1a}$ receptor. In one embodiment of this invention, the nucleic acid molecule comprises a plasmid pcEXV-$\alpha_{1a}$. This invention also provides an isolated nucleic acid molecule encoding a human $\alpha_{1b}$ receptor. In one embodiment of this invention, the nucleic acid molecule comprises a plasmid pcEXV-$\alpha_{1b}$. This invention further provides an isolated nucleic acid molecule encoding a human $\alpha_{1c}$ receptor. In one embodiment of this invention, the nucleic acid molecule comprises a plasmid pcEXV-$\alpha_{1c}$.

This invention also provides vectors such as plasmids comprising a DNA molecule encoding a human $\alpha_{1a}$ receptor, adapted for expression in a bacterial, a yeast cell, or a mammalian cell which additionally comprise regulatory elements necessary for expression of the DNA in the bacteria, yeast or mammalian cells so located relative to the DNA encoding the human $\alpha_{1a}$ receptor as to permit expression thereof. This invention also provides vectors such as plasmids comprising a DNA molecule encoding a human $\alpha_{1b}$ receptor, adapted for expression in a bacterial, a yeast cell, or a mammalian cell which additionally comprise regulatory elements necessary for expression of the DNA in the bacteria, yeast or mammalian cells so located relative to the DNA encoding the human $\alpha_{1b}$ receptor as to permit expression thereof. This invention also provides vectors such as plasmids comprising a DNA molecule encoding a human $\alpha_{1c}$ receptor, adapted for expression in a bacterial, a yeast cell, or a mammalian cell which additionally comprise regulatory elements necessary for expression of the DNA in the bacteria, yeast or mammalian cells so located relative to the DNA encoding the human $\alpha_{1c}$ receptor as to permit expression thereof.

This invention provides a mammalian cell comprising a DNA molecule encoding a human $\alpha_{1a}$ receptor. This invention also provides a mammalian cell comprising a DNA molecule encoding a human $\alpha_{1b}$ receptor. This invention also provides a mammalian cell comprising a DNA molecule encoding a human $\alpha_{1c}$ receptor.

This invention provides a nucleic acid probe comprising a nucleic acid molecule of at least 15 nucleotides capable of specifically hybridizing with a sequence included within the sequence of a nucleic acid molecule encoding a human $\alpha_{1a}$ receptor. This invention provides a nucleic acid probe comprising a nucleic acid molecule of at least 15 nucleotides capable of specifically hybridizing with a sequence included within the sequence of a nucleic acid molecule encoding a human $\alpha_{1b}$ receptor. This invention provides a nucleic acid probe comprising a nucleic acid molecule of at least 15 nucleotides capable of specifically hybridizing with a sequence included within the sequence of a nucleic acid molecule encoding a human $\alpha_{1c}$ receptor.

This invention provides an antisense oligonucleotide having a sequence capable of specifically binding to any sequences of an mRNA molecule encoding a human $\alpha_{1a}$ receptor so as to prevent translation of the mRNA molecule. This invention provides an antisense oligonucleotide having a sequence capable of specifically binding to any sequences of an mRNA molecule encoding a human $\alpha_{1b}$ receptor so as to prevent translation of the mRNA molecule. This invention provides an antisense oligonucleotide having a sequence capable of specifically binding to any sequences of an mRNA molecule encoding a human $\alpha_{1c}$ receptor so as to prevent translation of the mRNA molecule.

This invention provides method for detecting expression of a specific human $\alpha_1$ adrenergic receptor, which comprises obtaining RNA from cells or tissue, contacting the RNA so obtained with a nucleic acid probe comprising a nucleic acid molecule of at least 15 nucleotides capable of specifically hybridizing with a sequence included within the sequence of a nucleic acid molecule encoding a human $\alpha_1$ receptor under hybridizing conditions, detecting the presence of any mRNA hybridized to the probe, the presence of mRNA hybridized to the probe indicating expression of the specific human $\alpha_1$ adrenergic receptor, and thereby detecting the expression of the specific human $\alpha_1$ adrenergic receptor.

This invention provides a method for detecting the expression of a specific human α1 adrenergic receptor in a cell or tissue by in situ hybridization which comprises, contacting the cell or tissue with a nucleic acid probe comprising a nucleic acid molecule of at least 15 nucleotides capable of specifically hybridizing with a sequence included within the sequence of a nucleic acid molecule encoding a human $\alpha_1$ receptor under hybridizing conditions, detecting the presence of any mRNA hybridized to the probe, the presence of mRNA hybridized to the probe indicating expression of the specific human $\alpha_1$ adrenergic receptor, and thereby detecting the expression of the specific human $\alpha_1$ adrenergic receptor.

This invention provides a method for isolating a nucleic acid molecule encoding a receptor by nucleic acid sequence homology using a nucleic acid probe, the sequence of which is derived from the nucleic acid sequence encoding a human α1 adrenergic receptor.

This invention provides a method for isolating a nucleic acid molecule encoding a human $\alpha_1$ adrenergic receptor which comprises the use of the polymerase chain reaction and oligonucleotide primers, the sequence of which are derived from the nucleic acid sequence encoding a human α1 adrenergic receptor.

This invention provides a method for isolating a human $\alpha_1$ adrenergic receptor protein which comprises inducing cells to express the human $\alpha_1$ adrenergic receptor protein, recovering the human $\alpha_1$ adrenergic receptor from the resulting cells, and purifying the human $\alpha_1$ adrenergic receptor so recovered.

This invention provides an antibody to the human $\alpha_{1a}$ adrenergic receptor. This invention also provides an antibody to the human $\alpha_{1b}$ adrenergic receptor. This invention also provides an antibody to the human $\alpha_{1c}$ adrenergic receptor.

A pharmaceutical composition comprising an amount of a substance effective to alleviate the abnormalities resulting from overexpression of a human $\alpha_{1a}$ adrenergic receptor and a pharmaceutically acceptable carrier is provided by this invention. A pharmaceutical composition comprising an amount of a substance effective to alleviate the abnormalities resulting from overexpression of a human $\alpha_{1b}$ adrenergic receptor and a pharmaceutically acceptable carrier is provided by this invention. A pharmaceutical composition comprising an amount of a substance effective to alleviate the abnormalities resulting from overexpression of a human $\alpha_{1c}$ adrenergic receptor and a pharmaceutically acceptable carrier is provided by this invention.

A pharmaceutical composition comprising an amount of a substance effective to alleviate abnormalities resulting from underexpression of a human $\alpha_{1a}$ adrenergic receptor and a pharmaceutically acceptable carrier is provided by this invention. A pharmaceutical composition comprising an amount of a substance effective to alleviate abnormalities resulting from underexpression of a human $\alpha_{1b}$ adrenergic receptor and a pharmaceutically acceptable carrier is provided by this invention. A pharmaceutical composition comprising an amount of a substance effective to alleviate abnormalities resulting from underexpression of a human $\alpha_{1c}$ adrenergic receptor and a pharmaceutically acceptable carrier is provided by this invention.

This invention provides a transgenic non-human mammal whose genome comprises a nucleic acid molecule encoding a human α1 adrenergic receptor, the DNA molecule so placed as to be transcribed into antisense mRNA complementary to mRNA encoding a human $\alpha_1$ adrenergic receptor and which hybridizes to mRNA encoding a human $\alpha_1$ adrenergic receptor thereby reducing its translation.

This invention provides a method for determining the physiological effects of varying the levels of expression of a specific human α1 adrenergic receptor which comprises producing a transgenic non-human mammal whose levels of expression of a human $\alpha_1$ adrenergic receptor can be varied by use of an inducible promoter.

This invention provides method for determining the physiological effects of expressing varying levels of a specific human $\alpha_1$ adrenergic receptor which comprises producing a panel of transgenic non-human mammals each expressing a different amount of the human $\alpha_1$ adrenergic receptor.

This invention provides a method for determining whether a ligand not known to be capable of specifically binding to a human $\alpha_1$ adrenergic receptor can bind to a human $\alpha_1$ adrenergic receptor, which comprises contacting a mammalian cell comprising a plasmid adapted for expression in a mammalian cell which further comprises a DNA molecule which expresses a human $\alpha_1$ adrenergic receptor on the cell surface with the ligand under conditions permitting binding of ligands known to bind to a human $\alpha_1$ adrenergic receptor, detecting the presence of any ligand bound to the human $\alpha_1$ adrenergic receptor, the presence of bound ligand thereby determining that the ligand binds to the human $\alpha_1$ adrenergic receptor.

This invention provides a method for screening drugs to identify drugs which interact with, and specifically bind to, a human $\alpha_1$ adrenergic receptor on the surface of a cell, which comprises contacting a mammalian cell which comprises a plasmid adapted for expression in a mammalian cell which further comprises a DNA molecule which expresses a human $\alpha_1$ adrenergic receptor on the cell surface with a plurality of drugs, determining those drugs which bind to the human $\alpha_1$ adrenergic receptor expressed on the cell surface of the mammalian cell, and thereby identifying drugs which interact with, and bind to, the human $\alpha_1$ adrenergic receptor.

This invention provides a method for identifying a ligand which binds to and activates or blocks the activation of, a human $\alpha_1$ adrenergic receptor expressed on the surface of a cell, which comprises contacting a mammalian cell which comprises a plasmid adapted for expression in a mammalian cell which further comprises a DNA molecule which expresses a human $\alpha_1$ adrenergic receptor on the cell surface with the ligand, determining whether the ligand binds to and activates or blocks the activation of the receptor using a bioassay such as a second messenger assays.

This invention also provides a method for identifying a ligand which is capable of binding to and activating or inhibiting a human $\alpha_1$ adrenergic receptor, which comprises contacting a mammalian cell, wherein the membrane lipids have been labelled by prior incubation with a labelled lipid precursor molecule, the mammalian cell comprising a plasmid adapted for expression in a mammalian cell which further comprises a DNA molecule which expresses a human $\alpha_1$ adrenergic receptor with the ligand and identifying an inositol phosphate metabolite released from the membrane lipid as a result of ligand binding to and activating an $\alpha_1$ adrenergic receptor.

This invention also provides a method for identifying a ligand that is capable of binding to and activating or inhibiting a human $\alpha_1$ adrenergic receptor, wherein the binding of ligand to the adrenergic receptor results in a physiological response, which comprises contacting a mammalian cell which comprises a plasmid adapted for expression in a mammalian cell which further comprises a DNA molecule which expresses a human $\alpha_1$ adrenergic receptor with a calcium sensitive fluorescent indicator, removing the indicator that has not been taken up by the cell, contacting the cells with the ligand and identifying an increase or decrease in intracellular $Ca^{+2}$ as a result of ligand binding to and activating or inhibiting $\alpha_1$ adrenergic receptor activity.

This invention provides a method for detecting the presence of a human $\alpha_{1a}$ a adrenergic receptor on the surface of a cell, which comprises contacting the cell with an antibody to human $\alpha_{1a}$ adrenergic receptor under conditions which permit binding of the antibody to the receptor, detecting the presence of any of the antibody bound to the human $\alpha 1a$ adrenergic receptor and thereby the presence of a human $\alpha_{1a}$ adrenergic receptor on the surface of the cell.

This invention provides a method for detecting the presence of a human $\alpha_{1b}$ adrenergic receptor on the surface of a cell, which comprises contacting the cell with an antibody to human $\alpha_{1b}$ adrenergic receptor under conditions which permit binding of the antibody to the receptor, detecting the presence of any of the antibody bound to the human $\alpha_{1b}$ adrenergic receptor and thereby the presence of a human $\alpha_{1b}$ adrenergic receptor on the surface of the cell.

This invention provides a method for detecting the presence of a human $\alpha_{1c}$ adrenergic receptor on the surface of a cell, which comprises contacting the cell with an antibody to human $\alpha_{1c}$ adrenergic receptor under conditions which permit binding of the antibody to the receptor, detecting the presence of any of the antibody bound to the human $\alpha_{1c}$ adrenergic receptor and thereby the presence of a human $\alpha_{1c}$ adrenergic receptor on the surface of the cell.

This invention provides a method of treating an abnormal condition related to an excess of activity of a human $\alpha_1$ adrenergic receptor subtype, which comprises administering an amount of a pharmaceutical composition effective to reduce $\alpha_1$ adrenergic activity as a result of naturally occurring substrate binding to and activating a specific $\alpha_1$ adrenergic receptor.

This invention provides a method for treating abnormalities which are alleviated by an increase in the activity of a specific human $\alpha_1$ adrenergic receptor, which comprises administering a patient an amount of a pharmaceutical composition effective to increase the activity of the specific human $\alpha_1$ adrenergic receptor thereby alleviating abnormalities resulting from abnormally low receptor activity.

This invention provides a method for diagnosing a disorder or a predisposition to a disorder associated with the expression of a specific human $\alpha_1$ adrenergic receptor allele which comprises: a.) obtaining DNA from subjects suffering from a disorder; b.) performing a restriction digest of the DNA with a panel of restriction enzymes; c.) electrophoretically separating the resulting DNA fragments on a sizing gel; d.) contacting the gel with a nucleic acid probe labelled with a detectable marker and which hybridizes to the nucleic acid encoding a specific human $\alpha_1$ adrenergic receptor; e.) detecting the labelled bands which have hybridized to the DNA encoding the specific $\alpha_1$ adrenergic receptor labelled with the detectable marker to create a unique band pattern specific to the DNA of subjects suffering with the disorder; f.) preparing DNA for diagnosis by steps a–e; g.)comparing the unique band pattern specific to the DNA of patients suffering from the disorder from step e and DNA obtained for diagnosis from step f to determine whether the patterns are the same or different and to diagnose thereby predisposition to the disorder if the patterns are the same.

This invention provides a method for identifying a substance capable of alleviating the abnormalities resulting from overexpression of a specific human $\alpha_1$ adrenergic receptor which comprises administering a substance to the transgenic non-human mammal comprising the DNA encoding a specific $\alpha_1$ adrenergic receptor and determining whether the substance alleviates the physical and behavioral abnormalities displayed by the transgenic nonhuman mammal as a result of overexpression of the human $\alpha_1$ adrenergic receptor subtype.

This invention provides a method for identifying a substance capable of alleviating the abnormalities resulting from underexpression of a human $\alpha_1$ adrenergic receptor subtype, which comprises administering a substance to a non-human transgenic mammal which is expressing a human $\alpha_1$ adrenergic receptor incapable of receptor activity or is underexpressing the human $\alpha_1$ adrenergic receptor subtype, and determining whether the substance alleviates the physical and behavioral abnormalities displayed by the transgenic nonhuman mammal as a result of underexpression of a human $\alpha_1$ adrenergic receptor subtype.

This invention provides a method of treating abnormalities in a subject, wherein the abnormality is alleviated by the reduced expression of a human $\alpha_1$ adrenergic receptor subtype which comprises administering to a subject an effective amount of the pharmaceutical composition effective to reduce expression of a specific $\alpha_1$ adrenergic receptor subtype.

This invention provides a method of treating abnormalities resulting from underexpression of a human $\alpha_1$ adrenergic receptor which comprises administering to a subject an amount of a pharmaceutical composition effective to alleviate abnormalities resulting from underexpression of the specific human $\alpha_1$ adrenergic receptor.

BRIEF DESCRIPTION OF THE FIGURES

FIGS. 1A–I. Nucleotide Sequence (SEQ ID NO.1) and Deduced Amino Acid Sequence (SEQ ID NO.2) of Novel Human Alpha-1a Adrenergic Receptor.

Nucleotides are presented in the 5' to 3' orientation and the coding region is numbered starting from the initiating methionine and ending in the termination codon. Deduced amino acid sequence by translation of a long open reading frame is shown, along with the 5' and 3' untranslated regions. Numbers in the left and right margins represent nucleotide (top line) and amino acid (bottom line) numberings, starting with the first position as the adenosine (A) and the initiating methionine (M), respectively.

FIGS. 2A–H. Nucleotide Sequence (SEQ ID NO.3) and Deduced Amino Acid Sequence (SEQ ID NO.4) of Novel Human Alpha-1b Adrenergic Receptor. Nucleotides are presented in the 5' to 3' orientation and the coding region is numbered starting from the initiating methionine and ending in the termination codon. Deduced amino acid sequence by translation of a long open reading frame is shown, along with the 5' and 3' untranslated regions. Numbers in the left and right margins represent nucleotide (top line) and amino acid (bottom line) numberings, starting with the first position as the adenosine (A) and the initiating methionine (M), respectively.

FIGS. 3A–G. Nucleotide Sequence (SEQ ID NO.5) and Deduced Amino Acid Sequence (SEQ ID NO.6) of Novel Human Alpha-1c Adrenergic Receptor.

Nucleotides are presented in the 5' to 3' orientation and the coding region is numbered starting from the initiating methionine and ending in the termination codon. Deduced amino acid sequence by translation of a long open reading frame is shown, along with the 5' and 3' untranslated regions. Numbers in the left and right margins represent nucleotide (top line) and amino acid (bottom line) numberings, starting with the first position as the adenosine (A) and the initiating methionine (M), respectively.

FIGS. 4A–D. Alignment of the Human Alpha-1a, H318/3 Alpha-1a, and Rat Alpha-1a Adrenergic Receptors. The deduced amino acid sequence of the human $\alpha_{1a}$ receptor (first line) (SEQ ID NO.2), from the starting methionine (M) to the stop codon (*), is aligned with the previously published human "$\alpha_{1a}$" adrenergic receptor clone, H318/3 (2) (second line) and with the rat alpha 1a (12) (third line). Also shown is a consensus amino acid sequence (fourth line), containing a hyphen at a particular position, when all receptors have the same amino acid or an amino acid at this position, when there is disparity in the three receptors. Dots indicate spaces corresponding to no amino acid at this position. Note that the human and rat $\alpha_{1a}$ receptors have greater homology in the amino (positions 1–90) and carboxyl (positions 440–598) termini than do the previously published "$\alpha_{1a}$" (H318/3) and rat $\alpha_{1a}$ receptors (see text). Dots indicate spaces corresponding to no amino acid at this position. Numbers above amino acid sequences correspond to amino acid positions, starting with the initiating methionine (M) and ending with the termination codon (*).

FIGS. 5A–D. Alignment of the Human Alpha-1b, Hamster Alpha-1b, and Rat Alpha-1b Adrenergic Receptors. The deduced amino acid sequence of the human $\alpha_{1b}$ receptor (third line) (SEQ ID NO.4), from the starting methionine (M) to the stop codon (*), is aligned with the previously published rat $\alpha_{1b}$ adrenergic receptor clone (25)(first line) and with the hamster alpha-1b (4)(second line). Also shown is a consensus amino acid sequence (fourth line), containing a hyphen at a particular position, when all receptors have the same amino acid or an amino acid at this position, when there is disparity in the three receptors. Dots indicate spaces corresponding to no amino acid at this position. Numbers above amino acid sequences correspond to amino acid position, starting with the initiating methionine (M) and ending with the termination codon (*).

FIGS. 6A–C. Alignment of the Human Alpha-1c and Bovine Alpha-1c Adrenergic Receptors. The deduced amino acid sequence of the human $\alpha_{1c}$ receptor (first line) (SEQ ID NO.6), from the starting methionine (M) to the stop codon (*), is aligned with the previously published bovine $\alpha_{1b}$ adrenergic receptor clone (13) (first line). Also shown is a consensus amino acid sequence (third line), containing a hyphen at a particular position, when all receptors have the same amino acid or an amino acid at this position, when there is disparity in the three receptors. Dots indicate spaces corresponding to no amino acid at this position. Numbers above amino acid sequences correspond to amino acid position, starting with the initiating methionine (M) and ending with the termination codon (*).

FIG. 7. Illustrates the correlation of inhibition constants ($pK_1$) for a series of $\alpha_1$ antagonists at the cloned human $\alpha_{1A}$, $\alpha_{1B}$, and $\alpha_{1C}$ receptors with efficiency of blocking contraction of human prostate tissue ($pA_2$).

DETAILED DESCRIPTION OF THE INVENTION

This invention provides an isolated nucleic acid molecule encoding a human $\alpha_1$ adrenergic receptor. This invention also provides an isolated nucleic acid molecule encoding a human $\alpha_{1a}$ a adrenergic receptor. This invention also provides an isolated nucleic acid molecule encoding a human $\alpha_{1b}$ adrenergic receptor. This invention also provides an isolated nucleic acid molecule encoding a human $\alpha_{1c}$ adrenergic receptor. As used herein, the term "isolated nucleic acid molecule" means a non-naturally occurring nucleic acid molecule that is, a molecule in a form which does not occur in nature. Examples of such an isolated nucleic acid molecule are an RNA, cDNA, or an isolated genomic DNA molecule encoding a human $\alpha_{1a}$, human $\alpha_{1b}$ or human $\alpha_{1c}$ adrenergic receptor. As used herein, the term "$\alpha_{1a}$ receptor", "$\alpha_{1b}$ receptor", or "$\alpha_{1c}$ receptor" means a molecule which is a distinct member of a class of $\alpha_1$ adrenergic receptor molecules which under physiologic conditions, is substantially specific for the catecholamines epinephrine and norepinephrine, is saturable, and having high affinity for the catecholamines epinephrine and norepinephrine. The term "$\alpha_1$ adrenergic receptor subtype" refers to a distinct member of the class of human $\alpha_1$ adrenergic receptors, which may be any one of the human $\alpha_{1a}$, $\alpha_{1b}$ or $\alpha_{1c}$ adrenergic receptors. The term "specific $\alpha_1$ adrenergic receptor" refers to a distinct member of the group or class of human $\alpha_1$ adrenergic receptors, which may be any one of the human $\alpha_{1a}$, $\alpha_{1b}$ or $\alpha_{1c}$ adrenergic receptors. One embodiment of this invention is an isolated human nucleic acid molecule encoding a human $\alpha_{1a}$ adrenergic receptor. Such a molecule may have coding sequences substantially the same as the coding sequence in FIGS. 1A–1I. The DNA molecule of FIGS. 1A–1I encodes the sequence of the human $\alpha_{1a}$ adrenergic receptor. Another, preferred embodiment is an isolated human nucleic acid molecule encoding a human $\alpha_{1b}$ adrenergic receptor. Such a molecule may have coding sequences substantially the same as the coding sequence in FIGS. 2A–2H. The DNA molecule of FIGS. 2A–2H encodes the sequence of the human $\alpha_{1b}$ adrenergic receptor. Another, preferred embodiment is an isolated human nucleic acid molecule encoding a human $\alpha_{1c}$ adrenergic receptor. Such a molecule may have coding sequences substantially the same as the coding sequence in FIGS. 3A–3G. The DNA molecule of FIGS. 3A–3G encodes the sequence of the human $\alpha_{1c}$ adrenergic receptor. One means of isolating a nucleic acid molecule encoding a $\alpha_1$ adrenergic receptor is to screen a genomic DNA or cDNA library with a natural or artificially designed DNA probe, using methods well known in the art. In the preferred embodiment of this invention, $\alpha_1$ adrenergic receptors include the human $\alpha_{1a}$, human $\alpha_{1b}$ and human $\alpha_{1c}$ adrenergic receptors and the nucleic acid molecules encoding them were isolated by screening a human genomic DNA library and by further screening of a human cDNA library to obtain the sequence of the entire human $\alpha_{1a}$, human $\alpha_{1b}$ or human $\alpha_{1c}$ adrenergic receptor. To obtain a single nucleic acid molecule encoding the entire human $\alpha_1$, $\alpha_{1b}$ or $\alpha_{1c}$ adrenergic receptor two or more DNA clones encoding portions of the same receptor were digested with DNA restriction endonucleases and ligated together with DNA ligase in the proper orientation using techniques known to one of skill in the art. DNA or cDNA molecules which encode a human $\alpha_{1a}$, $\alpha_{1b}$ or $\alpha_{1c}$ adrenergic receptor are used to obtain complementary genomic DNA, cDNA or RNA from human, mammalian or other animal sources, or to isolate related cDNA or genomic DNA clones by the screening of cDNA or genomic DNA libraries, by methods described in more detail below. Transcriptional regulatory elements from the 5' untranslated region of the isolated clone, and other stability, processing, transcription, translation, and tissue specificity determining regions from the 3' and 5' untranslated regions of the isolated gene are thereby obtained.

This invention provides an isolated nucleic acid molecule which has been so mutated as to be incapable of encoding a molecule having normal human $\alpha_1$ adrenergic receptor activity, and not expressing native human $\alpha_1$ adrenergic receptor. An example of a mutated nucleic acid molecule provided by this invention is an isolated nucleic acid molecule which has an in-frame stop codon inserted into the coding sequence such that the transcribed RNA is not translated into protein.

This invention provides a cDNA molecule encoding a human $\alpha_{1a}$ adrenergic receptor, wherein the cDNA molecule has a coding sequence substantially the same as the coding sequence shown in FIGS. 1A–1I. This invention also provides a cDNA molecule encoding a human $\alpha_{1b}$ adrenergic receptor, wherein the cDNA molecule has a coding sequence substantially the same as the coding sequence shown in FIGS. 2A–2H. This invention also provides a cDNA molecule encoding a human $\alpha_{1c}$ adrenergic receptor, wherein the cDNA molecule has a coding sequence substantially the same as the coding sequence shown in FIGS. 3A–3G. These molecules and their equivalents were obtained by the means further described below.

This invention provides an isolated protein which is a human $\alpha_1$ adrenergic receptor. In one embodiment of this invention, the protein is a human $\alpha_{1a}$ adrenergic receptor having an amino acid sequence substantially similar to the amino acid sequence shown in FIGS. 1A–1H. In another embodiment of this invention, the protein is a human $\alpha_{1b}$ adrenergic receptor having an amino acid sequence substantially similar to the amino acid sequence shown in FIGS. 2A–2H. In another embodiment of this invention, the protein is a human $\alpha_{1c}$ adrenergic receptor having an amino acid sequence substantially similar to the amino acid sequence shown in FIGS. 3A–3G. As used herein, the term "isolated protein" is intended to encompass a protein molecule free of other cellular components. One means for obtaining an isolated human $\alpha_1$ adrenergic receptor is to express DNA encoding the $\alpha_1$ adrenergic receptor in a suitable host, such as a bacterial, yeast, or mammalian cell, using methods well known to those skilled in the art, and recovering the human $\alpha_1$ adrenergic receptor after it has been expressed in such a host, again using methods well known in the art. The human $\alpha_1$ adrenergic receptor may also be isolated from cells which express it, in particular from cells which have been transfected with the expression vectors described below in more detail.

This invention also provides a vector comprising an isolated nucleic acid molecule such as DNA, RNA, or cDNA, encoding a human $\alpha_{1a}$ receptor. This invention also provides a vector comprising an isolated nucleic acid molecule such as DNA, RNA, or cDNA, encoding a human human $\alpha_{1b}$ adrenergic receptor. This invention also provides a vector comprising an isolated nucleic acid molecule such as DNA, RNA, or cDNA, encoding a human $\alpha_{1c}$ adrenergic receptor. Examples of vectors are viruses such as bacteriophages (such as phage lambda), cosmids, plasmids (such as pUC18, available from Pharmacia, Piscataway, N.J.), and other recombination vectors. Nucleic acid molecules are inserted into vector genomes by methods well known to those skilled in the art. Examples of such plasmids are plasmids comprising cDNA having a coding sequence substantially the same as: the coding sequence shown in FIGS. 1A–1I, 2A–2H, and 3A–3G. Alternatively, to obtain these vectors, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available.

This invention also provides vectors comprising a DNA molecule encoding a human $\alpha_{1a}$, vectors comprising a DNA molecule encoding a human $\alpha_{1b}$ adrenergic receptor and vectors comprising a DNA molecule encoding a human $\alpha_{1c}$ adrenergic receptor adapted for expression in a bacterial cell, a yeast cell, or a mammalian cell which additionally comprise the regulatory elements necessary for expression of the DNA in the bacterial, yeast, or mammalian cells so located relative to the DNA encoding a human $\alpha_1$ adrenergic receptor as to permit expression thereof. DNA having coding sequences substantially the same as the coding sequence shown in FIGS. 1A–1I may be inserted into the vectors to express a human $\alpha_{1a}$ adrenergic receptor. DNA having coding sequences substantially the same as the coding sequence shown in FIGS. 2A–2H may be inserted into the vectors to express a human $\alpha_{1b}$ adrenergic receptor. DNA having coding sequences substantially the same as the coding sequence shown in FIGS. 3A–3G may be inserted into the vectors to express a human $\alpha_{1c}$ adrenergic receptor. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express a human $\alpha_1$ adrenergic receptor. Certain uses for such cells are described in more detail below.

In one embodiment of this invention a plasmid is adapted for expression in a bacterial, yeast, or, in particular, a mammalian cell wherein the plasmid comprises a DNA molecule encoding a human $\alpha_{1a}$ adrenergic receptor, a DNA molecule encoding a human $\alpha_{1b}$ adrenergic receptor or a DNA molecule encoding a human $\alpha_{1c}$ adrenergic receptor and the regulatory elements necessary for expression of the DNA in the bacterial, yeast, or mammalian cell so located relative to the DNA encoding a human $\alpha_1$ adrenergic receptor as to permit expression thereof. Suitable plasmids may include, but are not limited to plasmids adapted for expression in a mammalian cell, e.g., pCEXV-3 derived expression vector. Examples of such plasmids adapted for expression in a mammalian cell are plasmids comprising cDNA having coding sequences substantially the same as the coding sequence shown in FIGS. 1A–1I, 2A–2H, and 3A–3G and the regulatory elements necessary for expression of the DNA in the mammalian cell. These plasmids have been designated pcEXV-$\alpha_{1a}$ deposited under ATCC Accession No. 75319, pcEXV-$\alpha_{1b}$ deposited under ATCC Accession No. 75318, and pcEXV-$\alpha_{1c}$ deposited under ATCC Accession No. 75317, respectively. Those skilled in the art will readily appreciate that numerous plasmids adapted for expression in a mammalian cell which comprise DNA encoding human $\alpha_1$ adrenergic receptors and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

The deposits discussed supra were made pursuant to, and in satisfaction of, the provisions of the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA molecule encoding a human $\alpha_1$ adrenergic receptor, such as a mammalian cell comprising a plasmid adapted for expression in a mammalian cell, which comprises a DNA molecule encoding a human $\alpha_1$ adrenergic receptor and the regulatory elements necessary for expression of the DNA in the mammalian cell so located relative to the DNA encoding a human $\alpha_1$ adrenergic receptor as to permit expression thereof. Numerous mammalian cells may be used as hosts, including, but not limited to, the mouse fibroblast cell NIH3T3, CHO cells, HeLa cells, Ltk⁻ cells, human embryonic kidney cells, Cos cells, etc. Expression plasmids such as that described supra may be used to transfect mammalian cells by methods well known in the art such as calcium phosphate precipitation, or DNA encoding these human $\alpha_1$ adrenergic receptors may be otherwise introduced into mammalian cells, e.g., by microinjection, to obtain mammalian cells which comprise DNA, e.g., cDNA or a plasmid, encoding a human $\alpha_1$ adrenergic receptor.

This invention provides a nucleic acid probe comprising a nucleic acid molecule of at least 15 nucleotides capable of specifically hybridizing with a sequence included within the sequence of a nucleic acid molecule encoding a human $\alpha_{1a}$ adrenergic receptor, for example with a coding sequence included within the sequence shown in FIGS. 1A–1I. This invention also provides a nucleic acid probe comprising a nucleic acid molecule of at least 15 nucleotides capable of specifically hybridizing with a sequence included within the sequence of a nucleic acid molecule encoding a human $\alpha_{1b}$ adrenergic receptor, for example with a coding sequence included within the sequence shown in FIGS. 2A–2H. This invention also provides a nucleic acid probe comprising a nucleic acid molecule of at least 15 nucleotides capable of specifically hybridizing with a sequence included within the sequence of a nucleic acid molecule encoding a human $\alpha_{1c}$ adrenergic receptor, for example with a coding sequence included within the sequence shown in FIGS. 3A–3G. As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding a human $\alpha_1$ adrenergic receptor is useful as a diagnostic test for any disease process in which levels of expression of the corresponding human $\alpha_{1a}$, $\alpha_{1b}$ or $\alpha_{1c}$ adrenergic receptor are altered. DNA probe molecules are produced by insertion of a DNA molecule which encodes a human $\alpha_{1a}$, human $\alpha_{1b}$ or human $\alpha_{1c}$ adrenergic receptor or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. Examples of such DNA molecules are shown in FIGS. 1A–1I, 2A–2H, and 3A–3G. The probes are useful for "in situ" hybridization or in order to identify tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a human $\alpha_{1a}$ adrenergic receptor, or complementary to the sequence of a DNA molecule which encodes a human $\alpha_{1b}$ adrenergic receptor or complementary to the sequence of a DNA molecule which encodes a human $\alpha_{1c}$ adrenergic receptor are useful as probes for these genes, for their associated mRNA, or for the isolation of related genes by homology screening of genomic or cDNA libraries, or by the use of amplification techniques such as the Polymerase Chain Reaction.

This invention also provides a method for detecting expression of a human $\alpha_{1a}$ adrenergic receptor on the surface of a cell by detecting the presence of mRNA coding for a human $\alpha_{1a}$ adrenergic receptor. This invention also provides a method for detecting expression of a human $\alpha_{1b}$ adrenergic receptor on the surface of a cell by detecting the presence of mRNA coding for a human $\alpha_{1b}$ adrenergic receptor. This invention also provides a method for detecting expression of a human $\alpha_{1c}$ adrenergic receptor on the surface of a cell by detecting the presence of mRNA coding for a human $\alpha_{1c}$ adrenergic receptor. These methods comprise obtaining total mRNA from the cell using methods well known in the art and contacting the mRNA so obtained with a nucleic acid probe as described hereinabove, under hybridizing conditions, detecting the presence of mRNA hybridized to the probe, and thereby detecting the expression of a specific human $\alpha_1$ adrenergic receptor by the cell. Hybridization of probes to target nucleic acid molecules such as mRNA molecules employs techniques well known in the art. However, in one embodiment of this invention, nucleic acids are extracted by precipitation from lysed cells and the mRNA is isolated from the extract using a column which binds the poly-A tails of the mRNA molecules (Maniatis, T. et al., Molecular Cloning; Cold Spring Harbor Laboratory, pp.197–98 (1982)). The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of specifically binding with any sequences of an mRNA molecule which encodes a human $\alpha_{1a}$ adrenergic receptor so as to prevent translation of the human $\alpha_{1a}$ adrenergic receptor. This invention also provides an antisense oligonucleotide having a sequence capable of specifically binding with any sequences of an mRNA molecule which encodes a human $\alpha_{1b}$ adrenergic receptor so as to prevent translation of the human $\alpha_{1b}$ adrenergic receptor. This invention also provides an antisense oligonucleotide having a sequence capable of specifically binding with any sequences of an mRNA molecule which encodes a human $\alpha_{1c}$ adrenergic receptor so as to prevent translation of the human $\alpha_{1c}$ adrenergic receptor. As used herein, the phrase "specifically binding" means the ability of an antisense oligonucleotide to recognize a nucleic acid sequence complementary to its own and to form double-helical segments through hydrogen bonding between complementary base pairs. The antisense oligonucleotide may have a sequence capable of specifically binding with any sequences of the cDNA molecules whose sequences are shown in FIGS. 1A–1I, 2A–2H or 3A–3G. A particular example of an antisense oligonucleotide is an antisense oligonucleotide comprising chemical analogues of nucleotides which are known to one of skill in the art.

This invention also provides a pharmaceutical composition comprising an effective amount of the oligonucleotide described above effective to reduce expression of a human $\alpha_{1a}$ adrenergic receptor, by passing through a cell membrane and specifically binding with mRNA encoding the human $\alpha_{1a}$ adrenergic receptor in the cell so as to prevent its translation and a pharmaceutically acceptable hydrophobic carrier capable of passing through a cell membrane. This invention also provides a pharmaceutical composition comprising an effective amount of the oligonucleotide described above effective to reduce expression of a human $\alpha_{1b}$ adrenergic receptor in the cell so as to prevent its translation and a pharmaceutically acceptable hydrophobic carrier capable of passing through a cell membrane. This invention further provides a pharmaceutical composition comprising an effective amount of the oligonucleotide described above effective to reduce expression of a human $\alpha_{1c}$ adrenergic receptor in the cell so as to prevent its translation and a pharmaceutically acceptable hydrophobic carrier capable of passing through a cell membrane. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The oligonucleotide may be coupled to a substance which inactivates mRNA, such as a ribozyme. The pharmaceutically acceptable hydrophobic carrier capable of passing through cell membranes may also comprise a structure which binds to a transporter specific for a selected cell type and is thereby taken up by cells of the selected cell type. The structure may be part of a protein known to bind a cell-type specific transporter, for example an insulin molecule, which would target pancreatic cells. DNA molecules having coding sequences substantially the same as the coding sequence shown in FIGS. 1A–1I, 2A–2H, or 3A–3G may be used as the oligonucleotides of the pharmaceutical composition.

This invention also provides a method of treating abnormalities which are alleviated by reduction of expression of a human $\alpha_1$ adrenergic receptor. This method comprises administering to a subject an effective amount of the pharmaceutical composition described above effective to reduce expression of the human $\alpha_1$ adrenergic receptor by the subject. This invention further provides a method of treating an abnormal condition related to $\alpha_1$ adrenergic receptor activity which comprises administering to a subject an amount of the pharmaceutical composition described above effective to reduce expression of the human $\alpha_1$ adrenergic receptor by the subject. Examples of such an abnormal condition include but are not limited to benign prostatic hypertrophy, coronary heart disease, hypertension, urinary retention, insulin resistance, atherosclerosis, sympathetic dystrophy syndrome, glaucoma, cardiac arrythymias erectile dysfunction, and Renaud's syndrome.

Antisense oligonucleotide drugs inhibit translation of mRNA encoding the human $\alpha 1a$, human $\alpha 1b$ or human $\alpha 1c$ adrenergic receptors. Synthetic antisense oligonucleotides, or other antisense chemical structures are designed to bind to mRNA encoding the human $\alpha 1a$ adrenergic receptor, to mRNA encoding the human $\alpha 1b$ adrenergic receptor or to mRNA encoding the human $\alpha 1c$ adrenergic receptor and inhibit translation of mRNA and are useful as drugs to inhibit expression of the human $\alpha_{1a}$ adrenergic receptor, the human $\alpha_{1b}$ adrenergic receptor or the human $\alpha_{1c}$ adrenergic receptor in patients. This invention provides a means to therapeutically alter levels of expression of the human $\alpha_{1a}$ adrenergic receptor, the human $\alpha_{1b}$ adrenergic receptor or the human $\alpha_{1c}$ adrenergic receptor by the use of a synthetic antisense oligonucleotide drug (SAOD) which inhibits translation of mRNA encoding these $\alpha_1$ adrenergic receptors. Synthetic antisense oligonucleotides, or other antisense chemical structures designed to recognize and selectively bind to mRNA, are constructed to be complementary to portions of the nucleotide sequences shown in FIGS. 1A–1I, 2A–2H, or 3A–3G of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical nd chemical properties of the SAOD which render it capable of passing through cell membranes (e.g., by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which bind and take up the SAOD only within certain selected cell populations. For example, the SAOD may be designed to bind to a transporter found only in a certain cell type, as discussed above. The SAOD is also designed to recognize and selectively bind to the target mRNA sequence, which may correspond to a sequence contained within the sequences shown in FIGS. 1A–1I, 2A–2H, or 3A–3G by virtue of complementary base pairing to the mRNA. Finally, the SAOD is designed to inactivate the target mRNA sequence by any of three mechanisms: 2) by binding to the target mRNA and thus inducing degradation of the mRNA by intrinsic cellular mechanisms such as mRNA target by interfering with the binding of translation-regulating factors or of other chemical structures, such as ribozyme sequences or reactive chemical groups, which either degrade or chemically modify the target mRNA. Synthetic antisense oligonucleotide drugs have been shown to be capable of the properties described above when directed against mRNA targets (J. S. Cohen, Trends in Pharm. Sci 10, 435 (1989); H. M. Weintraub, Sci. AM. January (1990) p. 40). In addition, coupling of ribozymes to antisense oligonucleotides is a promising strategy for inactivating target mRNA (N. Sarver et al., Science 247, 1222 (1990)). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce human $\alpha_1$ adrenergic receptor expression in particular target cells of a patient, in any clinical condition which may benefit from reduced expression of a specific human $\alpha_1$ adrenergic receptor.

This invention provides an antibody directed to a human $\alpha_{1a}$ adrenergic receptor. This antibody may comprise, for example, a monoclonal antibody directed to an epitope of a human $\alpha_{1a}$ adrenergic receptor present on the surface of a cell, the epitope having an amino acid sequence substantially the same as an amino acid sequence for a cell surface epitope of the human $\alpha_{1a}$ adrenergic receptor included in the amino acid sequence shown in FIGS. 1A–1I. This invention also provides an antibody directed to a human $\alpha_{1b}$ adrenergic receptor. This antibody may comprise, for example, a monoclonal antibody directed to an epitope of a human $\alpha_{1b}$ adrenergic receptor present on the surface of a cell, the epitope having an amino acid sequence substantially the same as an amino acid sequence for a cell surface epitope of the human $\alpha_{1b}$ adrenergic receptor included in the amino acid sequence shown in FIGS. 2A–2H. This invention also provides an antibody directed to a human $\alpha_{1c}$ adrenergic receptor. This antibody may comprise, for example, a monoclonal antibody directed to an epitope of a human $\alpha 1c$ adrenergic receptor present on the surface of a cell, the epitope having an amino acid sequence substantially the same as an amino acid sequence for a cell surface epitope of the human $\alpha 1c$ adrenergic receptor included in the amino acid sequence shown in FIGS. 3A–3G. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIGS. 1A–1I will bind to a surface epitope of the human $\alpha 1a$ adrenergic receptor, antibodies to the hydrophilic amino acid sequences shown in FIGS. 2A–2H will bind to a surface epitope of a human $\alpha 1b$ adrenergic receptor, and antibodies to the hydrophilic amino acid sequences shown in FIGS. 3A–3G will bind to a surface epitope of a human $\alpha 1c$ adrenergic receptor as described. Antibodies directed to human $\alpha 1$ adrenergic receptors may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or Ltk$^-$ cells may be used as immunogens to raise such an antibody. Alternatively, synthetic peptides may be prepared using commercially available machines and the amino acid sequence shown in FIGS. 1A–1I, 2A–2H, and 3A–3G. As a still further alternative DNA, such as a cDNA or a fragment thereof, may be cloned and expressed and the resulting polypeptide recovered and used as an immunogen. These antibodies are useful to detect the presence of human $\alpha 1$ adrenergic receptors encoded by the isolated DNA, or to inhibit the function of $\alpha 1$ adrenergic receptors in living animals, in humans, or in biological tissues or fluids isolated from animals or humans.

This invention provides a pharmaceutical composition which comprises an effective amount of an antibody directed to an epitope of a human $\alpha_{1a}$ adrenergic receptor and a pharmaceutically acceptable carrier. A monoclonal antibody directed to an epitope of a human $\alpha_{1a}$ adrenergic receptor present on the surface of a cell which has an amino acid sequence substantially the same as an amino acid sequence for a cell surface epitope of the human $\alpha_{1a}$ adrenergic receptor present on the surface of a cell which has an amino acid sequence substantially the same as an amino acid sequence for a cell surface epitope of the human $\alpha_{1a}$ adrenergic receptor included in the amino acid sequence shown in FIGS. 1A–1I is useful for this purpose. This invention also provides a pharmaceutical composition which comprises an effective amount of an antibody directed to an epitope of a human $\alpha_{1b}$ adrenergic receptor, effective to block binding of naturally occurring substrates to the human $\alpha_{1b}$ adrenergic receptor and a pharmaceutically acceptable carrier. A monoclonal antibody directed to an epitope of a human $\alpha_{1b}$ adrenergic receptor present on the surface of a cell which has an amino acid sequence substantially the same as an amino acid sequence for a cell surface epitope of the human $\alpha_{1b}$ adrenergic receptor included in the amino acid sequence shown in FIGS. 2A–2H is useful for this purpose. This invention provides a pharmaceutical composition which comprises an effective amount of an antibody directed to an epitope of a human $\alpha_{1c}$ adrenergic receptor effective to block binding of naturally occurring substrates to the human $\alpha_{1c}$ adrenergic receptor and a pharmaceutically acceptable carrier. A monoclonal antibody directed to an epitope of a human $\alpha_{1c}$ adrenergic receptor present on the surface of the cell which has an amino acid sequence substantially the same as an amino acid sequence for a cell surface epitope of the human $\alpha_{1c}$ adrenergic receptor included in the amino acid sequence shown in FIGS. 3A–3G is useful for this purpose.

This invention also provides a method of treating abnormalities in a subject which are alleviated by reduction of expression of a specific human $\alpha_1$ adrenergic receptor. The method comprises administering to the subject an effective amount of the pharmaceutical composition described above effective to block binding of naturally occurring substrates to the human $\alpha_1$ adrenergic receptor and thereby alleviate abnormalities resulting from overexpression of the human $\alpha_1$ adrenergic receptor. Binding of the antibody to the human $\alpha_1$ adrenergic receptor from functioning, thereby neutralizing the effects of overexpression. The monoclonal antibodies described above are useful for this purpose. This invention additionally provides a method of treating an abnormal condition related to an excess of a specific human $\alpha_1$ adrenergic receptor activity which comprises administering to a subject an amount of the pharmaceutical composition described above effective to block binding of naturally occurring substrates to the human $\alpha 1$ adrenergic receptor and thereby alleviate the abnormal condition. Examples of such an abnormal condition include but are not limited to benign prostatic hypertrophy, coronary heart disease, insulin resistance, atherosclerosis, sympathetic dystrophy syndrome, glaucoma, cardiac arrythymias, hypertension, urinary retention, erectile dysfunction, and Renaud's syndrome.

This invention provides methods of detecting the presence of a specific human $\alpha 1$ adrenergic receptor on the surface of a cell which comprises contacting the cell with an antibody directed to a specific human $\alpha 1$ adrenergic receptor, under conditions permitting binding of the antibody to the human $\alpha 1$ adrenergic receptor, under conditions permitting binding of the antibody to the human $\alpha 1$ adrenergic receptor, detecting the presence of any antibody bound to the $\alpha 1$ adrenergic receptor, and thereby the presence of the specific human $\alpha 1$ adrenergic receptor on the surface of the cell. Such methods are useful for determining whether a given cell is defective in expression of a specific human $\alpha 1$ adrenergic receptor. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal comprising DNA encoding DNA encoding a human $\alpha_{1a}$ adrenergic receptor. This invention also provides a transgenic nonhuman mammal comprising DNA encoding a human $\alpha_{1b}$ adrenergic receptor. This invention also provides a transgenic nonhuman mammal comprising DNA encoding a human $\alpha_{1c}$ adrenergic receptor.

This invention also provides a transgenic nonhuman mammal comprising DNA encoding a human $\alpha_{1a}$ adrenergic receptor so mutated as to be incapable of normal human $\alpha_{1a}$ adrenergic receptor activity, and not expressing native human $\alpha 1a$ adrenergic receptor activity, and not expressing native human $\alpha 1a$ adrenergic receptor. This invention also provides a transgenic nonhuman mammal comprising DNA encoding a human $\alpha_{1b}$ adrenergic receptor so mutated as to be incapable of normal human $\alpha 1b$ adrenergic receptor activity, and not expressing native human $\alpha 1b$ adrenergic receptor. This invention also provides a transgenic nonhuman mammal comprising DNA encoding a human $\alpha_{1c}$ adrenergic receptor so mutated as to be incapable of normal human $\alpha 1c$ adrenergic receptor activity, and not expressing native human $\alpha 1c$ adrenergic receptor.

This invention provides a transgenic non-human animal whose genome comprises DNA encoding a human $\alpha_{1a}$ adrenergic receptor so placed as to be transcribed into antisense mRNA which is complementary to mRNA encoding a human $\alpha_{1a}$ adrenergic receptor thereby reducing its translation. This invention also provides a transgenic non-human mammal whose genome comprises DNA encoding a human $\alpha_{1b}$ adrenergic receptor so placed as to be transcribed into antisense mRNA which is complementary to mRNA encoding the human $\alpha_{1b}$ adrenergic receptor and which hybridizes to mRNA encoding a human $\alpha_{1b}$ adrenergic receptor thereby reducing its translation. This invention provides a transgenic non-human animal whose genome comprises DNA encoding a human $\alpha_{1c}$ adrenergic receptor so placed as to be transcribed into antisense mRNA which is complementary to mRNA encoding a human $\alpha_{1c}$ adrenergic receptor and which hybridizes to mRNA encoding the human $\alpha_{1c}$ adrenergic receptor thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequences shown in FIGS. 1A–1I, 2A–2H, or 3A–3G. An example of a transgenic animal is a transgenic mouse. Examples of tissue specificity-determining regions are the metallothionein promoter (Low, M. J., Lechan, R. M., Hammer, R. E. et al. Science 231:1002–1004 (1986) and the L7 promoter (Oberdick, J., Smeyne, R. J., Mann, J. R., Jackson, S. and Morgan, J. I. Science 248:223–226 (1990)).

Animal model systems which elucidate the physiological and behavioral roles of human $\alpha_1$ adrenergic receptors are produced by creating transgenic animals in which the increased or decreased, or the amino acid sequence of the expressed $\alpha_1$ adrenergic receptor is altered, by a variety of techniques. Examples of these techniques include, but are not limited to: 1) Insertion of normal or mutant versions of DNA encoding a human $\alpha_1$ adrenergic receptor or homologous animal versions of these genes, by microinjection, retroviral infection or other means well known to those skilled in the art, into appropriate fertilized embryos in order to produce a transgenic animal (Hogan B et al., Manipulating the Mouse Embryo, A Laboratory Manual, Cold Spring Harbor Laboratory (1986)) or, 2) Homologous recombination (Capecchi M. R. Science 244:1288–1292 (1989); Zimmer, A. and Gruss, P. Nature 338:150–153 (1989)) of mutant or normal, human or animal version of the genes encoding $\alpha 1$ adrenergic receptors with the native gene locus in transgenic animals to alter the regulation of expression or the structure $\alpha 1$ of these $\alpha 1$ adrenergic receptors. The technique of homologous $\alpha_1$ adrenergic receptors. The technique of homologous recombination is well known in the art. It replaces the native gene with the inserted gene and so is useful for producing an animal that cannot express native $\alpha_1$ adrenergic receptor but does express, for example an inserted mutant human $\alpha_1$ adrenergic receptor, which has replaced the native $\alpha_1$ adrenergic receptor in the animal's genome by recombination, resulting in underexpression of the $\alpha_1$ adrenergic receptor. Microinjection adds genes to the genome, but does not remove them, and so is useful for producing an animal which expresses its own and added $\alpha_1$ adrenergic receptors, resulting in overexpression of the $\alpha_1$ adrenergic receptor.

One means available for producing a transgenic animal, with a mouse as an example, is as follows: Female mice are mated, and the resulting fertilized eggs are dissected out of their oviducts. The eggs are stored in an appropriate medium such as M2 medium (Hogan B et al., Manipulating the Mouse Embryo, A Laboratory Manual, Cold Spring Harbor Laboratory (1986)). DNA or cDNA encoding a human $\alpha_1$ adrenergic receptor is purified from a vector (such as plasmids pCEXV-$\alpha_{1b}$, or pCEXV-$\alpha_{1c}$ described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of $\alpha_1$ adrenergic-specific drugs is to activate or to inhibit the $\alpha_1$ adrenergic receptor, the transgenic animal model systems described above are useful for testing the biological activity of drugs directed against specific human $\alpha_1$ adrenergic receptors even before such drugs become available. These animal model systems are useful for predicting or evaluating possible therapeutic applications of drugs which activate or inhibit these human $\alpha_1$ adrenergic receptors by inducing or inhibiting expression of the native or transgene and thus increasing or decreasing expression of normal or mutant human $\alpha_1$ adrenergic receptor in the living animal. Thus, a model system is produced in which the biological activity of drugs directed against these human $\alpha_1$ adrenergic receptors are evaluated before such drugs become available. The transgenic animals which over or under produce a specific human $\alpha_1$ adrenergic over or under produce a specific human $\alpha_1$ adrenergic over or under produce a specific human $\alpha_1$ adrenergic receptor indicate by their physiological state whether over or under production of the human $\alpha_1$ adrenergic receptor is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less human $\alpha_1$ adrenergic receptor by the affected cells, leading eventually to underexpression. Therefore, an animal which underexpresses human $\alpha_1$ adrenergic receptor is useful as a test system to investigate whether the actions of such drugs which result in under expression are in fact therapeutic. Another use is that if overexpression is found to lead abnormalities, then a drug which down-regulates or acts as an antagonist to the human $\alpha_1$ adrenergic receptor is indicated as worth developing, and if a promising therapeutic application is uncovered by these animal model systems, activation or inhibition of the specific human $\alpha_1$ adrenergic receptor or antagonist drugs directed against these human $\alpha_1$ adrenergic receptors or by any method which increases or decreases the expression of these $\alpha_1$ adrenergic receptors in man.

Further provided by this invention is a method of determining the physiological effects of expressing varying levels of a human $\alpha_1$ adrenergic receptor which comprises producing a transgenic nonhuman animal whose levels of $\alpha_1$ adrenergic receptor expression are varied by use of an inducible promoter which regulates human $\alpha_1$ adrenergic receptor expression. This invention also provides a method for determining the physiological effects of expressing varying levels of human $\alpha_1$ adrenergic receptors which comprise producing a panel of transgenic nonhuman animals each expressing a different amount of a human $\alpha_1$ adrenergic receptor. Such animals may be produced by introducing different amounts of DNA encoding a human $\alpha_1$ adrenergic receptor into the oocytes from which the transgenic animals are developed.

This invention also provides a method for identifying a substance capable of alleviating abnormalities resulting from overexpression of a human $\alpha_1$ adrenergic receptor comprising administering the substance to a transgenic nonhuman mammal expressing at least one artificially introduced DNA molecule encoding a human $\alpha_1$ adrenergic receptor and determining whether the substance alleviates the physical and behavioral abnormalities displayed by the transgenic nonhuman mammal as a result of overexpression of a human $\alpha_1$ adrenergic receptor. As used herein, the term "substance" means a compound or composition which may be natural, synthetic, or a product derived from screening. Examples of DNA molecules are DNA or cDNA molecules having a coding sequence substantially the same as the coding sequences shown in FIGS. 1A–1I, 2A–2H, or 3A–3G.

This invention provides a pharmaceutical composition comprising an amount of the substance described supra effective to alleviate the abnormalities resulting from overexpression of a human $\alpha_{1a}$ adrenergic receptor and a pharmaceutically acceptable carrier. This invention provides a pharmaceutical composition comprising an amount of the substance described supra effective to alleviate the abnormalities resulting from overexpression of a human $\alpha_{1b}$ adrenergic receptor and a pharmaceutically acceptable carrier. This invention also provides a pharmaceutical composition comprising an amount of the substance described supra effective to alleviate the abnormalities resulting from overexpression of a human $\alpha_{1c}$ adrenergic receptor and a pharmaceutically acceptable carrier.

This invention further provides a method for treating the abnormalities resulting from overexpression of a human $\alpha_1$ adrenergic receptor which comprises administering to a subject an amount of the pharmaceutical composition described above effective to alleviate the abnormalities resulting from overexpression of the human $\alpha_1$ adrenergic receptor.

This invention provides a method for identifying a substance capable of alleviating the abnormalities resulting from underexpression of a human $\alpha_1$ adrenergic receptor comprising administering the substance to the transgenic nonhuman mammal described above which expresses only a nonfunctional human $\alpha_1$ adrenergic receptor and determining whether the substance alleviates the physical and behavioral abnormalities displayed by the transgenic nonhuman mammal as a result of underexpression of the human $\alpha_1$ adrenergic receptor.

This invention also provides a pharmaceutical composition comprising an amount of a substance effective to alleviate abnormalities resulting from underexpression of a human $\alpha_1$ adrenergic receptor and a pharmaceutically acceptable carrier.

This invention also provides a method for treating the abnormalities resulting from underexpression of a human $\alpha_1$ adrenergic receptor which comprises administering to a subject an amount of the pharmaceutical composition described above effective to alleviate the abnormalities resulting from underexpression of a human $\alpha_1$ adrenergic receptor.

This invention provides a method for diagnosing a predisposition to a disorder associated with the expression of a specific human $\alpha_1$ adrenergic receptor allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a human $\alpha_1$ adrenergic receptor and labelled bands which have hybridized to the DNA encoding a human $\alpha^1$ adrenergic receptor labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human $\alpha_1$ adrenergic receptor allele.

This invention provides a method of preparing an isolated human $\alpha_1$ adrenergic receptor which comprises inducing cells to express the human $\alpha_1$ adrenergic receptor, recovering the $\alpha_1$ adrenergic receptor from the resulting cells, and purifying the $\alpha_1$ adrenergic receptor so recovered. An example of an isolated human $\alpha_{1a}$ adrenergic receptor is an isolated protein having substantially the same amino acid sequence as the amino acid sequence shown in FIGS. 1A–1I. An example of an isolated human $\alpha_{1b}$ adrenergic receptor is an isolated protein having substantially the same amino acid sequence as the amino acid sequence shown in FIGS. 1A–1I. An example of an isolated human $\alpha_{1b}$ adrenergic receptor is an isolated protein having substantially the same amino acid sequence shown in FIG. 2A–2H. An example of an isolated human $\alpha_{1c}$ adrenergic receptor is an isolated protein having substantially the same amino acid sequence shown in FIG. 3A–3G. For example, cells can be induced to express human $\alpha_1$ adrenergic receptor by exposure to substances such as hormones. The cells can then be homogenized and the human $\alpha_1$ adrenergic receptor isolated from the homogenate using an affinity column comprising, for example, epinephrine, norepinephrine, or another substance which is known to bind to the human $\alpha_1$ adrenergic receptor. The resulting fractions can then be purified by contacting them with an ion exchange column, and determining which fraction contains human $\alpha_1$ adrenergic receptor activity or binds anti-human $\alpha_1$ adrenergic receptor activity or binds anti-human $\alpha 1$ adrenergic receptor antibodies.

This invention provides a method of preparing the isolated human $\alpha_{1a}$ adrenergic receptor which comprises inserting nucleic acid encoding the human $\alpha_{1a}$ adrenergic receptor in a suitable vector, inserting the resulting vector in a suitable host cell, recovering the $\alpha_{1a}$ adrenergic receptor produced by the resulting cell, and purifying the $\alpha_{1a}$ adrenergic receptor so recovered. An example of an isolated human $\alpha_{1a}$ adrenergic receptor is an isolated protein having substantially the same amino acid sequence as the amino acid sequence shown in FIGS. 1A–1I. This invention also provides a method of preparing the isolated human $\alpha_{1b}$ adrenergic receptor which comprises inserting nucleic acid encoding the human $\alpha_{1b}$ adrenergic receptor in a suitable vector, inserting the resulting vector in a suitable host, recovering the $\alpha_{1b}$ adrenergic receptor produced by the resulting cell, and purifying the $\alpha_{1c}$ adrenergic receptor so recovered. These methods for preparing human $\alpha_1$ adrenergic receptor uses recombinant DNA technology methods well known in the art. For example, isolated nucleic acid encoding a human $\alpha_1$ adrenergic receptor is inserted in a suitable vector, such as an expression vector. A suitable host cell, such as a bacterial cell, or a eukaryotic cell such as a yeast cell is transfected with the vector. The human $\alpha_1$ adrenergic receptor is isolated from the culture medium by affinity purification or by chromatography or by other methods well known in the art.

This invention provides a method of determining whether a ligand not known to be capable of binding to a human $\alpha_1$ adrenergic receptor can bind to a human $\alpha_1$ adrenergic receptor, which comprises contacting a mammalian cell comprising a plasmid adapted for expression in a mammalian cell which further comprises a DNA molecule which expresses a human $\alpha_1$ adrenergic receptor on the cell surface with the ligand under conditions permitting binding of ligands known to bind to the human $\alpha_1$ adrenergic receptor, detecting the presence of any ligand bound to the human $\alpha_1$ adrenergic receptor. The DNA in the cell may have a coding sequence substantially the same as the coding sequences shown in FIGS. 1A–1I, 2A–2H, or 3A–3G, preferably, the mammalian cell is nonneuronal in origin. An example of a nonneuronal mammalian cell is a Cos7 cell. The preferred method for determining whether a ligand is capable of binding to the human $\alpha_1$ adrenergic receptor comprises contacting a transfected nonneuronal mammalian cell (i.e. a cell that does not naturally express any type of human $\alpha_1$ adrenergic receptor, thus will only express such human $\alpha_1$ adrenergic receptor if it is transfected into the cell) expressing a human $\alpha_1$ adrenergic receptor on it surface, or contacting a membrane preparation derived from such a transfected cell, with the ligand under conditions which are known to prevail, and thus be associated with in vivo binding of the substrates to a human $\alpha_1$ adrenergic receptor, detecting the presence of any of the ligand being tested bound to the human $\alpha_1$ adrenergic receptor on the surface of the cell, and thereby determining whether the ligand binds to the human $\alpha_1$ adrenergic receptor. This response system is obtained by transfection of isolated DNA into a suitable host cell. Such a host system might be isolated from pre-existing cell lines, or can be generated by inserting appropriate components into existing cell lines. Such a transfection system provides a complete response system for investigation or assay of the functional activity of human $\alpha_1$ adrenergic receptors with ligands as described above. Transfection systems are useful as living cell cultures for competitive binding assays between known or candidate drugs and substrates which bind to the human $\alpha_1$ adrenergic receptor and which are labeled by radioactive, spectroscopic or other reagents. Membrane preparations containing the transporter isolated from transfected cells are also useful for these competitive binding assays. A transfection system constitutes a "drug discovery system" useful for the identification of natural or synthetic compounds with potential for drug development that can be further modified or used directly as therapeutic compounds to activate or inhibit the natural functions of a specific human $\alpha_1$ adrenergic receptor. The transfection system is also useful for determining the affinity and efficacy of known drugs at human $\alpha_1$ adrenergic receptor binding sites.

This invention provides a method for identifying a ligand which interacts with, and activates or blocks the activation of, a human $\alpha_1$ adrenergic receptor on the surface of the cell, which comprises contacting a mammalian cell which comprises a plasmid adapted for expression in a mammalian cell which further comprises a DNA molecule which expresses a human $\alpha_1$ adrenergic receptor on the cell surface with the ligand, determining whether the ligand activates or blocks the activation of the receptor using a bioassay such as a second messenger assays, and thereby identifying a ligand which interacts with, and activates or blocks the activation of, a human $\alpha_1$ adrenergic receptor.

This invention provides functional assays for identifying ligands and drugs which bind to and activate or inhibit a specific human α1 adrenergic receptor activity.

This invention provides a method for identifying a ligand which is capable of binding to and activating or inhibiting a human $\alpha_1$ adrenergic receptor, which comprises contacting a mammalian cell, wherein the membrane lipids have been labelled by prior incubation with a labelled myo-inositol phosphate molecule, the mammalian cell comprising a plasmid adapted for expression in a mammalian cell which further comprises a DNA molecule which expresses a human $\alpha_1$ adrenergic receptor with the ligand and identifying an inositol phosphate metabolite released from the membrane lipid as a result of ligand binding to and activating an a adrenergic receptor.

This invention provides method for identifying a ligand that is capable of binding to and activating or inhibiting a human $\alpha_1$ adrenergic receptor, where in the binding of ligand to the adrenergic receptor results in a physiological response, which comprises contacting a mammalian cell which further comprises a DNA molecule which expresses a human $\alpha_1$ adrenergic receptor with a calcium sensitive fluorescent indicator, removing the indicator that has not been taken up by the cell, contacting the cells with the ligand and identifying an increase or decrease in intracellular $Ca^{+2}$ as a result of ligand binding to and activating receptors.

Transformed mammalian cells for identifying the ligands and drugs that affect the functional properties of the human α adrenergic receptor include 292-α1a-10, C-α1b-6 and C-α1c-7.

This invention also provides a method of screening drugs to identify drugs which interact with, and bind to, a human $\alpha_1$ adrenergic receptor on the surface of a cell, which comprises contacting a mammalian cell which comprises a plasmid adapted for expression in a mammalian cell which further comprises a DNA molecule which expresses a human $\alpha_1$ adrenergic receptor on the cell surface with a plurality of drugs, determining those drugs which bind to the human $\alpha_1$ adrenergic receptor expressed on the cell surface of the mammalian cell, and thereby identifying drugs which interact with, and bind to, the human $\alpha_1$ adrenergic receptor. Various methods of detection may be employed. The drugs may be "labeled" by association with a detectable marker substance (e.g., radiolabel or a non-isotopic label such as biotin). The DNA in the cell may have a coding sequence substantially the same as the coding sequences shown in FIGS. 1A–1I, 2A–2H or 3A–3G. Preferably, the mammalian cell is nonneuronal in origin. An example of a nonneuronal mammalian cell is a Cos7 cell. Drug candidates are identified by choosing chemical compounds which bind with high affinity to the human $\alpha_1$ adrenergic receptor expressed on the cell surface in transfected cells, using radioligand binding methods well known in the art, examples of which are shown in the binding assays described herein. Drug candidates are also screened for selectivity by identifying compounds which bind with high affinity to one particular human $\alpha_1$ adrenergic receptor subtype but do not bind with high affinity to any other human $\alpha_1$ adrenergic receptor subtype or to any other known receptor site. Because selective, high affinity compounds interact primarily with the target human $\alpha_1$ adrenergic site after administration to the patient, the chances of producing a drug with unwanted side effects are minimized by this approach. This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

This invention also provides a method for treating an abnormal condition related to an excess of activity of a human $\alpha_1$ adrenergic receptor subtype, which comprises administering a patient an amount of a pharmaceutical composition described above, effective to reduce $\alpha_1$ adrenergic activity as a result of naturally occurring substrate binding to and activating a specific $\alpha_1$ adrenergic receptor. Examples of such abnormalities related to an excess of activity of a human $\alpha_1$ adrenergic receptor subtype include but are limited to benign prostatic hypertrophy, coronary heart disease, hypertension, urinary retention, insulin resistance, atherosclerosis, sympathetic dystrophy syndrome, glaucoma, cardiac arrythymias erectile dysfunction, and Renaud's syndrome.

This invention also provides a method of treating abnormalities which are alleviated by an increase in the activity of a specific human $\alpha_1$ adrenergic receptor, which comprises administering a patient an amount of a pharmaceutical composition described above, effective to increase the activity of the specific human $\alpha_1$ adrenergic receptor thereby alleviating abnormalities resulting from abnormally low receptor activity. Examples of such abnormalities related to a decrease in the activity of a specific human $\alpha_1$ adrenergic receptor include but are not limited to congestive heart failure, urinary incontinence, nasal congestion and hypotension.

Applicants have identified individual human $\alpha_1$ adrenergic receptor subtypes and have described methods for the identification of pharmacological compounds for therapeutic treatments. Pharmacological compounds which are directed against a specific human adrenergic receptor subtype provide effective new therapies with minimal side effects.

Elucidation of the molecular structures of the neuronal human $\alpha_1$ adrenergic receptors transporters is an important step in the understanding of α-adrenergic neurotransmission. This disclosure reports the isolation, the nucleic acid sequence, and functional expression of DNA clones isolated from human brain which encode human $\alpha_1$ adrenergic receptor. The identification of these human $\alpha_1$ adrenergic receptor will play a pivotal role in elucidating the molecular mechanisms underlying α-adrenergic transmission, and should also aid in the development of novel therapeutic agents.

DNA clones encoding human $\alpha_1$ adrenergic receptor have been isolated from human brain, and their functional properties have been examined in mammalian cells.

This invention identifies for the first time three new human $\alpha_1$ adrenergic receptor, their amino acid sequences, and their human genes. The information and experimental tools provided by this discovery are useful to generate new therapeutic agents, and new therapeutic or diagnostic assays for these new human receptors, their associated mRNA molecules or their associated genomic DNAs. The information and experimental tools provided by this discovery will be useful to generate new therapeutic agents, and new therapeutic or diagnostic assays for these new human receptors, their associates mRNA molecules, or their associated genomic DNAs.

Specifically, this invention relates to the first isolation of human DNA clones encoding three $\alpha_1$-adrenergic receptor. In addition, the human $\alpha_1$ adrenergic receptor have been expressed in mammalian cells by transfecting the cells with the plasmids pCEXV-$\alpha_{1a}$, pcEXV-$\alpha_{1c}$. The pharmacological binding properties of these receptor proteins have been determined, and these binding properties classify these receptor proteins as $\alpha_1$ adrenergic receptor. Mammalian cell lines expressing the human $\alpha_1$ adrenergic receptor on the cell surface have been constructed, thus establishing the first well-defined, cultured cell lines with which to study human $\alpha$1 adrenergic receptor. Examples of transformed mammalian cells, expressing human $\alpha_1$ adrenergic receptor are L-$\alpha$-1a, expressing a human $\alpha$1a adrenergic receptor, L-$\alpha$1b expressing a human $\alpha$1b adrenergic receptor, and L-$\alpha$1c expressing a human $\alpha$1c adrenergic receptor. These cells are suitable for studying the pharmacological properties of the human $\alpha$1 adrenergic receptor and for the screening of ligands and drugs that specifically bind to human $\alpha$1 adrenergic receptor subtypes.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

MATERIALS AND METHODS
Cloning and Sequencing $\alpha$1a: A human lymphocyte genomic library in $\zeta$ dash II ($\approx 1.5 \times 10^6$ total recombinants; Stratagene, LaJolla, Calif.) was screened using a cloned rat PCR fragment (RBNC2) as a probe. RBNC2 was obtained by amplifying randomly primed rat brain cDNA with degenerate primers designed to conserved regions of transmembrane (Tm) regions 2 and 6 of serotonin receptors. The sequence of one PCR product, RBNC2, exhibited strong homology to the $\alpha$1 AR family.

The probe was labeled with [$^{32}$P] by the method of random priming (5) (Prime-It Random Primer kit, Strategene, LaJolla, Calif.). Hybridization was performed at 40° C. in a solution containing 50% formamide, 10% dextran sulfate, 5× SSC (1X SSC is 0.15M sodium choloride, 0.015M sodium citrate), 1× Denhardt's solution (0.02% polyvinylpyrrolidone, 0.02% Ficoll, 0.02% bovine serum albumin), and 200 $\mu g/\mu l$ sonicated salmon sperm DNA. The filters were washed at 50° C. in 0.1× SSC containing 0.5% sodium dodecyl sulfate and exposed at −70° C. to Kodak XAR film in the presence of an intensifying screen. Lambda phage clones hybridizing with the probe were plaque purified and DNA was prepared for Southern blot analysis (22, 17). For subcloning and further Southern blot analysis, DNA was cloned into pUC18 (Pharmacia, Piscataway, N.J.) or pBluescript (Stratagene, LaJolla, Calif.). Nucleotide sequence analysis was accomplished by the Sanger dideoxy nucleotide chain termination method (18) on denatured double-stranded plasmid templates, using Sequenase (US Biochemcial Corp., Cleveland, Ohio), Bst DNA sequencing kit (Bio-Rad Laboratories, Richmond, Calif.), or TaqTrack sequencing kit (Promega Corporation, Madison, Wis.).

In order to isolate a full-length clone, human cDNA libraries were screened by polymerase chain reaction (PCR) with 1 $\mu$M each of specific oligonucleotide primers designed off the isolated genomic clone: from the sense strand (nucleotide 598–626), 5' CACTCAAGTACCCAGCCAT-CATGAC 3' and from the antisense stand (nucleotide 979–1003), 5' CGGAGAGCGAGCTGCGGAAGGTGTG 3' (see FIGS. 1A–1I). The primers were from non-conserved portions of the receptor gene, specifically in the Tm3-Tm3 loop and in the Tm5-Tm6 loop regions for the upstream and downstream primers, respectively. One to 2 $\mu$l of phage DNA from cDNA libraries ($\zeta$ ZapII; Stratagene, LaJolla, Calif.), representing $\approx 10^6$–$10^7$ pfu, were amplified in 10 mM Tris-HCl, pH 8.3, 50 mM KCl, 1.5 mM MgCl$_2$, 0.01% gelatin, 200 $\mu$M each dATP, dCTP, dTTP, 2.5 units of Thermus aquaticus DNA polymerase (Taq polymerase; Perkin-Elmer-Cetus, Norwalk, Conn.). The amplification profile was run for 30 cycles: a 5 min. initial (i.e. 1 cycle denaturation at 95° C., followed by 2 min. at 94° C., 2 min at 68° C., and 3 min at 72° C., with a 3 sec. extension, followed by a final 10 min. extension at 72° C. PCR products were analyzed by ethidium bromide (EtBr) stained agarose gels and any sample exhibiting a band on the EtBr stained gel was considered positive.

A positive library was then plated and screened with overlapping 45-mer oligonucleotide probes, filled-in using [$\alpha$-$^{32}$P]dCTP and [$\alpha$-$^{32}$P]dATP and Klenow fragment of DNA polymerase. This probe was internal to the amplification primers discussed above from the sense strand (nucleotide 890–934), 5' GCAAGGCCTCCGAGGTGGT-GCTGCGCATCCACTGTCGCGGCGCGG 3', and from the anti-sense strand (nucleotide 915–961), 5' TGCCGT-GCGCCCCGTCGGCGCCCGTGGCCGCGC-CGCGACAGTGGATG 3' (see FIGS. 1A–1I). Positive cDNA phage clones were plaque certified and pBluescript recombinant DNAs were excision-rescued from $\zeta$ Zap II using helper phage R408, as described by manufacturer's protocol (Stratagene, LaJolla, Calif.). Insert size was confirmed by restriction enzyme digest analysis and recombinants were sequences as described above.

$\alpha$1b: A human placenta genomic library in $\lambda$ dash II ($\approx 1.5 \times 10^6$ total recombinants; Stratagene, LaJolla, Calif.) was screened using overlapping 45-mer oligonucleotides radiolabeled as described above and directed to the third, fifth and sixth transmembrane regions of serotonin 5HT1D$\beta$ receptor gene. Hybridization and washing conditions were identical to that described for $\alpha$1a above except lower stringency hybridization nd washes were conducted; specifically, hybridization in 25% formamide and washes at 40° C.

Positive-hybridizing $\lambda$ phage clones were plaque-purified, analyzed by Southern blot analysis, subcloned and sequenced, as described above for $\alpha$1a. In order to isolate full-length clones, human cDNA libraries in $\lambda$ Zap II (Strategene, LaJolla, Calif.) were screened by polymerase chain reaction as described above. The upstream and downstream PCR primers used were from the Tm40Tm5 loop and the Tm5-Tm6 loop, respectively: from the sense strand (nucleotide 567–593), 5' CAACGATGACAAGGA GTGCGGGGTCAC 3', and from the antisense strand (nucleotide 822–847), 5' TTTGACAGCTATGGAACTC-CTGGGG 3' (see FIG. 2). PCR, library screen, plaque purification excision-rescue from $\lambda$ Zap II, restriction digestions and sequencing were accomplished as described above for α1a. The internal probe was: from the sense strand (nucleotide 745–789), 5' AAGGAGCTGACCCTGAG-GATCCATTCCAAGAACTTTCACGAGGAC 3', and from the anti-sense strand (nucleotide 770–814), 5' CCTTGGC-CTTGGTACTGCTAAGGGTGTCCTCGTGAAA GTTCT-TGG 3' (see FIGS. 2A–2H).

α1c: A human lymphocyte genomic library in λ dash II (≈1.5×10⁶ total recombinants; Stratagene, LaJolla, Calif.) was screened using overlapping 45-mer oligonucleotides radiolabeled as described for α1a and directed to the third, fifth and sixth transmembrane regions of serotonin 5HT1A receptor gene. Hybridization and washing conditions were identical to that described for α1b. Positive-hybridizing λ phage clones were plaque-purified, analyzed by Southern blot analysis, subcloned and sequenced, as described above for α1a. Identification and isolation of full=length clones by PCR and screening cDNA libraries were accomplished as described for α1b. The upstream and downstream PCR primers used were from the Tm3-Tm4 loop and the Tm5-Tm6 loop, respectively: from the sense strand (nucleotide 403–425), 5' CCAACCATCGTCACCCAGAGGAG 3', and from the antisense strand (nucleotide 775–802), 5' TCTC-CCGGG AGAACTTGAGGAGCCTCAC 3' (see FIGS. 3A–3G). The internal probe was: from the sense strand (nucleotide 711–745), 5' TCCGCATCCATCG-GAAAAACGCCCCGGCAGGAGGC AGCGGGATGG 3', and from the anti-sense strand (nucleotide 726–771), 5' GAAGTGCGTCTTGGTCTTGGCGCT GGCCATC-CCGCTGCCTCCTGCC 3' (see FIGS. 3A–3G). PCR, library screen, plaque purification excision-rescue from λ Zap II, restriction digestions and sequencing were accomplished as described above for α1a.

Expression

α1a: The entire coding region of α1a (1719 bp), including 150 basepairs of 5' untranslated sequence (5' UT) and 300 bp of 3' untranslated sequence (3' UT), was cloned into the BamHI and ClaI sites of the polylinker-modified eukaryotic expression vector pCEXV-3 (13), called EXJ.HR (unpublished data). The construct involved the ligation of partial overlapping human lymphocyte genomic and hippocamppal cDNA clones: 5' sequences were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid α1a/EXJ (expression vector containing the α1a receptor gene) and the plasmid pGCcos3neo (plasmid containing the aminoglycoside transferase gene) into LM(tk⁻), CHO, NIH3T3 cells, and 293 cells using calcium phosphate technique. The cells were grown, in a controlled environment (37° C., 5% CO₂), as monolayers in Dulbecco's modified Eagle's Medium (GIBCO, Grand Island, N.Y.) containing 25 mM glucose and supplemented with 10% bovine calf serum, 100 units/ml penicillin G, and 100 μg/ml streptomycin sulfate. Stable clones were then selected for resistance to the antibiotic G-418 (1 mg/ml) as described previously (26) and membranes were harvested and assayed for their ability to bind [³H]prazosin as described below (see "Radioligand Binding Assays").

α1b: The entire coding region of α1b (1563 bp), including 200 basepairs of 5' untranslated sequence (5' UT) and 600 bp of 3' untranslated sequence (3' UT), was cloned into the EcoRI site of pCEXV-3 eukaryotic expression vector (13). The construct involved ligating the full-length containing EcoRI brainstem cDNA fragment from λ Zap II into the expression vector. Stable cell lines were selected as described above.

α1c: The entire coding region of α1c (1401 bp), including 400 basepairs of 5' untranslated sequence (5' UT) and 200 bp of 3' untranslated sequence (3' UT), was cloned into the KpnI site of the polylinker-modified pCEXV-3-derived (13) eukaryotic expression vector, EXJ.RH (unpublished data). The construct involved ligating three partial overlapping fragments: a 5' 0.6 kb HincII genomic clone, a central 1.8 EcoRI hippocamppal cDNA clone, and a 3' 0.6 kb PstI genomic clone. The hippocamppal cDNA fragment overlaps with the 5' and 3' genomic clones so that the HincII and PstI sites at the 5' and 3' ends of the cDNA clones, respectively, were utilized for ligation. This full-length clone was cloned into the KpnI sites of the fragment, derived from vector (ie pBluescript) and 3' untranslated sequences, respectively. Stable cell lines were selected as described above.

Radioligand Binding Assays

Transfected cells from culture flasks were scraped into 5 ml of 5 mM tris-HCl, 5 mM EDTA, pH 7.5, and lysed by sonication. The cell lysates were centrifuged at 1000 rpm for 5 min at 4° C. The pellet was suspended in 50 mM Tris-HCl, 1 mM MgCl₂, and 0.1% ascorbic acid at pH 7.5. Binding of the α1 antagonist [³H]prazosin (0.5 nM, specific activity 76.2 Ci/mmol) to membrane preparations of LM(tk−) cells was done in a final volume of 0.25 ml and incubated at 37° C. for 20 min. Nonspecific binding was determined in the presence of 10 μM phentolamine. The reaction was stopped by filtration through GF/B filters using a cell harvester. Data were analyzed by a computerized non-linear regression program.

Measurement of [³H]Inositol Phosphates (IP) Formation

Cells were suspended in Dulbecco's phosphate buffered saline (PBS), and incubated with 5 μCi/ml [³H]m-inositol for 60 min at 37° C., the reaction was stopped by adding CHCl₃:Methanol:HCl (2/1/0.01 v/v). Total [³H]IP were separated by ion exchange chromatography and quantified as described by Forray and El-Fakahany (7).

Calcium Measurements

Intracellular calcium levels ([Ca²⁺]i) were determined with the calcium-sensitive dye fura-2, and microspectrofluorometry, essentially as previously described (1,3). Briefly, cells were plated into polylysine-coated coverslip bottom dishes (MatTek Corporation, Ashland Mass.). To lead with fura-2, cells were washed 3× with HEPES-buffered saline (HBS, in mM: HEPES, 20; NaCl, 150; KCl, 5; CaCl₂, 1; MgCl₂, 1; glucose, 10; pH 7.4) and incubated for 30 minutes at room temperature with fura-2 loading solution (5 μM fura-2/AM, 0.03% pluronic F-127, and 2% heat-inactivated fetal calf serum, in HBS). After loading, cells were washed 3× with HBS, 1 ml of HBS was added, and the dish was placed on the microscope for determination of $[Ca^{2+}]_i$. $[Ca^{2+}]_i$ was measured with a Leitz Fluovert microscope equipped for UV-transmission epifluorescence. Fura-2 fluorescence was alternately excited at 340 and 380 nm (0.25 sec), and a pair of readings (500 nm long pass) was taken every two seconds, and recorded by a personal computer interfaced to a data acquisition and control unit from Kinetek (Yonkers, N.Y.). To determine $[Ca^{2+}]_i$ from the experimental data the background fluorescence was subtracted, and the corrected ratios were converted to $[Ca^{2+}]_i$ by comparison with buffers containing saturating and low free calcium, assuming a $K_D$ of 400 nM (3).

RESULTS

α1a: We screened a human genomic lymphocyte library with a rat PCR fragment that exhibited homology with the α1-AR family. A total of six clones were isolated and characterized by Southern blot analysis. One clone, h13, contained a 4.0 kb XbaI fragment which hybridized with the radiolabeled rat PCR fragment and was subsequently subcloned into pUC vector. DNA sequence analysis indicated greatest homology to human α1a and rat α1a ARs. This clone contained the initiating methionine through Tm6 with ≈1.0–1.5 kb 5' UT region. Subsequent Southern blot, analysis, subcloning and sequencing analysis indicated the presence of a SmaI site ≈150 nts. 5' to the initiating methionine codon. The homology between h13 and rat α1a adrenergic gene breaks just downstream of Tm6, indicating an intron which is located in an analogous region in the α1b- and α1c-AR genes (4,20). In order to obtain a full-length clone, aliquots of human cDNA libraries totaling ≈1.5×10$^6$ recombinants was screened by polymerase chain reaction using specific oligonucleotide primers from sequence determined off the genomic clone (see Materials and Methods). A positive- containing human hippocamppal cDNA library (Stratagene, LaJolla, Calif.) in λ Zap II (≈1.5×10$^6$ recombinants) was screened using traditional plaque hybridization with an internal probe (see Materials and Methods) and resulted in the isolation of two positive cDNA clones, one containing the upstream sequences (from 5' UT through the 5–6 loop; hH22) and the other containing downstream sequences (from within Tm5 through ≈200 nts. with a common XhoI site being present within this common region.

The complete full-length gene was constructed by splicing together two restriction fragments, one being the 3' cDNA (hH14) and the other being the 5' genomic clone (h13), using a unique restriction site (XhoI) present in the overlapping region. In addition, another construct was accomplished by ligating the two cDNA clones (hH14 and hH22), using the overlapping XhoI site; however, since this construct produced the same pharmacology as the genomic/cDNA construct, we will not discuss this recombinant (unpublished observation). The genomic/cDNA construct contains an open reading frame of 1719 bp and encoding a protein of 572 aa in length, having a relative molecular mass of ≈63,000 daltons. Hydropathy analysis of the protein is consistent with a putative topography of seven transmembrane domains, indicative of the G protein-coupled receptor family. Initial sequence analysis revealed that clone α1a/EXJ was most related to an AR since it contained a number of conserved structural features/residues found among the members of the adrenergic receptor family, including conserve cysteines in the second and third extracellular loops, a conserved glycine residue in Tm1, aspartic acid residues in Tm regions II and III, conserved valine residues in TmIII, the DRY sequence at the end of TmIII, the conserved proline residues of Tm regions II, IV, V, VI and VII, and the consensus D-V-L-X-X-T-X-S-I-X-X-L-C IN Tm3 and the consensus G-Y-X-N-S-X-X-N-P-X-I-Y in the Tm VII, both consensus unique to the adrenergic receptor family (2,26). Other features of this human α1a receptor gene are the presence of two potential sites for N-linked glycosylation in the amino terminus (asparagine residues 65 and 82; FIGS. 1a–1I) and the presence of several serines and threonines in the carboxyl terminus and intracellular loops, which may serve as sites for potential phosphorylation by protein kinases.

$\alpha_{1b}$: We screened a human genomic placenta library with probes derived from Tm3, 5 and 6 regions of serotonin 5HT1D$_\beta$ under low stringency. Out of several hundred positive clones pursued by Southern blot analysis, subcloning and sequencing, one resembled the α$_1$ adrenergic family of receptors. This genomic fragment contained Tm3 through Tm6 of a receptor which was most closely related to rat and hamster α$_{1b}$ receptors. In order to obtain a full-length clone, several human cDNA libraries were screened by PCR using primers derived from the 5–6 loop region of the genomic clone (see Materials and Methods). A positive-containing human brainstem cDNA library (Stratagene, LaJolla, Calif.) in λ ZAPII (≈2×10$^6$ recombinants) was screened using traditional plaque hybridization with an internal probe, resulting in the isolation of two identical cDNA clones, containing an insert size of 2.4 kb. Upon sequencing, this clone was found to contain the initiating MET aa, Tm1 through Tm7, and 5' and 3' UT sequences, suggesting a full-length clone on a single EcoRI fragment. This cDNA clone contains an open reading frame of 1563 bp and encodes a protein of 520 aa in length, having a relative molecular mass of ≈57,000 daltons. Hydropathy analysis of the protein is consistent with a putative topography of seven transmembrane domains, indicative of the G protein-coupled receptor family.

Sequence analysis revealed that clone α$_{1b}$/pCEXV was most related to adrenergic receptor since it contained a number of conserved structural features found among the adrenergic receptor family, as described for α$_{1a}$ receptor (see above). This human α$_{1b}$ receptor contains potential sites for N-linked glycosylation in the amino terminus (asparagine residues 10, 24, 29, 34 in FIG. 2A–2H), consistent with the finding that the α$_1$ AR is glycosylated (4,19).

$\alpha_{1c}$: We screened a human genomic lymphocyte library with probes derived from the third, fifth and sixth transmembrane regions of serotonin 5HT1A under low stringency. Out of several hundred positive clones analyzed by Southern blot analysis, subcloning and sequencing (see Materials and Methods), one phage clone resembled a novel α$_1$ AR. This genomic fragment contained Tm1 through Tm6 of a receptor with high homology to the bovine α$_{1c}$ receptor and thus suggesting the presence of an intron downstream of Tm6, as shown for the α$_1$ receptor family (4,12,20). In order to obtain a full-length clone, several human cDNA libraries were screened by PCR, as described for α$_{1b}$ (also see Materials and Methods). A positive-containing human hippocamppal cDNA library (Stratagene, LaJolla, Calif.) in λ ZAPII (≈2×10$^6$ recombinants) was screened, as described for α$_{1b}$. A positive clone (hH 20) was identified which contained a 1.7 kb EcoRI cDNA fragment insert. However, this cDNA clone lacked both the amino end of the receptor (the 5' end of the clone terminated at the 5' end of Tm2) and part of the carboxyl tail (the 3' end of the clone corresponded to 40 aa upstream from the "putative" stop codon). Since an alternative genomic subclone which contained the initiating MET codon in addition to Tm1 through Tm6 was available, we needed to obtain the complete 3' carboxyl tail in order to complete the construct of the full-length clone. This was accomplished by using overlapping 45-mer oligonucleotide primers (corresponding to nts. 1142–1212 in FIG. 3), designed within the carboxyl tail of the receptor (at the 3' end of the hH20 cDNA clone), to screen a human lymphocyte genomic library in order to isolate a genomic clone containing the carboxyl tail that includes the termination codon. Two identical positive human lymphocyte genomic clones were isolated from this library. A 0.6 kb PstI fragment was subcloned and shown to contain most of the carboxyl tail (≈20 aa downstream of Tm7) through the termination codon and ≈200 bp of 3' UT sequence.

The complete full-length gene was constructed by splicing together three restriction fragments: A 0.6 kb HincII fragment from the genomic clone, containing ≈0.4 kb of 5' UT sequence and the initiating MET codon through Tm2;

the 0.8 kb HincII-PstI fragment from the hH cDNA clone, which contains Tm2 through part of the carboxyl tail, overlapping with the 5' genomic clone by 20 nts. (sharing the unique HincII site at position 196 in FIG. 3); and a 0.6 kb PstI fragment from the second hl genomic clone, which contains the carboxyl tail, the stop codon and ≈0.2 kb of 3' UT sequence, and overlapping with the hH cDNA clone (sharing the unique Pst I site within the carboxyl tail at position 1038 in FIGS. 3A–3G).

The resulting genomic/cDNA/genomic construct contains an open reading frame of 1401 bp and encoding a protein of 466 aa in length, having a molecular weight of ≈51,000 daltons. Hydropathy analysis of the protein is consistent with a putative topography of seven transmembrane domains, as indicated for the previously described human $\alpha_{1a}$ and $\alpha_{1b}$ receptors and indicative of the G protein-coupled receptor family. Sequence analysis revealed that clone $\alpha_{1c}$/EXJ was most related to adrenergic receptor because it contained the structural features commonly found among the adrenergic receptor family of receptors, as described for the $\alpha_{1a}$ receptor above. Other features of this human $\alpha_{1c}$ receptor gene is the presence of three potential sites for N-linked glycosylation in the amino terminus, at the same position described for the bovine $\alpha_{1c}$ receptor (asparagine residues 7, 13 and 22 in FIG. 3A–3G) (20). Several threonines and serines exist in the second and third cytoplasmic loops of this $\alpha_{1c}$ receptor, which may serve as potential sites for protein kinases and phosphorylation.

TABLE 1

Competition of adrenergic agonists and antagonists for the binding of [$^3$H]prazosin to membranes prepared from LM(tk$^-$) cells expressing the human $\alpha_{1a}$, $\alpha_{1b}$, and $\alpha_{1c}$-adrenergic receptor cDNA. Membrane preparations from stably transfected cell lines increasing concentrations of various agonists or antagonists as described under "Materials and Methods". Data is shown as the mean ± S.E.M. of the binding parameters estimated by a computerized non-linear regression analysis obtained in three independent experiments each performed in triplicate.

| | pKi | | |
|---|---|---|---|
| | $\alpha_{1a}$ | $\alpha_{1b}$ | $\alpha_{1c}$ |
| AGONISTS | | | |
| Norepinephrine | 6.633 ± 0.12 | 5.614 ± 0.09 | 5.747 ± 0.18 |
| Epinephrine | 6.245 ± 0.10 | 5.297 ± 0.15 | 5.511 ± 0.13 |
| Oxymetazoline | 5.903 ± 0.16 | 5.919 ± 0.07 | 7.691 ± 0.10 |
| Naphazoline | 6.647 ± 0.18 | 6.155 ± 0.04 | 6.705 ± 0.22 |
| Xylometazoline | 5.913 ± 0.20 | 6.096 ± 0.30 | 7.499 ± 0.19 |
| ANTAGONISTS | | | |
| Prazosin | 9.479 ± 0.19 | 9.260 ± 0.23 | 9.234 ± 0.13 |
| WB-4101 | 8.828 ± 0.12 | 7.909 ± 0.13 | 9.080 ± 0.09 |
| (+) Niguldipine | 6.643 ± 0.10 | 6.937 ± 0.12 | 8.693 ± 0.18 |
| Indoramin | 6.629 ± 0.09 | 7.347 ± 0.17 | 8.341 ± 0.25 |
| 5-Methyl Urapidil | 7.795 ± 0.15 | 6.603 ± 0.09 | 8.160 ± 0.11 |
| HEAT | 7.857 ± 0.13 | 8.474 ± 0.10 | 8.617 ± 0.10 |
| Urapidil | 6.509 ± 0.18 | 5.932 ± 0.11 | 6.987 ± 0.14 |
| Rauwolscine | 5.274 ± 0.12 | 4.852 ± 0.08 | 4.527 ± 0.11 |

Pharmacological Analysis: To further assess the functional identity of the cloned cDNA the coding regions were subcloned into the pCEXV-3 expression vector, and LM(tk−) cell lines stably expressing the human cDNA encoding each of the three $\alpha_1$-ARs were established. Membrane preparations of these cell lines showed high affinity binding of [$^3$H]prazosin, with Kd values of 0.21±0.03 nM (Bmax=0.72±0.04 pmol/mg prot), 0.88±0.1 nM (Bmax= 4.59±0.21 pmol/mg prot) and 0.39±0.08 nM (Bmax= 1.9±0.04 pmol/mg prot) for the cells expressing the $\alpha_{1a}$, $\alpha_{1b}$, and $\alpha_{1c}$-ARs respectively. In contrast in competition binding experiments rauwolscine showed extremely low affinity at the three cloned receptors (Table 1), consistent with their identity as $\alpha_1$-AR. The α-adrenergic agonists NE and epinephrine were found to be 6 and 5-fold respectively, more potent at the human $\alpha_{1a}$-AR, conversely the imidazoline derivatives such as oxymetazoline and xylometazoline showed 52-fold higher potency at the $\alpha_{1c}$-AR. Similarly, several antagonists showed marked differences in their potency to inhibit [$^3$H]prazosin binding from the cloned human $\alpha_1$ receptors subtypes. The selective antagonists WB-4101 and 5-methyl-urapidil showed high affinity for the human $\alpha_{1c}$ subtype (0.8 and 7 nM respectively), followed by less than 2-fold lower potency at the human $\alpha_{1a}$ and at least an order of magnitude (15 and 36-fold respectively) lower potency at the human $\alpha_{1b}$-AR. Similarly, indoramin was 50 and 10-fold more potent at the $\alpha_{1c}$ than at the $\alpha_{1a}$ and $\alpha_{1b}$ respectively. The calcium channel blocker (+)-niguldipine showed the highest selectivity for the three $\alpha_1$-AR subtypes, displacing [$^3$H]prazosin 112 and 57-fold more potently from the $\alpha_{1c}$ than from $\alpha_{1a}$ and $\alpha_{1b}$ transfected cells respectively.

Table 2. Receptor-mediated formation of [$^3$H]IP in cell lines transfected with the human $\alpha_1$-adrenergic receptors cDNA.

Cell lines stably expressing the human $\alpha_1$-adrenergic receptors were obtained and the IP formation was measured in the absence or presence of 10 μM norepinephrine (NE) in the presence of 10 mM LiCl as described under "Material and Methods". Data are shown as mean±S.E.M. of three independent experiments performed in triplicate.

| Cell Line | [$^3$H]IP dpm/dish | Fold Stimulation | Receptor [a] Density pmol/mg Prot |
|---|---|---|---|
| 293 $\alpha_{1a}$ | | | 3.30 |
| Control | 288 ± 29 | | |
| NE | 3646 ± 144 | 13 | |
| CHO $\alpha_{1b}$ | | | 0.49 |
| Control | 1069 ± 26 | | |
| NE | 5934 ± 309 | 6 | |
| NIH3T3 $\alpha_{1c}$ | | | 0.24 |
| Control | 722 ± 61 | | |
| NE | 13929 ± 1226 | 19 | |

[a] Determined by [$^3$H]Prazosin binding.

The formation of [$^3$H]IP was measured in 293, CHO, and NIH3T3 cell stably expressing the cloned human $\alpha_{1a}$, $\alpha_{1b}$, $\alpha_{1c}$-ARs respectively, to assess the functional coupling of these receptors with the activation of phosphatidyl-inositol specific phospholipase C (PI-PLC). As shown in Table 2, the adrenergic agonist NE (10 μM) activated the formation of IP by 13-fold in cells expressing the $\alpha_{1a}$ receptor, and by 5 and 15-fold in cells expressing the $\alpha_{1a}$, $\alpha_{1b}$ and $\alpha_{1c}$ receptors respectively. Furthermore, when cells expressing $\alpha_{1b}$ and $\alpha_{1c}$ receptors were incubated in the presence of 10 μM NE, a rapid increase of cytosolic calcium was observed. The response was characterized by an early peak, followed by a plateau that slowly declined towards resting calcium levels (FIG. 7). The concentration of [Ca$^{2+}$]$_i$, was increased by 172±33 (n=6), 170±48 (n=6) and 224±79 nM (n=6) in cell lines transfected with the $\alpha_{1a}$, $\alpha_{1b}$ and $\alpha_{1c}$ receptors respectively. The changes in [Ca$^{2+}$]$_i$ induced by NE were suppressed by preincubation of the cells with 10 nM prazosin, indicating that the calcium response was mediated by $\alpha_1$-ARs.

We have cloned DNA representing three $\alpha_1$-ARs subtypes ($\alpha_{1a}$, $\alpha_{1b}$ and $\alpha_{1c}$) from human brain cDNA and genomic DNA. Of all known G protein-coupled receptor sequences (EMBL/Genbank Data Base), the greatest homology was found between $\alpha_{1a}$/EXJ and the rat $\alpha_{1a}$ AR (12), rat $\alpha_{1d}$ AR (16) and a previously reported putative human "$\alpha_{1a}$" adrenergic receptor (H318/3) (2). Comparison of the human $\alpha_{1a}$ deduced aa sequence with known $\alpha_{1a}$ ARs indicates the greatest concentration of identical aa to be in the transmembrane domains. In these Tm regions, the percentage of identity for the human $\alpha_{1a}$ AR is 98% compared to rat $\alpha_{1a}$ AR (12) (this is approximately the same for rat $\alpha_{1d}$ since rat $\alpha_{1d}$AR is the same as rat $\alpha_{1a}$ AR, except for two amino acid differences), 100% with the previously reported H318/3, 78% with the human $\alpha_{1b}$ receptor (see below), and 69% with the human $\alpha_{1c}$ receptor (see below), which is typical among subtypes. When considering the full-length proteins, the percent identity drops and is only 50% for the human $\alpha_{1b}$ and 49% for the human $\alpha_{1c}$ receptor. Both the alignment (see FIG. 4) and percent identity of this human $\alpha_{1a}$ sequence, relative to other members of the AR family strongly suggest that this is a new receptor and is the human species homolog of the rat $\alpha_{1a}$ receptor.

FIG. 4 shows a comparison between the deduced aa sequence of $\alpha_{1a}$/EXJ and the sequences of rat $\alpha_{1a}$ and HAR. An overall homology of 83.5% aa identity with rat $\alpha_{1a}$ and 86.5% aa identity with the previously published H318/3 clone was observed, suggesting that our human $\alpha_{1a}$ receptor is not any more related to the previously published putative human "$\alpha_{1a}$" than it is to the rat $\alpha_{1a}$ receptor. In fact, in support of this conclusion, is the fact that the overall aa homology of rat $\alpha_{1a}$ receptor with our human $\alpha_{1a}$ receptor is 83.5% but is only 72% compared to the H318/3 receptor. The main differences between our human $\alpha_{1a}$ receptor and the previously reported "$\alpha_{1a}$" receptor in relation to the rat $\alpha_{1a}$ are indicated in FIG. 4. Most notably are the differences observed at both the amino and carboxyl ends of the receptor. Specifically, both our human $\alpha_{1a}$ and rat $\alpha_{1a}$ use the starting MET aa at position 1 (see FIG. 4) whereas the previously published H318/3 uses the starting MET 48 aa downstream. Also, the amino terminus of the H318/3 clone is completely divergent from either rat $\alpha_{1a}$ or our human $\alpha_{1a}$ receptor until about 12 aa upstream of Tm1 where significant homology begins. Similarly, in the carboxyl tail, the homology of H318/3 diverges ≈90 aa upstream from the stop codon of either rat or our human $\alpha_{1a}$ receptor and instead, uses a stop codon 30 aa upstream from the stop codon on either of these receptors. Finally, the H318/3 clone has an amino terminal extracellular region that does not contain potential sites for N-linked glycosylation (2), in contrast to the rat $\alpha_{1a}$ or our human $\alpha_{1a}$ receptor, which contains two potential sites (12, see also FIG. 1 and above). Thus, these data strongly suggest that our human $\alpha_{1a}$ receptor is different in sequence from the previously reported putative human "$\alpha_{1a}$" (H318/3) but is more related to the previously published rat $\alpha_{1a}$ receptor. Interestingly, the rat $\alpha_{1a}$ aa sequence diverges from both human $\alpha_{1a}$ receptors for ≈65 aa in the carboxyl tail (position 434–508 in FIG. 1); however, homology is seen again in our human $\alpha_{1a}$ receptor but not with H318/3, downstream from this region.

The cloning of different $\alpha_1$ receptor subtypes permits analysis of both the pharmacological and functional properties of adrenergic receptors. The human $\alpha_{1b}$/pcEXV clone exhibited the greatest homology with the rat and hamster $\alpha_{1b}$ receptors, out of all known G protein-coupled receptor clones (EMBL/Genbank Data Bank). Comparison of the human $\alpha_{1b}$ deduced aa sequence with known $\alpha_1$ ARs indicates the greatest homology in the transmembrane regions. In these Tm regions, the percent identity for the human $\alpha_{1b}$ AR is 99% compared to either rat (25) or hamster (4) αb receptor, 78% with human $\alpha_{1a}$ receptor and 75% with human $\alpha_{1c}$ receptor, which is typical among subtypes. When analyzing the full-length proteins, the percent identity slightly drops and is 94.5% compared to rat $\alpha_{1b}$, 95.5% compared to hamster $\alpha_{1b}$ receptor, 50% compared to human $\alpha_{1a}$ and 51% compared to human $\alpha_{1c}$ receptor. Both the alignment (see FIG. 5) and percent identity of this human $\alpha_{1b}$ sequence, relative to other members of the AR family, strongly suggest that this clone represents a new receptor and is the human species homologue of the rat/hamster $\alpha_{1b}$ receptor. FIG. 5 shows a comparison between the deduced amino acid sequence of $\alpha_{1b}$/pcEXV and the aa sequence of rat $\alpha_{1b}$ and hamster $\alpha_{1b}$ receptors.

A third human adrenergic receptor clone, $\alpha_{1c}$/EXJ, showed the greatest homology with the bovine $\alpha_{1c}$ AR gene (20), from all known G protein-coupled receptor sequences (EMBL/Genbank Data Bank). Comparison of the human $\alpha_{1c}$ deduced aa sequence with the $\alpha_1$ ARs indicates the greatest homology to be in the transmembrane regions. In these Tm regions, the percent identity for the human $\alpha_{1c}$ AR is 97% compared to the bovine $\alpha_{1c}$ AR (20), 75% with human $\alpha_{1b}$ receptor and 69% with human $\alpha_{1a}$ receptor, which is typical among subtypes. When one examines the full-length proteins, the percent identity drops and is only 51% compared to either the human $\alpha_{1b}$ or human $\alpha_{1a}$ receptor. FIG. 6 shows a comparison between the deduced amino acid sequence of $\alpha_{1c}$/EXJ and the aa sequence of bovine $\alpha_{1c}$. An overall homology of 92% aa identity with bovine $\alpha_{1c}$ receptor was observed. Both the alignment (see FIG. 6) and percent identity of this human $\alpha_{1c}$ sequence, relative to other members of the AR family, strongly suggest that this clone represents a new receptor and is the human species homologue of the bovine $\alpha_{1c}$ receptor.

The stable expression of the three cloned human $\alpha_1$ receptors enabled the characterization of their pharmacological as well as their functional properties and allowed identification of certain unique features of the human receptors, not predicted from previous data. The rank-order of potency of known α-adrenergic agonists and antagonists to compete with [$^3$H]prazosin in binding assays, confirmed that the cloned cDNAs encode three human receptors of the $\alpha_1$-AR family. Moreover, the potencies of selective antagonists such as WB-4101 and 5-methyl-urapidil at the three human $\alpha_1$-receptors were found to be in close agreement with the potencies of these antagonists at the cloned rat $\alpha_{1a}$, hamster $\alpha_{1b}$, and bovine $\alpha_{1c}$ (4, 12, 20). These results suggest that the sequence homology between the three mammalian $\alpha_1$ receptors resulted in a conservation of their pharmacological properties across different species. In the past the pharmacological characterization of $\alpha_1$-adrenergic receptors took advantage of the existence of selective antagonists such as WB-4101 and 5-methyl-urapidil that bind with high affinity to a subset of $\alpha_1$-receptors classified as $\alpha_{1a}$ (9, 15). Our results using these selective antagonists indicate that these antagonists bind with similar affinity to both human $\alpha_{1a}$ and α1c-receptors, and that they can only discriminate between either of these two subtypes and the $\alpha_{1b}$ receptor. The calcium channel blocker (+)-niguldipine was found to bind with high affinity to a subset of $\alpha_1$-receptors also labeled by [$^3$H]5-methyl-urapidil in rat brain, thus defining this antagonist as $\alpha_{1a}$ selective (8). The high affinity of the human $\alpha_{1c}$ receptor for (+)-niguldipine and the fact that it binds to the human $\alpha_{1a}$ and $\alpha_{1b}$ subtypes, with at least an order of magnitude lower affinity, strongly supports the notion that the human $\alpha_{1c}$ gene encodes the pharmacological $\alpha_{1a}$-receptor subtype. The possibility that this also holds true in the rat, is suggested by the fact that the potency of (+)niguldipine for the rat $\alpha_{1a}$ clone is also at least an order of magnitude lower than that found for this antagonist in rat tissues. Moreover in spite of the earlier reports on the absence of the bovine $\alpha_{1c}$ cognate in rat tissues (20), (24,21) pharmacological evidence suggests that this species express an $\alpha_1$ receptor similar to the cloned $\alpha_{1c}$ receptor. These data altogether indicate that in trying to match the pharmacological subclassification of the $\alpha_1$-ARs with the evidence from molecular cloning studies, the initial assignment of the cloned rat $\alpha_{1a}$ receptor with the $\alpha_{1a}$ receptor subtype was inadequate. Recently, a rat cDNA clone 99.8% homologous to the rat $\alpha_{1a}$-receptor, was described as a novel $\alpha_{1d}$ subtype (16); however, this incorrect classification was due to the poor correlation between the affinities of $\alpha_{1a}$-selective antagonists in tissue preparations versus the cloned rat $\alpha_{1a}$ receptor.

The three human $\alpha_1$ receptor subtypes were able to induce the formation of IP, consistent with the known functional coupling of $\alpha_1$-ARs, through a GTP-dependent protein to the activation of PI-PLC. In addition we demonstrated that upon receptor activation by adrenergic agonists, the human $\alpha_1$ subtypes induced transient changes three in $[Ca^{2+}]_i$. Consistent with the mobilization of calcium from intracellular stores by inositol-1,3,5 triphosphate, released by the receptor-mediated activation of PI-PLC.

We have cloned and expressed three human cDNA that encode functional $\alpha_1$-ARs. These three transcripts display significant pharmacologic as well as molecular features to constitute distinct $\alpha_1$-AR subtypes. In sharp contrast with the restricted expression of the rat and bovine transcripts, our findings indicate that species homologs of the three $\alpha_1$-ARs are expressed in human tissues. These findings together with recent reports on the dissimilar tissue distribution of the $\alpha_{1b}$ and $\alpha_{1c}$ receptor cognates between animal species such as rat and rabbit (21), commonly used in the development of novel $\alpha_1$-adrenergic agents, emphasize the need to study the pharmacological properties of the human $\alpha_1$-receptors. In this regard, the results from this study on the selectivity of clinically effective antihypertensives such as indoramin, as well as vasoconstrictors such as oxymetazoline and xylometazoline for the human $\alpha_{1c}$-AR, suggest a potential role for this $\alpha_1$-receptor subtype in the physiological control of vascular tone in the human. Thus, the availability of cell lines expressing each of the human $\alpha_1$-receptor subtypes constitute a unique tool in the design of subtype specific agonists and antagonists, that can be targeted to selective therapeutic applications. Of specific interest for therapeutics are subtype selective alpha-1 antagonists for the treatment of Benign Prostatic Hypertrophy, coronary heart disease, insulin resistance, atherosclerosis, sympathetic dystrophy syndrome, glaucoma, cardiac arrythymias, erectile dysfunction, Reynaud's syndrome, hypertension and urinary retention (44, 27,31,32,33,34,35,48). Further interest exists for subtype selective alpha-1 agonists for the treatment of congestive heart failure, nasal congestion, urinary incontinence and hypotension(45,46,47,48). In each case, a more selective drug is expected to reduce the side effects which presently limit this avenue of therapy.

The following compounds were synthesized in order to evaluate their ability to act as antagonists of $\alpha_1$-receptor function in human prostrate. The synthetic methods used to synthesize are provided herein.

The following Experimental Details are set forth to aid in an understanding of the invention, and are not intended, and should not be construed, to limit in any way the invention set forth in the claims which follow thereafter.

EXPERIMENTAL DETAILS

Prazosin and 5-methylurapidil were obtained from Research Biochemicals, Inc. A30360 (4-fluoro-4-(8fluoro-1,3,4,5-tetrahydro-2H-pyrido[4,3-b]indol-2-yl)butyrophenone hydrochloride) was obtained from Aldrich Chemical Co. Other compounds were prepared according to the examples which follow.

EXAMPLE 1

Synthesis of Terazosin Hydrochloride
N-(2-Furoyl)piperazine

This compound and its preparation has been described in Great Britain Patents 1,390,014 and 1,390,015. Piperazine hexahydrate (194 g, 1 mole) was dissolved in 250 ml $H_2O$. The solution was acidified to pH 4.5 with 6N HCl. Furoyl chloride (130.5 g, 1 mole, Aldrich) was added along with 10% NaOH solution at such a rate that the pH was maintained at 4.5. After 1 hour, the solution was made basic (pH=8.5) with NaOH solution. The reaction mixture was continuously extracted with chloroform for 36 hours. The $CHCl_3$ extract was dried over $MgSO_4$, and filtered. Distillation gave 108.2 g product (60%), b.p. 132°–138° C./0.6 mm Hg, m.p. 69°–70° C.

N-(Tetrahydro-2-furoyl)piperazine

The furoylpiperazine of Example 1 was converted to the hydrobromide salt (m.p. 173°–175° C.). This salt (39.0 g) in 250 ml methyl alcohol and 9.0 g Raney nickel was hydrogenated at 3 atm. After uptake of $H_2$ ceased, the catalyst was filtered, the solvent concentrated, and the residue crystallized from isopropyl alcohol to give 35.2 g. tetrahydrofuroylpiperazine HBr, m.p. 152°–156° C. This was suspended in 20 ml $H_2O$. Then 10.5 g 50%, NaOH solution was added slowly followed by 2.0 g solid $Na_2CO_3$. This was extracted with 4×100 ml portions of warm $CHCl_3$. The $CHCl_3$ extractions were distilled to give 22.5 g tetrahydrofurolylpiperazine, b.p. 120°–125° C./0.2 mm Hg.

2[4-(Tetrahydro-2-furoyl)piperazinyl]-4-amino-6,7-dimethoxyquinazoline hydrochloride To 7.00 g 2-chloro-4-amino-6,7-dimethoxyquinazoline (Lancaster Synthesis) in 50 ml methoxyethanol was added 10.8 g, tetrahydrofurolylpiperazine, and the mixture refluxed 3 hours. The clear solution was concentrated and an aqueous solution of potassium bicarbonate was added. The resultant solid that formed was filtered and washed with water. It was then added to methanol and the resulting suspension was acidified with a solution of hydrogen chloride in isopropyl alcohol. The resulting solution was concentrated and the residue crystallized from isopropyl alcohol giving 8.12 g. of product, m.p. 278°–279° C.

EXAMPLE 2

Preparation of Indoramin
4-Benzamido-1-[2-(3-indolyl)ethylpyridinium Bromide

A solution of 4-benzamidopyridine (1.98 g) and 3-(2-bromoethyl)indole (2.24 g) in EtOH (15 ml) was refluxed for 2 hours, and the crystallized product (3.13 g, mp 264°–266° C.) was collected by filtration from the hot reaction mixture. Recyrstallization gave the hydrate.

3-[2-4-Benzamidopiperid-1-yl)ethyl]indole (Indoramin)
4-Benzamido-1-[2-(3-indolyl)ethyl]pyridinium bromide (3.0 g) in 91% EtOH (300 ml) containing $Et_3N$ (0.8 g) was hydrogenated in the presence of freshly prepared W-7 Raney Ni catalyst (ca. 3 g) at 28.12 kg/cm² and 50° for 4 hours. After filtering off the catalyst, the filtrate was evaporated and the residue was shaken with CHCl$_3$ and 2N NaOH. The resulting insoluble material (1.61 g, mp 203°–206° C.) was collected and dried. Recrystallization from EtOH gave the product (1.34 g), as colorless needles.

EXAMPLE 3

Preparation of 1-(3-benzoylpropyl)-4-benzamidopiperidine (Compound 9)

A mixture of 4-chlorobutyrophenone (447 mg, 2.45 mmol), 4-benzamidopiperidine (500 mg, 2.45 mmol) and K$_2$Co$_3$ (338 mg, 2.45 mmol) was heated up in boiling water bath for 1 hour. The reaction mixture was portioned between water and CHCl$_3$. The organic layer was separated and dried over Na$_2$SO$_4$. After filtration and removal of solvent, the residue was purified by chromatography (SiO$_2$, MeOH:CHCl$_3$, 5:95). Recrystallization from AcOEt/hexane gave a white powder (78 mg, 8.2%). mp 143°–144° C.; $^1$H NMR (CD$_3$OD, 400 MHz) β 1.65 (dq, J$_1$=3.16 Hz, J$_2$=11.9 Hz, 2H), 1.90–2.00 (m, 4H), 2.18 (t, J=11.9 Hz, 2H), 2.48 (m, 2H), 3.00–3.10 (m, 4H), 3.88 (m, 1H), 7.40–8.00 (m, 10H); Mass spectrum (M+1)$^+$ at m/z 351.

EXAMPLE 4

Preparation of 1-[3-(4-chlorobenzoyl)propyl]-4-benzamidopiperidine (Compound 7)

A mixture of 3-(4-chlorobenzol)propyl bromide (640 mg, 2.45 mmol), 4-benzamidopiperidine (500 mg, 2.45 mmol) and K$_2$CO$_3$ (1.01 g, 7.34 mmol) in 50 ml of acetone was heated up to refluxing condition for 48 hours. The solid was removed by filtration. Concentration of filtrate in vacuo gave a yellowish solid, which was purified by chromatography (SiO$_2$, MeOH:CHCl$_3$, 5:95). 320 mg (33.9%) of white powder was obtained $^1$H NMR (CDCl$_3$, 300 mHz) δ 1.46 (dq, J$_1$=1.0 Hz, J$_2$=8.4 Hz, 2H), 1.90–2.10 (m, 4H), 2.16 (m, 2H), 2.43 (t, J=6.9 Hz, 2H), 2.80–2.90 (m, 2H), 2.97 (t, J=6.9 Hz, 2H), 3.97 (m, 1H), 5.92 (d, J=7.8 Hz, 1H, N-H), 7.40–8.00 (m, 9H); Product was converted to HCl salt and recrystallized with MeOH/Et$_2$O, mp 243°–244° C.; Calcd for C$_{22}$H$_{25}$ClN$_2$O$_2$.HCl.H$_2$O: C 60.15, H 6.37, N 6.37; Found: C 60.18, H 6.34, N6.29.

EXAMPLE 5

Preparation of SKF-104856

1-[(4-Chlorophenyl)thio}-2-propanone

Chloroacetone (32.3 g, 0.347 mol) was added to a mixture of 4-chlorothiophenol (50 g, 0.347 mmol) and sodium hydroxide (14 g, 0.347 mol) in water (400 ml) and the mixture was stirred at 25° C. for 1 hour. The mixture was extracted with ethyl ether and the organic phase was washed with water, dried with magnesium sulfate and concentrated to give 69 g (99%) of 1-[(4-chlorophenyl)thio]-2-propanone.

5-Chloro-3-methylbenzo(b)thiophene

1-[(4-Cholorophenyl)thio}-2-propanone (50 g, 0.25 mol) was added to polyphosphoric acid (300 g) and the mixture was stirred as the temperature was gradually raised to 120° C. as an exotherm started. The mixture was stirred at 130° C. for 1 hour, diluted with water, extracted with ethyl ether and the organic phase was dried and concentrated. The residue was stirred in methanol (200 ml), filtered and the filtrate concentrated to give 17.5 g (40%) of 5-chloro-3-methylbenzo(b)thiophene: bp 120° C. (0.6 mm Hg).

Ethyl5-chloro-3-methylbenzo(b)thiophene-2-carboxylate n-Butyllithium in hexane (2.6M, 2.3 ml) was added to a solution of 5-chloro-3-methylbenzo(b)thiophene (1,0 g, 6 mmol) in ethyl ether (20 ml) stirred at 0° C. under argon. The mixture was stirred for 30 minutes and transferred slowly under argon pressure to a stirred solution of ethyl chloroformate (0.63 g, 6 mmol) in ethyl ether (20 ml). The mixture was stirred at 0° C. for 30 minutes and at 25° C. for 1.5 hours. The mixture was treated with water and the organic phase was dried, concentrated and triturated with hexane to give 1.0 g (67%) of ethyl 5-chloro-3-methylbenzo(b)thiophene-2-carboxylate: mp 92.5°–94 ° C.

Ethyl 3-bromomethyl-5-chlorobenzo(b)thiophene-2-carboxylate

A mixture of ethyl 5-chloro-3-methylbenzo(b)thiophene-2-carboxylate (9.0 g, 0.035 mol), N-bromosuccinimide (6.53 g, 0.037 mol) and benzoyl peroxide (130 mg) in carbon tetrachloride (150 ml) was refluxed and illuminated with sunlamp for 2 hours. The resulting suspension was cooled, filtered and the filter cake was triturated with methanol to give 9.9 g, (85%) of the methanol-insoluble ethyl 3-bromomethyl-5-chlorobenzo(b)thiophene-2-carboxylate: mp 148°–150° C.

Ethyl 5-Chloro-3-[N-(2,2-dimethoxyethyl)-N-methyl (aminomethyl)]benzol(b)thiophene-2-carboxylate A mixture of ethyl 3-bromomethyl-5-chlorobenzo(b) thiophene-2-carboxylate (11 g, 0.033 mol), methylaminoacetaldehyde dimethyl acetal (4.76 g, 0.04 mol) and potassium carbonate (11.4 g, 0.8 mol) in dry acetone (200 ml) was stirred for 48 hours, filtered and the filtrate concentrated to give 11.8 g, (96%) of ethyl 5-chloro-3-(N-2,2-dimethoxyethyl)-N-methyl(aminomethyl)benzol(b)thiophene-2-carboxylate.

Ethyl 7-chloro-3,4-dihydro-4-methylthieno[4,3,2-ef]-[3] benzazepine-2-carboxylate Ethyl 5-chloro-3-[N-(2,2-dimethoxyethyl)-N-methyl (aminomethyl)]benzo[b]thiophene-2-carboxylate (3.0 g, 8.1 mmol) was added in portions to trifluoromethanesulfonic acid (10 ml) stirred at 0° C. under argon. The mixture was stirred at 25° C. for 45 minutes and diluted with water. The mixture was basified with aqueous sodium hydroxide and extracted with ethyl ether to give ethyl 7-chloro-3,4-dihydro-4-methylthieno-[4,3,2-ef][3]benzazepine-2-carboxylate.

Ethyl 7-chloro-3,4,5,6-tetrahydro-4-methylthieno[4,3,2-ef][3]benzazepine-2-carboxylate Diborane in tetrahydrofuaran (1M, 40 ml) was added to a solution of ethyl 7-chloro-3,4-dihydro-4-methylthieno[4,3,2-ef][3]benzazepine-2-carboxylate (2.8 g) in tetrahydrofuran (30 ml) stirred at 0° C. The mixture was refluxed for 3 hours and stirred at 25° C. for 18 hours, cooled, treated with methanol (50 ml), refluxed for 18 hours and concentrated. The residue was triturated with ethyl ether-hexane (3:1) to give 1.6 g (84%) of ethyl 7-chloro-3,4,5,6-tetrahydro-4-methylthieno[4,3,2-ef][3]benzazepine-2-carboxylate: mp 138°–140 ° C. The free base was treated with hydrogen chloride to give ethyl 7-chloro-3,4,5,6-tetrahydro-4-methylthieno[4,3,2-ef][3]benzazepine-2-carboxylate hydrochloride: mp 240° C.

7-Chloro-3,4,5,6-tetrahydro-4-methylthieno[4,3,2-ef][3] benzazepine-2-methanol

A solution of ethyl 7-chloro-3,4,5,6-tetrahydro-4-methylthieno[4.3.2-ef][3]benzazepine-2-carboxylate (4.0 g, 12.9 mmol), in ethyl ether (48 ml) was treated with lithium aluminum hydride (0.53 g, 14 mmol). The mixture was stirred for 1.5 hours, cooled and treated carefully with water (2.0 ml), 10% sodium hydroxide (1.0 ml) and water (2.0 ml). The resulting mixture was filtered and the solvent evaporated to give 1.9 g (57%) of 7-chloro-3,4,5,6-tetrahydro-4-methylthieno[4,3,2-ef][3]benzazepine-2-methanol: mp 184°–185° C.

7-Chloro-3,4,5,6-tetrahydro-4-methylthieno-4,3,2-ef][3] benzazepine-2-carboxaldehyde A solution of 7-chloro-3,4,5,6-tetrahydro-4-methylthieno[4,3,2-ef][3]benzazepine-2-methanol (1.6 g, 6 mmol) in dichloromethane (150 ml) was stirred under argon with activated manganese dioxide (8.3 g) for 2 hours. The mixture was filtered through Celite™ and the filtrate was dried with magnesium sulfate and concentrated to give a 63% yield of 7-chloro-3,4,5,6-tetrahydro-4-methylthieno[4,3,2-ef][3]benzazepine-2-carboxaldehyde.

7-Chloro-2-ethenyl-3,4,5,6-tetrahdyro-4-methylthieno[4,3,2-ef][3]benzazepine (SKF-104856)

Sodium hydride (60% dispersion in mineral oil. 3.8 mmol) was added to a stirred solution of methyltriphenylphosphonium bromide (1.35 g, 3.8 mmol) in dry tetrahydrofuran (30 ml) and stirred for 15 minutes. The mixture was treated with a solution of 7chloro-3,4,5,6-tetrahydro-4-methylthieno[4,3,2-ef][3]-benzazepine-2-carboxaldehyde, prepared as in Example 3, (0.5 g, 1.9 mmol) in dimethylformamide (4 ml), stirred at 25° C. for 16 hours, quenched with ice and extracted with ethyl acetate. The organic phase was washed, dried and concentrated and the residue was chromatographed on silica gel eluted with a gradient of methylene chloride to methanol-methylene chloride (3.5:96.5). The product was treated with hydrogen chloride to give 0.2 g (35%) of 7-chloro-2-ethenyl-3,4,5,6-tetrahydro-4-methylthieno[4,3,2-ef][3]benzazepine hydrochloride: mp 234°–236° C.

The following is an example of the use of the cloned Human $\alpha_1$ adrenergic receptors to identify the relevant $\alpha_1$-Receptor subtype for the therapy of Benign Prostatic Hypertrophy.

EXAMPLE 6

Protocol for the Determination of the Potency of $\alpha_1$ Antagonists

The activity of compounds at the different human receptors was determined in vitro using cultured cell lines that selectively express the receptor of interest. These cell lines were prepared by transfecting the cloned cDNA or cloned genomic DNA or constructs containing both genomic DNA and cDNA encoding the human α-adrenergic, serotonin, histamine, and dopamine receptors as follows:

$\alpha_{1a}$ Human Adrenergic Receptor: The entire coding region of α1A (1719 bp), including 150 basepairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequence were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid α1A/EXJ (expression vector containing the α1A receptor gene) and the plasmid pGCcos3neo (plasmid containing the aminoglycoside transferase gene) into LM(tk⁻), CHO, and NIH3T3 cells, using calcium phosphate technique. The cells were grown, in a controlled environment (37° C., 5% $Co_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 $\mu$g/ml streptomycin sulfate. Stable clones were then selected for resistance to the antibiotic G-418 (1 mg/ml), and membranes were harvested and assayed for their ability to bind [$^3$H]prazosin as described below (see "Radioligand Binding assays").

$\alpha_{1B}$ Human Adrenergic Receptor: The entire coding region of α1B (1563 bp), including 200 basepairs and 5' untranslated sequence (5' UT) and 600 bp of 3' untranslated sequence (3' UT), was cloned into the EcoRI site of pCEXV-3 eukaryotic expression vector. The construct involved ligating the full-length containing EcoRI brainstem cDNA fragment from λ ZapII into the expression vector. Stable cell lines were selected as described above.

$\alpha_{1C}$ Human Adrenergic Receptor: The entire coding region of α1C (1401 bp), including 400 basepairs of 5' untranslated sequence (5' UT) and 200 bp of 3' untranslated sequence (3' UT), was cloned into the KpnI site of the polylinker-modified pCEXV-3-derived eukaryotic expression vector, EXJ.RH. The construct involved ligating three partial overlapping fragments: a 5' 0.6 kb HincII genomic clone, a central 1.8 EcoRI hippocampal cDNA clone, and a 3' 0.6 Kb PstI genomic clone. The hippocampal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above.

Radioligand Binding Assays: Transfected cells from culture flasks were scraped into 5 ml of 5 mM Tris-HCl, 5 mM EDTA, pH 7.5, and lysed by sonication. The cell lysates were centrifuged at 1000 rpm for 5 min at 4° C., and the supernatant was centrifuged at 30,000×g for 20 min at 4° C. The pellet was suspended in 50mM Tris-HCl, 1 mM $MgCl_2$, and 0.1% ascorbic acid at pH 7.5. Binding of the α1 antagonist [$^3$H]prazosin (0.5 nM, specific activity 76.2 Ci/mmol) to membrane preparations of LM(tk−) cells was done in a final volume of 0.25 ml and incubated at 37° C. for 20 min. Nonspecific binding was determined in the presence of 10 $\mu$M phentolamine. The reaction was stopped by filtration through GF/B filters using a cell harvester. Inhibition experiments, routinely consisting of 7 concentrations of the tested compounds, were analyzed using a non-linear regression curve-fitting computer program to obtain Ki values.

EXAMPLE 7

Functional Properties of $\alpha_1$ Antagonists in the Human Prostate

The efficacy of $\alpha_1$ adrenergic antagonists for the treatment of benign prostatic hyperplasia (BPH) is related to their ability to elicit relaxation of prostate smooth muscle. An index of this efficacy can be obtained by determining the potency of $\alpha_1$ antagonists to antagonize the contraction of human prostatic tissue induced by an $\alpha_1$ agonist "in vitro". Furthermore, by comparing the potency of subtype selective $\alpha_1$ antagonists in binding assays using human $\alpha_1$ receptors with their potency to inhibit agonist-induced smooth muscle contraction, it is possible to determine which of the $\alpha_1$ adrenergic receptor subtypes is involved in the contraction of prostate smooth muscle.

Methods: Prostatic adenomas were obtained at the time of surgery from patients with symptomatic BPH. These were cut into longitudinal strips of 15 mm long and 2–4 mm wide, and suspended in 5 ml organ baths containing Krebs buffer (pH 7.4). The baths were maintained at 37° C. and continuously oxygenated with 5% $CO_2$ and 95% $O_2$. Isometric tension was measured with a Grass Instrument FT03 force transducer interfaced with a computer. Tissue strips were contracted with varying concentrations of phenylephrine after incubating for 20 minutes in the absence and presence of at least three different concentrations of antagonist. Dose-response curves for phenylephrine were constructed, and the antagonist potency (pA$_2$) was estimated by the dose-ratio method. The concentration of some antagonists in the tissue bath was assessed by measuring the displacement of [3H] prazosin by aliquots of the bath medium, using membrane preparations of the cloned human $\alpha_{1C}$ receptor. This control was necessary to account for losses of antagonist due to adsorption to the tissue bath and/or metabolism during the time the antagonists were equilibrated with the prostate tissue.

Results:

Table 3 shows that the pA$_2$ values measured for a series of $\alpha_1$ antagonists in human prostate tissue correlate closely (r=0.76) with the corresponding pK$_i$ values measured in the $\alpha_{1C}$ receptor assays. In contrast, the human prostate pA$_2$ values correlate poorly with the pK$_i$ values measured at the $\alpha_{1A}$ (r=-0.06) and $\alpha_{1B}$ (r=-0.24) adrenergic receptors. (See FIG. 7) Thus, antagonists which are more potent at blocking the $\alpha_{1C}$ adrenergic receptor are more effective at blocking the contraction of the human prostate than antagonists which are more potent at the $\alpha_{1A}$ or $\alpha_{1B}$ adrenergic receptors. In addition, antagonists which are selective for the $\alpha_{1C}$ receptor will have a better therapeutic ratio than nonselective $\alpha$ antagonists.

TABLE 3

COMPARISON OF THE BINDING POTENCY (pK$_1$) OF ALPHA-1 ANTAGONISTS IN CLONED HUMAN RECEPTORS AND THEIR PROTENCY (pA$_2$) TO INHIBIT PROSTATE SMOOTH MUSCLE CONTRACTION

|  | Human Alpha-1 Adrenergic (pK$_1$) | | | Human |
| --- | --- | --- | --- | --- |
| Compound | a1A | a1B | a1C | Prostate (pA) |
| 1 Prazosin | 9.48 | 9.26 | 9.23 | 9.08 |
| 3 A-30360 | 7.49 | 7.86 | 8.52 | 8.72 |
| 4 5-Methyl-Urapidil | 7.79 | 6.77 | 8.35 | 8.38 |
| 5 Indoramin | 6.74 | 7.39 | 8.35 | 7.86 |
| 6 SKF-104856 | 8.48 | 7.50 | 7.60 | 7.66 |
| 7 Compound 7 | 6.82 | 7.18 | 8.42 | 7.63 |
| 9 Compound 9 | 6.12 | 6.76 | 7.83 | 7.41 |
| 10 Terazosin | 8.46 | 8.71 | 8.16 | 7.30 |

REFERENCES

1. Borden, L. A., Maxfield, F. R., Goldman, J. E., and Shelanski, M. L., Neurobiol. Aging., 13, 33–38, 1991.
2. Bruno, J. F., J. Whittaker, J. Song, and M. Berelowitz. Biochem. Biophys. Res. Comm. 179, 1485–1490 (1991).
3. Bush, A. W., Borden, L. A., Greene, L. A., and Maxfield, F. R., J. Neurochem. 57, 562–574, 1991.
4. Cotecchia, S., Schwinn, D. A., Randall, R. R., Lefkowitz, R. J., Caron, M. G., and Kobilka, B. K., Proc. Natl. Acad. Sci. USA, 85, 7159–7163, 1988.
5. Feinberg, A. P., and B. Vogelstein. Anal. Biochem. 132, 6–13 (1983).
6. Flavahan, N. A. and Vanhoutte, P. M., In: The Alpha-1 Adrenergic Receptors, (ed. by R. R. Ruffolo, Jr., Humana Press, Clifton, N.J.) pp. 351–403, 1987.
7. Forray, C., and El-Fakahany, E. E., Mol. Pharmacol., 37, 893–902, 1990.
8. Graziadei, I., Zernig, G., Boer, R., and Glossman, H., Eur. J. Pharmacol. 172, 329–337, 1989.
9. Gross, G., Hanft, G., and Rugevics, C., Eur. J. Pharmacol., 151, 333–335, 1989.
10. Hieble, J. P., Sarau, H. M., Foley, J. J., DeMarinis, R. M., and Pendleton, P. G., Naunyn-Schmiedeberg's Arch. Pharmacol., 318, 267–273, 1982.
11. Langer, S. Z., Pharmacol. Rev., 32, 377–360, 1980.
12. Lomasney, J. W., Cotecchia, S., Lorenz, W., Leung, W.-Y., Schwinn, D. A., Yang-Feng, T. L., Brownstein, M., Lefkowitz, R. J., and Caron, M., J. Biol. Chem., 266, 6365–6369, 1991.
13. Miller, J. and R. N. Germain. J. Exp. Med. 164, 1478–1489 (1986).
14. Minneman, K. P., Pharmacol. Rev., 40, 87–119, 1988.
15. Morrow, A. L., and Creese, I., Mol. Pharmacol., 29, 321–330, 1986.
16. Perez, D. M., M. T. Piascik, and R. M. Graham. Mol. Pharmacol. 40, 876–883 (1991).
17. Sambrook, J., Fritsch, E. F., and Maniatis, T., In: Molecular Cloning: A Laboratory Manual, $2^{nd}$ Edition (Cold Spring Harbor Lab., Cold Spring Harbor, N.Y.), 1989.
18. Sanger, S. Proc. Natl. Acad. Sci. USA 74, 5463–5467 (1977).
19. Sawutz, D. G., S. M. Lanier, C. D. Warren, and R. M. Graham. Mol. Pharmacol. 32, 565–571 (1987).
20. Schwinn, D. A., Lomasney, J. W., Lorenz, W., Szklut, P. J., Fremeau, R. T., Yang-Feng, T. L., Caron, M. G., Lefkowitz, R. J. and Cotecchia, S., J. Biol. Chem., 265, 8183–8189, 1990.
21. Schwinn, D. A., Page, S. A., Middleton, J. P., Lorenz, W., Liggett, S. B., Yamamoto, E., Lapetina, E. G., Caron, M. G., Lefkowitz, R. J., and Cotecchia, S., Mol. Pharmacol., 40, 619–626, 1991.
22. Southern, E. M. J. Mol. Biol. 98, 503–505 (1975). Starke, S., Rev. Physiol. Biochem. Pharmacol., 88, 199–236, 1981.
23. Timmermans, P. B. M. W. M., Karamat Ali, F., Kwa, H. Y., Schoop, A. M. C., Slothorst-Grisdijk, F. P., and van Zwieten, P. A., Mol. Pharmacol., 20, 295–301, 1981.
24. Timmermans, P. B. M. W. M., and Thoolen. M. J. M. C., In: The Alpha-1 Adrenergic Receptors, (ed. by R. R. Ruffolo, Jr., Humana Press, Clifton, N.J.) pp. 113–187, 1987.
25. Voigt, M. M., J. Kispert, and H. Chin. Nucleic Acid Res. 18, 1053 (1990).
26. Weinshank, R. L., Zgombick, J. M., Macchi, M., Adham, N., Lichtblau, H., Branchek, T. A., and Hartig, P. R., Mol. OPharmacol., 38, 681–688, 1990.
27. Cohen, J., (1993) J. Clin. Pharmacol., 33, 272–278.
28. Manning, A. S. and Hearse, D. J., (1984) J. Mol. Cell Cardiol., 16: 497–518.
29. Benfey, B. G., (1992) Can. J. Physiol. Pharmacol., 71: 103–111.
30. Cubeddu, L. X., (1984) American Heart Journal, 116: 133–161.
31. Nishimura, K., Kuwayama, Y., Matsugi, T., Sun, N., and Shirasawa, E., (1993) Investigative Ophthal. & Visual Sci., 34: 1761–1765.
32. Kincaid-Smith, P., (1989) Journal of Human Hypertension, 2743: 75–83.
33. Ames, R. P. and Kiyasu, J. Y., (1989) J. Clin. Pharmacol., 29: 123–127.
34. Pool, J. L., (1991) Am. Heart J., 121: 251–260.
35. Christ, G. J., Schwartz, C. B., Stone, B. A., Parker, M., Janis, M., Gondre, M., Valcic, M., and Melmnan, A., (1992) Amer. Physiological Soc., H15-H20.
36. Rosenthal, J., (1989) Journal of Human Hypertension, 3: 85–91.
37. Kowala, M. C. and Nicolosi, R. J., (1989) Journal of Cardiovascular Pharm., 13: 545–549.

38. Nash, D. T., (1990) Clin. Cardiol., 13: 764–772.
39. Waite, M. A., (1991) Journal of Internal Medicine, 229: 113–117.
40. Achari, R. and Laddu, A., (1992) J. Clin. Pharm., 32: 520–523.
41. Kowala, M. C., Nunnari, J. J., Durham, S. K., and Nicolosi, R. J., (1991) Atherosclerosis, 91: 35–39.
42. Krupp, M. N., Hoover, K. W., and Valentine, J. J., (1989) Journal of Cardiovascular Pharm., 13: 511–519.
43. Jansen, H., Lammers, R., Baggen, M. G. A., and Birkenhager, J. C., (1989) Journal of Cardiovascular Pharm., 13: S5–S10.
44. Joint National Committee on Detection, Evaluation, and Treatment of High Blood Pressure, (1993) Archives of Internal Medicine, 163: 164–183.
45. Sourander, L. B., (1990) Gerontology, 36: 19–25.
46. Empey, D. W. and Medder, K. T., (1988) Drugs, 35: 438–443.
47. Andersson, K. E., (1988) Drugs, 35: 477–494.
48. MacDonald, E., Ruskoaho, H., Scheinen, M. and Virtanen, R., (1988) Annals of Clin. Res., 20: 298–310.
49. Lepor, H., R. Tan, S. Meretyk, and E. Shapiro. Alpha$_1$ adrenoceptor subtypes in the human prostate. J. Urol. 149:640–642 (1993).
50. Lepor, H., S. Auerbach, A Puras-Baez, P. Narayan, M. Soloway, F. Lowe, T. Moon, G. Leifer, and P. Madsen. A randomized, placebo-controlled multicenter study of the efficacy and safety of teazosin in the treatment of benign porstatic hyperplasia. J. Urol. 148:1467–4174 (1992).
51. Price, D. T., R. J. Lefkowitz, M. G. Caron, and D. A. Schwinn. Alpha$_1$-adrenergic receptor mRNA expression in human tissues. FASEB J. 7:A141 (1993).

---

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 2140 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 178..1893
        ( D ) OTHER INFORMATION:

( x i ) SEQUENCE DESCRIPTION: SEQ ID NO:1:

```
CCGGGCCAGG  CACGTCCGCT  CTCGGACAGC  CGCTCCGCGT  CACAGGAACT  TGGGCAGGAC       60

CCGACGGGAC  CCGTGCGCGG  AGCTGCATCT  GGAGCCCCGC  GGCTATGCCC  TGTGCTCCCC      120

TCCTGCCGGC  CGCTCGTTCT  GTGCCCCCGG  CCCGGCCACC  GACGGCCGCG  CGTTGAG        177

ATG  ACT  TTC  CGC  GAT  CTC  CTG  AGC  GTC  AGT  TTC  GAG  GGA  CCC  CGC  CCG   225
Met  Thr  Phe  Arg  Asp  Leu  Leu  Ser  Val  Ser  Phe  Glu  Gly  Pro  Arg  Pro
 1             5                         10                      15

GAC  AGC  AGC  GCA  GGG  GGC  TCC  AGC  GCG  GGC  GGC  GGC  GGG  GGC  AGC  GCG   273
Asp  Ser  Ser  Ala  Gly  Gly  Ser  Ser  Ala  Gly  Gly  Gly  Gly  Gly  Ser  Ala
             20                         25                      30

GGC  GGC  GCG  GCC  CCC  TCG  GAG  GGC  CCG  GCG  GTG  GGC  GGC  GTG  CCG  GGG   321
Gly  Gly  Ala  Ala  Pro  Ser  Glu  Gly  Pro  Ala  Val  Gly  Gly  Val  Pro  Gly
         35                         40                      45

GGC  GCG  GGC  GGC  GGC  GGC  GGC  GTG  GTG  GGC  GCA  GGC  AGC  GGC  GAG  GAC   369
Gly  Ala  Gly  Gly  Gly  Gly  Gly  Val  Val  Gly  Ala  Gly  Ser  Gly  Glu  Asp
     50                         55                      60

AAC  CGG  AGC  TCC  GCG  GGG  GAG  CCG  GGG  AGC  GCG  GGC  GCG  GGC  GGC  GAC   417
Asn  Arg  Ser  Ser  Ala  Gly  Glu  Pro  Gly  Ser  Ala  Gly  Ala  Gly  Gly  Asp
 65                  70                      75                      80

GTG  AAT  GGC  ACG  GCG  GCC  GTC  GGG  GGA  CTG  GTG  GTG  AGC  GCG  CAG  GGC   465
Val  Asn  Gly  Thr  Ala  Ala  Val  Gly  Gly  Leu  Val  Val  Ser  Ala  Gln  Gly
                 85                         90                      95
```

```
GTG GGC GTG GGC GTC TTC CTG GCA GCC TTC ATC CTT ATG GCC GTG GCA    513
Val Gly Val Gly Val Phe Leu Ala Ala Phe Ile Leu Met Ala Val Ala
            100             105             110

GGT AAC CTG CTT GTC ATC CTC TCA GTG GCC TGC AAC CGC CAC CTG CAG    561
Gly Asn Leu Leu Val Ile Leu Ser Val Ala Cys Asn Arg His Leu Gln
        115             120             125

ACC GTC ACC AAC TAT TTC ATC GTG AAC CTG GCC GTG GCC GAC CTG CTG    609
Thr Val Thr Asn Tyr Phe Ile Val Asn Leu Ala Val Ala Asp Leu Leu
    130             135             140

CTG AGC GCC ACC GTA CTG CCC TTC TCG GCC ACC ATG GAG GTT CTG GGC    657
Leu Ser Ala Thr Val Leu Pro Phe Ser Ala Thr Met Glu Val Leu Gly
145             150             155             160

TTC TGG GCC TTT GGC CGC GCC TTC TGC GAC GTA TGG GCC GCC GTG GAC    705
Phe Trp Ala Phe Gly Arg Ala Phe Cys Asp Val Trp Ala Ala Val Asp
                165             170             175

GTG CTG TGC TGC ACG GCC TCC ATC CTC AGC CTC TGC ACC ATC TCC GTG    753
Val Leu Cys Cys Thr Ala Ser Ile Leu Ser Leu Cys Thr Ile Ser Val
            180             185             190

GAC CGG TAC GTG GGC GTG CGC CAC TCA CTC AAG TAC CCA GCC ATC ATG    801
Asp Arg Tyr Val Gly Val Arg His Ser Leu Lys Tyr Pro Ala Ile Met
        195             200             205

ACC GAG CGC AAG GCG GCC GCC ATC CTG GCC CTG CTC TGG GTC GTA GCC    849
Thr Glu Arg Lys Ala Ala Ala Ile Leu Ala Leu Leu Trp Val Val Ala
    210             215             220

CTG GTG GTG TCC GTA GGG CCC CTG CTG GGC TGG AAG GAG CCC GTG CCC    897
Leu Val Val Ser Val Gly Pro Leu Leu Gly Trp Lys Glu Pro Val Pro
225             230             235             240

CCT GAC GAG CGC TTC TGC GGT ATC ACC GAG GAG GCG GGC TAC GCT GTC    945
Pro Asp Glu Arg Phe Cys Gly Ile Thr Glu Glu Ala Gly Tyr Ala Val
                245             250             255

TTC TCC TCC GTG TGC TCC TTC TAC CTG CCC ATG GCG GTC ATC GTG GTC    993
Phe Ser Ser Val Cys Ser Phe Tyr Leu Pro Met Ala Val Ile Val Val
            260             265             270

ATG TAC TGC CGC GTG TAC GTG GTC GCG CGC AGC ACC ACG CGC AGC CTC   1041
Met Tyr Cys Arg Val Tyr Val Val Ala Arg Ser Thr Thr Arg Ser Leu
        275             280             285

GAG GCA GGC GTC AAG CGC GAG CGA GGC AAG GCC TCC GAG GTG GTG CTG   1089
Glu Ala Gly Val Lys Arg Glu Arg Gly Lys Ala Ser Glu Val Val Leu
    290             295             300

CGC ATC CAC TGT CGC GGC GCG GCC ACG GGC GCC GAC GGG GCG CAC GGC   1137
Arg Ile His Cys Arg Gly Ala Ala Thr Gly Ala Asp Gly Ala His Gly
305             310             315             320

ATG CGC AGC GCC AAG GGC CAC ACC TTC CGC AGC TCG CTC TCC GTG CGC   1185
Met Arg Ser Ala Lys Gly His Thr Phe Arg Ser Ser Leu Ser Val Arg
                325             330             335

CTG CTC AAG TTC TCC CGT GAG AAG AAA GCG GCC AAG ACT CTG GCC ATC   1233
Leu Leu Lys Phe Ser Arg Glu Lys Lys Ala Ala Lys Thr Leu Ala Ile
            340             345             350

GTC GTG GGT GTC TTC GTG CTC TGC TGG TTC CCT TTC TTC TTT GTC CTG   1281
Val Val Gly Val Phe Val Leu Cys Trp Phe Pro Phe Phe Phe Val Leu
        355             360             365

CCG CTC GGC TCC TTG TTC CCG CAG CTG AAG CCA TCG GAG GGC GTC TTC   1329
Pro Leu Gly Ser Leu Phe Pro Gln Leu Lys Pro Ser Glu Gly Val Phe
    370             375             380

AAG GTC ATC TTC TGG CTC GGC TAC TTC AAC AGC TGC GTG AAC CCG CTC   1377
Lys Val Ile Phe Trp Leu Gly Tyr Phe Asn Ser Cys Val Asn Pro Leu
385             390             395             400

ATC TAC CCC TGT TCC AGC CGC GAG TTC AAG CGC GCC TTC CTC CGT CTC   1425
Ile Tyr Pro Cys Ser Ser Arg Glu Phe Lys Arg Ala Phe Leu Arg Leu
                405             410             415
```

-continued

| | | | | | | | | | | | | | | | | |
|---|---|---|---|---|---|---|---|---|---|---|---|---|---|---|---|---|
| CTG | CGC | TGC | CAG | TGC | CGT | CGT | CGC | CGG | CGC | CGC | CGC | CCT | CTC | TGG | CGT | 1473 |
| Leu | Arg | Cys | Gln<br>420 | Cys | Arg | Arg | Arg | Arg<br>425 | Arg | Arg | Arg | Pro | Leu<br>430 | Trp | Arg | |
| GTC | TAC | GGC | CAC | CAC | TGG | CGG | GCC | TCC | ACC | AGC | GGC | CTG | CGC | CAG | GAC | 1521 |
| Val | Tyr | Gly<br>435 | His | His | Trp | Arg | Ala | Ser<br>440 | Thr | Ser | Gly | Leu<br>445 | Arg | Gln | Asp | |
| TGC | GCC | CCG | AGT | TCG | GGC | GAC | GCG | CCC | CCC | GGA | GCG | CCG | CTG | GCC | CTC | 1569 |
| Cys | Ala<br>450 | Pro | Ser | Ser | Gly | Asp<br>455 | Ala | Pro | Pro | Gly | Ala<br>460 | Pro | Leu | Ala | Leu | |
| ACC | GCG | CTC | CCC | GAC | CCC | GAC | CCC | GAA | CCC | CCA | GGC | ACG | CCC | GAG | ATG | 1617 |
| Thr<br>465 | Ala | Leu | Pro | Asp<br>470 | Pro | Asp | Pro | Glu | Pro<br>475 | Pro | Gly | Thr | Pro | Glu | Met<br>480 | |
| CAG | GCT | CCG | GTC | GCC | AGC | CGT | CGA | AAG | CCA | CCC | AGC | GCC | TTC | CGC | GAG | 1665 |
| Gln | Ala | Pro | Val | Ala<br>485 | Ser | Arg | Arg | Lys | Pro<br>490 | Pro | Ser | Ala | Phe | Arg<br>495 | Glu | |
| TGG | AGG | CTG | CTG | GGG | CCG | TTC | CGG | AGA | CCC | ACG | ACC | CAG | CTG | CGC | GCC | 1713 |
| Trp | Arg | Leu | Leu<br>500 | Gly | Pro | Phe | Arg | Arg<br>505 | Pro | Thr | Thr | Gln | Leu<br>510 | Arg | Ala | |
| AAA | GTC | TCC | AGC | CTG | TCG | CAC | AAG | ATC | CGC | GCC | GGG | GGC | GCG | CAG | CGC | 1761 |
| Lys | Val | Ser<br>515 | Ser | Leu | Ser | His | Lys<br>520 | Ile | Arg | Ala | Gly | Gly<br>525 | Ala | Gln | Arg | |
| GCA | GAG | GCA | GCG | TGC | GCC | CAG | CGC | TCA | GAG | GTG | GAG | GCT | GTG | TCC | CTA | 1809 |
| Ala | Glu<br>530 | Ala | Ala | Cys | Ala | Gln<br>535 | Arg | Ser | Glu | Val | Glu<br>540 | Ala | Val | Ser | Leu | |
| GGC | GTC | CCA | CAC | GAG | GTG | GCC | GAG | GGC | GCC | ACC | TGC | CAG | GCC | TAC | GAA | 1857 |
| Gly<br>545 | Val | Pro | His | Glu | Val<br>550 | Ala | Glu | Gly | Ala | Thr<br>555 | Cys | Gln | Ala | Tyr | Glu<br>560 | |
| TTG | GCC | GAC | TAC | AGC | AAC | CTA | CGG | GAG | ACC | GAT | ATT | TAAGGACCCC | | | | 1903 |
| Leu | Ala | Asp | Tyr | Ser<br>565 | Asn | Leu | Arg | Glu<br>570 | Thr | Asp | Ile | | | | | |

AGAGCTAGGC CGCGGAGTGT GCTGGGCTTG GGGGTAAGGG GGACCAGAGA GGCGGGCTGG 1963

TGTTCTAAGA GCCCCGTGC AAATCGGAGA CCCGGAAACT GATCAGGGCA GCTGCTCTGT 2023

GACATCCCTG AGGAACTGGG CAGAGCTTGA GGCTGGAGCC CTTGAAAGGT GAAAAGTAGT 2083

GGGGCCCCCT GCTGGACTCA GGTGCCCAGA ACTCTTTTCT TAGAAGGGAG AGGCTGC 2140

( 2 ) INFORMATION FOR SEQ ID NO:2:

( i ) SEQUENCE CHARACTERISTICS:
        ( A ) LENGTH: 572 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met<br>1 | Thr | Phe | Arg | Asp<br>5 | Leu | Leu | Ser | Val | Ser<br>10 | Phe | Glu | Gly | Pro | Arg | Pro<br>15 |
| Asp | Ser | Ser | Ala<br>20 | Gly | Gly | Ser | Ser | Ala<br>25 | Gly | Gly | Gly | Gly | Ser<br>30 | Ala | |
| Gly | Gly | Ala | Ala<br>35 | Pro | Ser | Glu | Gly | Pro<br>40 | Ala | Val | Gly | Gly | Val<br>45 | Pro | Gly |
| Gly | Ala<br>50 | Gly | Gly | Gly | Gly | Gly<br>55 | Val | Val | Gly | Ala<br>60 | Gly | Ser | Gly | Glu | Asp |
| Asn<br>65 | Arg | Ser | Ser | Ala | Gly<br>70 | Glu | Pro | Gly | Ser | Ala<br>75 | Gly | Ala | Gly | Gly | Asp<br>80 |
| Val | Asn | Gly | Thr | Ala<br>85 | Ala | Val | Gly | Gly | Leu<br>90 | Val | Val | Ser | Ala<br>95 | Gln | Gly |
| Val | Gly | Val | Gly<br>100 | Val | Phe | Leu | Ala | Ala<br>105 | Phe | Ile | Leu | Met<br>110 | Ala | Val | Ala |

```
Gly  Asn  Leu  Leu  Val  Ile  Leu  Ser  Val  Ala  Cys  Asn  Arg  His  Leu  Gln
          115                      120                      125

Thr  Val  Thr  Asn  Tyr  Phe  Ile  Val  Asn  Leu  Ala  Val  Ala  Asp  Leu  Leu
     130                      135                      140

Leu  Ser  Ala  Thr  Val  Leu  Pro  Phe  Ser  Ala  Thr  Met  Glu  Val  Leu  Gly
145                      150                      155                      160

Phe  Trp  Ala  Phe  Gly  Arg  Ala  Phe  Cys  Asp  Val  Trp  Ala  Ala  Val  Asp
                    165                      170                      175

Val  Leu  Cys  Cys  Thr  Ala  Ser  Ile  Leu  Ser  Leu  Cys  Thr  Ile  Ser  Val
               180                      185                      190

Asp  Arg  Tyr  Val  Gly  Val  Arg  His  Ser  Leu  Lys  Tyr  Pro  Ala  Ile  Met
          195                      200                      205

Thr  Glu  Arg  Lys  Ala  Ala  Ala  Ile  Leu  Ala  Leu  Leu  Trp  Val  Val  Ala
     210                      215                      220

Leu  Val  Val  Ser  Val  Gly  Pro  Leu  Leu  Gly  Trp  Lys  Glu  Pro  Val  Pro
225                      230                      235                      240

Pro  Asp  Glu  Arg  Phe  Cys  Gly  Ile  Thr  Glu  Glu  Ala  Gly  Tyr  Ala  Val
                    245                      250                      255

Phe  Ser  Ser  Val  Cys  Ser  Phe  Tyr  Leu  Pro  Met  Ala  Val  Ile  Val  Val
               260                      265                      270

Met  Tyr  Cys  Arg  Val  Tyr  Val  Val  Ala  Arg  Ser  Thr  Thr  Arg  Ser  Leu
          275                      280                      285

Glu  Ala  Gly  Val  Lys  Arg  Glu  Arg  Gly  Lys  Ala  Ser  Glu  Val  Val  Leu
     290                      295                      300

Arg  Ile  His  Cys  Arg  Gly  Ala  Ala  Thr  Gly  Ala  Asp  Gly  Ala  His  Gly
305                      310                      315                      320

Met  Arg  Ser  Ala  Lys  Gly  His  Thr  Phe  Arg  Ser  Ser  Leu  Ser  Val  Arg
               325                      330                      335

Leu  Leu  Lys  Phe  Ser  Arg  Glu  Lys  Lys  Ala  Ala  Lys  Thr  Leu  Ala  Ile
               340                      345                      350

Val  Val  Gly  Val  Phe  Val  Leu  Cys  Trp  Phe  Pro  Phe  Phe  Phe  Val  Leu
          355                      360                      365

Pro  Leu  Gly  Ser  Leu  Phe  Pro  Gln  Leu  Lys  Pro  Ser  Glu  Gly  Val  Phe
370                      375                      380

Lys  Val  Ile  Phe  Trp  Leu  Gly  Tyr  Phe  Asn  Ser  Cys  Val  Asn  Pro  Leu
385                      390                      395                      400

Ile  Tyr  Pro  Cys  Ser  Ser  Arg  Glu  Phe  Lys  Arg  Ala  Phe  Leu  Arg  Leu
               405                      410                      415

Leu  Arg  Cys  Gln  Cys  Arg  Arg  Arg  Arg  Arg  Arg  Arg  Pro  Leu  Trp  Arg
               420                      425                      430

Val  Tyr  Gly  His  His  Trp  Arg  Ala  Ser  Thr  Ser  Gly  Leu  Arg  Gln  Asp
          435                      440                      445

Cys  Ala  Pro  Ser  Ser  Gly  Asp  Ala  Pro  Gly  Ala  Pro  Leu  Ala  Leu
     450                      455                      460

Thr  Ala  Leu  Pro  Asp  Pro  Asp  Pro  Glu  Pro  Pro  Gly  Thr  Pro  Glu  Met
465                      470                      475                      480

Gln  Ala  Pro  Val  Ala  Ser  Arg  Arg  Lys  Pro  Pro  Ser  Ala  Phe  Arg  Glu
                    485                      490                      495

Trp  Arg  Leu  Leu  Gly  Pro  Phe  Arg  Arg  Pro  Thr  Thr  Gln  Leu  Arg  Ala
               500                      505                      510

Lys  Val  Ser  Ser  Leu  Ser  His  Lys  Ile  Arg  Ala  Gly  Gly  Ala  Gln  Arg
          515                      520                      525

Ala  Glu  Ala  Ala  Cys  Ala  Gln  Arg  Ser  Glu  Val  Glu  Ala  Val  Ser  Leu
```

```
                        530                         535                         540
Gly  Val  Pro  His  Glu  Val  Ala  Glu  Gly  Ala  Thr  Cys  Gln  Ala  Tyr  Glu
545                      550                         555                         560

Leu  Ala  Asp  Tyr  Ser  Asn  Leu  Arg  Glu  Thr  Asp  Ile
                    565                      570
```

( 2 ) INFORMATION FOR SEQ ID NO:3:

( i ) SEQUENCE CHARACTERISTICS:
        ( A ) LENGTH: 1738 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 124..1683
        ( D ) OTHER INFORMATION:

( x i ) SEQUENCE DESCRIPTION: SEQ ID NO:3:

```
GCCAGGAGGG  CGCCTCTGGG  AAGAAGACCA  CGGGGGAAGC  AAAGTTTCAG  GGCAGCTGAG          60

GAGCCTTCGC  CGCAGCCCTT  CCGAGCCCAA  TCATCCCCCA  GGCTATGGAG  GGCGGACTCT         120

AAG  ATG  AAT  CCC  GAC  CTG  GAC  ACC  GGC  CAC  AAC  ACA  TCA  GCA  CCT  GCC    168
     Met  Asn  Pro  Asp  Leu  Asp  Thr  Gly  His  Asn  Thr  Ser  Ala  Pro  Ala
     1              5                        10                       15

CAC  TGG  GGA  GAG  TTG  AAA  AAT  GCC  AAC  TTC  ACT  GGC  CCC  AAC  CAG  ACC    216
His  Trp  Gly  Glu  Leu  Lys  Asn  Ala  Asn  Phe  Thr  Gly  Pro  Asn  Gln  Thr
                    20                       25                       30

TCG  AGC  AAC  TCC  ACA  CTG  CCC  CAG  CTG  GAC  ATC  ACC  AGG  GCC  ATC  TCT    264
Ser  Ser  Asn  Ser  Thr  Leu  Pro  Gln  Leu  Asp  Ile  Thr  Arg  Ala  Ile  Ser
               35                       40                       45

GTG  GGC  CTG  GTG  CTG  GGC  GCC  TTC  ATC  CTC  TTT  GCC  ATC  GTG  GGC  AAC    312
Val  Gly  Leu  Val  Leu  Gly  Ala  Phe  Ile  Leu  Phe  Ala  Ile  Val  Gly  Asn
          50                       55                       60

ATC  CTA  GTC  ATC  TTG  TCT  GTG  GCC  TGC  AAC  CGG  CAC  CTG  CGG  ACG  CCC    360
Ile  Leu  Val  Ile  Leu  Ser  Val  Ala  Cys  Asn  Arg  His  Leu  Arg  Thr  Pro
     65                       70                       75

ACC  AAC  TAC  TTC  ATT  GTC  AAC  CTG  GCC  ATG  GCC  GAC  CTG  CTG  TTG  AGC    408
Thr  Asn  Tyr  Phe  Ile  Val  Asn  Leu  Ala  Met  Ala  Asp  Leu  Leu  Leu  Ser
80                       85                       90                       95

TTC  ACC  GTC  CTG  CCC  TTC  TCA  GCG  GCC  CTA  GAG  GTG  CTC  GGC  TAC  TGG    456
Phe  Thr  Val  Leu  Pro  Phe  Ser  Ala  Ala  Leu  Glu  Val  Leu  Gly  Tyr  Trp
                    100                      105                      110

GTG  CTG  GGG  CGG  ATC  TTC  TGT  GAC  ATC  TGG  GCA  GCC  GTG  GAT  GTC  CTG    504
Val  Leu  Gly  Arg  Ile  Phe  Cys  Asp  Ile  Trp  Ala  Ala  Val  Asp  Val  Leu
               115                      120                      125

TGC  TGC  ACA  GCG  TCC  ATT  CTG  AGC  CTG  TGC  GCC  ATC  TCC  ATC  GAT  CGC    552
Cys  Cys  Thr  Ala  Ser  Ile  Leu  Ser  Leu  Cys  Ala  Ile  Ser  Ile  Asp  Arg
          130                      135                      140

TAC  ATC  GGG  GTG  CGC  TAC  TCT  CTG  CAG  TAT  CCC  ACG  CTG  GTC  ACC  CGG    600
Tyr  Ile  Gly  Val  Arg  Tyr  Ser  Leu  Gln  Tyr  Pro  Thr  Leu  Val  Thr  Arg
     145                      150                      155

AGG  AAG  GCC  ATC  TTG  GCG  CTG  CTC  AGT  GTC  TGG  GTC  TTG  TCC  ACC  GTC    648
Arg  Lys  Ala  Ile  Leu  Ala  Leu  Leu  Ser  Val  Trp  Val  Leu  Ser  Thr  Val
160                      165                      170                      175

ATC  TCC  ATC  GGG  CCT  CTC  CTT  GGG  TGG  AAG  GAG  CCG  GCA  CCC  AAC  GAT    696
Ile  Ser  Ile  Gly  Pro  Leu  Leu  Gly  Trp  Lys  Glu  Pro  Ala  Pro  Asn  Asp
```

-continued

```
                          180                              185                              190
GAC   AAG   GAG   TGC   GGG   GTC   ACC   GAA   GAA   CCC   TTC   TAT   GCC   CTC   TTC   TCC      744
Asp   Lys   Glu   Cys   Gly   Val   Thr   Glu   Glu   Pro   Phe   Tyr   Ala   Leu   Phe   Ser
                  195                     200                           205

TCT   CTG   GGC   TCC   TTC   TAC   ATC   CCT   CTG   GCG   GTC   ATT   CTA   GTC   ATG   TAC      792
Ser   Leu   Gly   Ser   Phe   Tyr   Ile   Pro   Leu   Ala   Val   Ile   Leu   Val   Met   Tyr
            210                     215                           220

TGC   CGT   GTC   TAT   ATA   GTG   GCC   AAG   AGA   ACC   ACC   AAG   AAC   CTA   GAG   GCA      840
Cys   Arg   Val   Tyr   Ile   Val   Ala   Lys   Arg   Thr   Thr   Lys   Asn   Leu   Glu   Ala
      225                           230                           235

GGA   GTC   ATG   AAG   GAG   ATG   TCC   AAC   TCC   AAG   GAG   CTG   ACC   CTG   AGG   ATC      888
Gly   Val   Met   Lys   Glu   Met   Ser   Asn   Ser   Lys   Glu   Leu   Thr   Leu   Arg   Ile
240                           245                           250                           255

CAT   TCC   AAG   AAC   TTT   CAC   GAG   GAC   ACC   CTT   AGC   AGT   ACC   AAG   GCC   AAG      936
His   Ser   Lys   Asn   Phe   His   Glu   Asp   Thr   Leu   Ser   Ser   Thr   Lys   Ala   Lys
                              260                           265                           270

GGC   CAC   AAC   CCC   AGG   AGT   TCC   ATA   GCT   GTC   AAA   CTT   TTT   AAG   TTC   TCC      984
Gly   His   Asn   Pro   Arg   Ser   Ser   Ile   Ala   Val   Lys   Leu   Phe   Lys   Phe   Ser
                  275                           280                           285

AGG   GAA   AAG   AAA   GCA   GCT   AAG   ACG   TTG   GGC   ATT   GTG   GTC   GGT   ATG   TTC     1032
Arg   Glu   Lys   Lys   Ala   Ala   Lys   Thr   Leu   Gly   Ile   Val   Val   Gly   Met   Phe
                  290                           295                           300

ATC   TTG   TGC   TGG   CTA   CCC   TTC   TTC   ATC   GCT   CTA   CCG   CTT   GGC   TCC   TTG     1080
Ile   Leu   Cys   Trp   Leu   Pro   Phe   Phe   Ile   Ala   Leu   Pro   Leu   Gly   Ser   Leu
305                           310                           315

TTC   TCC   ACC   CTG   AAG   CCC   CCC   GAC   GCC   GTG   TTC   AAG   GTG   GTG   TTC   TGG     1128
Phe   Ser   Thr   Leu   Lys   Pro   Pro   Asp   Ala   Val   Phe   Lys   Val   Val   Phe   Trp
320                           325                           330                           335

CTG   GGC   TAC   TTC   AAC   AGC   TGC   CTC   AAC   CCC   ATC   ATC   TAC   CCA   TGC   TCC     1176
Leu   Gly   Tyr   Phe   Asn   Ser   Cys   Leu   Asn   Pro   Ile   Ile   Tyr   Pro   Cys   Ser
                              340                           345                           350

AGC   AAG   GAG   TTC   AAG   CGC   GCT   TTC   GTG   CGC   ATC   CTC   GGG   TGC   CAG   TGC     1224
Ser   Lys   Glu   Phe   Lys   Arg   Ala   Phe   Val   Arg   Ile   Leu   Gly   Cys   Gln   Cys
                  355                           360                           365

CGC   GGC   CGC   GGC   CGC   CGC   CGA   CGC   CGC   CGC   CGT   CGC   CTG   GGC   GGC            1272
Arg   Gly   Arg   Gly   Arg   Arg   Arg   Arg   Arg   Arg   Arg   Arg   Leu   Gly   Gly
                  370                           375                           380

TGC   GCC   TAC   ACC   TAC   CGG   CCG   TGG   ACG   CGC   GGC   GGC   TCG   CTG   GAG   CGC     1320
Cys   Ala   Tyr   Thr   Tyr   Arg   Pro   Trp   Thr   Arg   Gly   Gly   Ser   Leu   Glu   Arg
385                           390                           395

TCG   CAG   TCG   CGC   AAG   GAC   TCG   CTG   GAC   GAC   AGC   GGC   AGC   TGC   CTG   AGC     1368
Ser   Gln   Ser   Arg   Lys   Asp   Ser   Leu   Asp   Asp   Ser   Gly   Ser   Cys   Leu   Ser
400                           405                           410                           415

GGC   AGC   CAG   CGG   ACC   CTG   CCC   TCG   GCC   TCG   CCG   AGC   CCG   GGC   TAC   CTG     1416
Gly   Ser   Gln   Arg   Thr   Leu   Pro   Ser   Ala   Ser   Pro   Ser   Pro   Gly   Tyr   Leu
                        420                           425                           430

GGC   CGC   GGC   GCG   CCA   CCG   CCA   GTC   GAG   CTG   TGC   GCC   TTC   CCC   GAG   TGG     1464
Gly   Arg   Gly   Ala   Pro   Pro   Pro   Val   Glu   Leu   Cys   Ala   Phe   Pro   Glu   Trp
                        435                           440                           445

AAG   GCG   CCC   GGC   GCC   CTC   CTG   AGC   CTG   CCC   GCG   CCT   GAG   CCC   CCC   GGC     1512
Lys   Ala   Pro   Gly   Ala   Leu   Leu   Ser   Leu   Pro   Ala   Pro   Glu   Pro   Pro   Gly
                  450                           455                           460

CGC   CGC   GGC   CGC   CAC   GAC   TCG   GGC   CCG   CTC   TTC   ACC   TTC   AAG   CTC   CTG     1560
Arg   Arg   Gly   Arg   His   Asp   Ser   Gly   Pro   Leu   Phe   Thr   Phe   Lys   Leu   Leu
465                           470                           475

ACC   GAG   CCC   GAG   AGC   CCC   GGG   ACC   GAC   GGC   GGC   GCC   AGC   AAC   GGA   GGC     1608
Thr   Glu   Pro   Glu   Ser   Pro   Gly   Thr   Asp   Gly   Gly   Ala   Ser   Asn   Gly   Gly
480                           485                           490                           495

TGC   GAG   GCC   GCG   GCC   GAC   GTG   GCC   AAC   GGG   CAG   CCG   GGC   TTC   AAA   AGC     1656
Cys   Glu   Ala   Ala   Ala   Asp   Val   Ala   Asn   Gly   Gln   Pro   Gly   Phe   Lys   Ser
```

```
                         500                        505                       510
AAC  ATG  CCC  CTG  GCG  CCC  GGG  CAG  TTT  TAGGGCCCCC  GTGCGCAGCT                    1703
Asn  Met  Pro  Leu  Ala  Pro  Gly  Gln  Phe
               515                      520

TTCTTTCCCT  GGGGAGGAAA  ACATCGTGGG  GGGGA                                              1738
```

( 2 ) INFORMATION FOR SEQ ID NO:4:

( i ) SEQUENCE CHARACTERISTICS:
        ( A ) LENGTH: 520 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Asn  Pro  Asp  Leu  Asp  Thr  Gly  His  Asn  Thr  Ser  Ala  Pro  Ala  His
 1                   5                        10                       15

Trp  Gly  Glu  Leu  Lys  Asn  Ala  Asn  Phe  Thr  Gly  Pro  Asn  Gln  Thr  Ser
               20                       25                       30

Ser  Asn  Ser  Thr  Leu  Pro  Gln  Leu  Asp  Ile  Thr  Arg  Ala  Ile  Ser  Val
          35                        40                       45

Gly  Leu  Val  Leu  Gly  Ala  Phe  Ile  Leu  Phe  Ala  Ile  Val  Gly  Asn  Ile
     50                        55                       60

Leu  Val  Ile  Leu  Ser  Val  Ala  Cys  Asn  Arg  His  Leu  Arg  Thr  Pro  Thr
65                        70                       75                       80

Asn  Tyr  Phe  Ile  Val  Asn  Leu  Ala  Met  Ala  Asp  Leu  Leu  Leu  Ser  Phe
                    85                       90                       95

Thr  Val  Leu  Pro  Phe  Ser  Ala  Ala  Leu  Glu  Val  Leu  Gly  Tyr  Trp  Val
               100                      105                      110

Leu  Gly  Arg  Ile  Phe  Cys  Asp  Ile  Trp  Ala  Ala  Val  Asp  Val  Leu  Cys
          115                      120                      125

Cys  Thr  Ala  Ser  Ile  Leu  Ser  Leu  Cys  Ala  Ile  Ser  Ile  Asp  Arg  Tyr
     130                      135                      140

Ile  Gly  Val  Arg  Tyr  Ser  Leu  Gln  Tyr  Pro  Thr  Leu  Val  Thr  Arg  Arg
145                      150                      155                      160

Lys  Ala  Ile  Leu  Ala  Leu  Leu  Ser  Val  Trp  Val  Leu  Ser  Thr  Val  Ile
                    165                      170                      175

Ser  Ile  Gly  Pro  Leu  Leu  Gly  Trp  Lys  Glu  Pro  Ala  Pro  Asn  Asp  Asp
               180                      185                      190

Lys  Glu  Cys  Gly  Val  Thr  Glu  Glu  Pro  Phe  Tyr  Ala  Leu  Phe  Ser  Ser
          195                      200                      205

Leu  Gly  Ser  Phe  Tyr  Ile  Pro  Leu  Ala  Val  Ile  Leu  Val  Met  Tyr  Cys
     210                      215                      220

Arg  Val  Tyr  Ile  Val  Ala  Lys  Arg  Thr  Thr  Lys  Asn  Leu  Glu  Ala  Gly
225                      230                      235                      240

Val  Met  Lys  Glu  Met  Ser  Asn  Ser  Lys  Glu  Leu  Thr  Leu  Arg  Ile  His
                    245                      250                      255

Ser  Lys  Asn  Phe  His  Glu  Asp  Thr  Leu  Ser  Ser  Thr  Lys  Ala  Lys  Gly
               260                      265                      270

His  Asn  Pro  Arg  Ser  Ser  Ile  Ala  Val  Lys  Leu  Phe  Lys  Phe  Ser  Arg
          275                      280                      285

Glu  Lys  Lys  Ala  Ala  Lys  Thr  Leu  Gly  Ile  Val  Val  Gly  Met  Phe  Ile
     290                      295                      300

Leu  Cys  Trp  Leu  Pro  Phe  Phe  Ile  Ala  Leu  Pro  Leu  Gly  Ser  Leu  Phe
305                      310                      315                      320
```

| | | | | | | | | | | | | | | |
|---|---|---|---|---|---|---|---|---|---|---|---|---|---|---|
| Ser | Thr | Leu | Lys | Pro 325 | Pro | Asp | Ala | Val | Phe 330 | Lys | Val | Val | Phe | Leu 335 |
| Gly | Tyr | Phe | Asn 340 | Ser | Cys | Leu | Asn | Pro 345 | Ile | Ile | Tyr | Pro | Cys 350 | Ser | Ser |
| Lys | Glu | Phe 355 | Lys | Arg | Ala | Phe | Val 360 | Arg | Ile | Leu | Gly | Cys 365 | Gln | Cys | Arg |
| Gly | Arg 370 | Gly | Arg | Arg | Arg | Arg 375 | Arg | Arg | Arg | Arg 380 | Leu | Gly | Gly | Cys |
| Ala 385 | Tyr | Thr | Tyr | Arg | Pro 390 | Trp | Thr | Arg | Gly | Gly 395 | Ser | Leu | Glu | Arg | Ser 400 |
| Gln | Ser | Arg | Lys | Asp 405 | Ser | Leu | Asp | Asp | Ser 410 | Gly | Ser | Cys | Leu | Ser 415 | Gly |
| Ser | Gln | Arg | Thr 420 | Leu | Pro | Ser | Ala | Ser 425 | Pro | Ser | Pro | Gly | Tyr 430 | Leu | Gly |
| Arg | Gly | Ala 435 | Pro | Pro | Pro | Val | Glu 440 | Leu | Cys | Ala | Phe | Pro 445 | Glu | Trp | Lys |
| Ala | Pro 450 | Gly | Ala | Leu | Leu | Ser 455 | Leu | Pro | Ala | Pro | Glu 460 | Pro | Pro | Gly | Arg |
| Arg 465 | Gly | Arg | His | Asp | Ser 470 | Gly | Pro | Leu | Phe | Thr 475 | Phe | Lys | Leu | Leu | Thr 480 |
| Glu | Pro | Glu | Ser | Pro 485 | Gly | Thr | Asp | Gly | Gly 490 | Ala | Ser | Asn | Gly | Gly 495 | Cys |
| Glu | Ala | Ala | Ala 500 | Asp | Val | Ala | Asn | Gly 505 | Gln | Pro | Gly | Phe | Lys 510 | Ser | Asn |
| Met | Pro | Leu 515 | Ala | Pro | Gly | Gln | Phe 520 | | | | | | | | |

( 2 ) INFORMATION FOR SEQ ID NO:5:

( i ) SEQUENCE CHARACTERISTICS:
        ( A ) LENGTH: 1639 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 126..1523
        ( D ) OTHER INFORMATION:

( x i ) SEQUENCE DESCRIPTION: SEQ ID NO:5:

```
CCAGCCAAAC CACTGGCAGG CTCCCTCCAG CCGAGACCTT TTATTCCCGG CTCCCGAGCT        60

CCGCCTCCGC GCCAGCCCGG GAGGTGGCCC TGACAGCCGG ACCTCGCCCG GCCCCGGCTG       120

GGACC ATG GTG TTT CTC TCG GGA AAT GCT TCC GAC AGC TCC AAC TGC          167
      Met Val Phe Leu Ser Gly Asn Ala Ser Asp Ser Ser Asn Cys
        1               5                  10

ACC CAA CCG CCG GCA CCG GTG AAC ATT TCC AAG GCC ATT CTG CTC GGG        215
Thr Gln Pro Pro Ala Pro Val Asn Ile Ser Lys Ala Ile Leu Leu Gly
 15           20                  25                          30

GTG ATC TTG GGG GGC CTC ATT CTT TTC GGG GTG CTG GGT AAC ATC CTA        263
Val Ile Leu Gly Gly Leu Ile Leu Phe Gly Val Leu Gly Asn Ile Leu
             35                  40                      45

GTG ATC CTC TCC GTA GCC TGT CAC CGA CAC CTG CAC TCA GTC ACG CAC        311
Val Ile Leu Ser Val Ala Cys His Arg His Leu His Ser Val Thr His
         50                  55                      60
```

-continued

| | | | | | | | | | | | | | | | | |
|---|---|---|---|---|---|---|---|---|---|---|---|---|---|---|---|---|
| TAC | TAC | ATC | GTC | AAC | CTG | GCG | GTG | GCC | GAC | CTC | CTG | CTC | ACC | TCC | ACG | 359 |
| Tyr | Tyr | Ile | Val | Asn | Leu | Ala | Val | Ala | Asp | Leu | Leu | Leu | Thr | Ser | Thr | |
| | | 65 | | | | | 70 | | | | | 75 | | | | |
| GTG | CTG | CCC | TTC | TCC | GCC | ATC | TTC | GAG | GTC | CTA | GGC | TAC | TGG | GCC | TTC | 407 |
| Val | Leu | Pro | Phe | Ser | Ala | Ile | Phe | Glu | Val | Leu | Gly | Tyr | Trp | Ala | Phe | |
| | | 80 | | | | | 85 | | | | | 90 | | | | |
| GGC | AGG | GTC | TTC | TGC | AAC | ATC | TGG | GCG | GCA | GTG | GAT | GTG | CTG | TGC | TGC | 455 |
| Gly | Arg | Val | Phe | Cys | Asn | Ile | Trp | Ala | Ala | Val | Asp | Val | Leu | Cys | Cys | |
| 95 | | | | | 100 | | | | | 105 | | | | | 110 | |
| ACC | GCG | TCC | ATC | ATG | GGC | CTC | TGC | ATC | ATC | TCC | ATC | GAC | CGC | TAC | ATC | 503 |
| Thr | Ala | Ser | Ile | Met | Gly | Leu | Cys | Ile | Ile | Ser | Ile | Asp | Arg | Tyr | Ile | |
| | | | | 115 | | | | | 120 | | | | | 125 | | |
| GGC | GTG | AGC | TAC | CCG | CTG | CGC | TAC | CCA | ACC | ATC | GTC | ACC | CAG | AGG | AGG | 551 |
| Gly | Val | Ser | Tyr | Pro | Leu | Arg | Tyr | Pro | Thr | Ile | Val | Thr | Gln | Arg | Arg | |
| | | | 130 | | | | | 135 | | | | | 140 | | | |
| GGT | CTC | ATG | GCT | CTG | CTC | TGC | GTC | TGG | GCA | CTC | TCC | CTG | GTC | ATA | TCC | 599 |
| Gly | Leu | Met | Ala | Leu | Leu | Cys | Val | Trp | Ala | Leu | Ser | Leu | Val | Ile | Ser | |
| | | | 145 | | | | | 150 | | | | | 155 | | | |
| ATT | GGA | CCC | CTG | TTC | GGC | TGG | AGG | CAG | CCG | GCC | CCC | GAG | GAC | GAG | ACC | 647 |
| Ile | Gly | Pro | Leu | Phe | Gly | Trp | Arg | Gln | Pro | Ala | Pro | Glu | Asp | Glu | Thr | |
| | 160 | | | | | 165 | | | | | 170 | | | | | |
| ATC | TGC | CAG | ATC | AAC | GAG | GAG | CCG | GGC | TAC | GTG | CTC | TTC | TCA | GCG | CTG | 695 |
| Ile | Cys | Gln | Ile | Asn | Glu | Glu | Pro | Gly | Tyr | Val | Leu | Phe | Ser | Ala | Leu | |
| 175 | | | | | 180 | | | | | 185 | | | | | 190 | |
| GGC | TCC | TTC | TAC | CTG | CCT | CTG | GCC | ATC | ATC | CTG | GTC | ATG | TAC | TGC | CGC | 743 |
| Gly | Ser | Phe | Tyr | Leu | Pro | Leu | Ala | Ile | Ile | Leu | Val | Met | Tyr | Cys | Arg | |
| | | | | 195 | | | | | 200 | | | | | 205 | | |
| GTC | TAC | GTG | GTG | GCC | AAG | AGG | GAG | AGC | CGG | GGC | CTC | AAG | TCT | GGC | CTC | 791 |
| Val | Tyr | Val | Val | Ala | Lys | Arg | Glu | Ser | Arg | Gly | Leu | Lys | Ser | Gly | Leu | |
| | | | 210 | | | | | 215 | | | | | 220 | | | |
| AAG | ACC | GAC | AAG | TCG | GAC | TCG | GAG | CAA | GTG | ACG | CTC | CGC | ATC | CAT | CGG | 839 |
| Lys | Thr | Asp | Lys | Ser | Asp | Ser | Glu | Gln | Val | Thr | Leu | Arg | Ile | His | Arg | |
| | | | 225 | | | | | 230 | | | | | 235 | | | |
| AAA | AAC | GCC | CCG | GCA | GGA | GGC | AGC | GGG | ATG | GCC | AGC | GCC | AAG | ACC | AAG | 887 |
| Lys | Asn | Ala | Pro | Ala | Gly | Gly | Ser | Gly | Met | Ala | Ser | Ala | Lys | Thr | Lys | |
| | 240 | | | | | 245 | | | | | 250 | | | | | |
| ACG | CAC | TTC | TCA | GTG | AGG | CTC | CTC | AAG | TTC | TCC | CGG | GAG | AAG | AAA | GCG | 935 |
| Thr | His | Phe | Ser | Val | Arg | Leu | Leu | Lys | Phe | Ser | Arg | Glu | Lys | Lys | Ala | |
| 255 | | | | | 260 | | | | | 265 | | | | | 270 | |
| GCC | AAA | ACG | CTG | GGC | ATC | GTG | GTC | GGC | TGC | TTC | GTC | CTC | TGC | TGG | CTG | 983 |
| Ala | Lys | Thr | Leu | Gly | Ile | Val | Val | Gly | Cys | Phe | Val | Leu | Cys | Trp | Leu | |
| | | | | 275 | | | | | 280 | | | | | 285 | | |
| CCT | TTT | TTC | TTA | GTC | ATG | CCC | ATT | GGG | TCT | TTC | TTC | CCT | GAT | TTC | AAG | 1031 |
| Pro | Phe | Phe | Leu | Val | Met | Pro | Ile | Gly | Ser | Phe | Phe | Pro | Asp | Phe | Lys | |
| | | | 290 | | | | | 295 | | | | | 300 | | | |
| CCC | TCT | GAA | ACA | GTT | TTT | AAA | ATA | GTA | TTT | TGG | CTC | GGA | TAT | CTA | AAC | 1079 |
| Pro | Ser | Glu | Thr | Val | Phe | Lys | Ile | Val | Phe | Trp | Leu | Gly | Tyr | Leu | Asn | |
| | | 305 | | | | | 310 | | | | | 315 | | | | |
| AGC | TGC | ATC | AAC | CCC | ATC | ATA | TAC | CCA | TGC | TCC | AGC | CAA | GAG | TTC | AAA | 1127 |
| Ser | Cys | Ile | Asn | Pro | Ile | Ile | Tyr | Pro | Cys | Ser | Ser | Gln | Glu | Phe | Lys | |
| | 320 | | | | | 325 | | | | | 330 | | | | | |
| AAG | GCC | TTT | CAG | AAT | GTC | TTG | AGA | ATC | CAG | TGT | CTC | TGC | AGA | AAG | CAG | 1175 |
| Lys | Ala | Phe | Gln | Asn | Val | Leu | Arg | Ile | Gln | Cys | Leu | Cys | Arg | Lys | Gln | |
| 335 | | | | | 340 | | | | | 345 | | | | | 350 | |
| TCT | TCC | AAA | CAT | GCC | CTG | GGC | TAC | ACC | CTG | CAC | CCG | CCC | AGC | CAG | GCC | 1223 |
| Ser | Ser | Lys | His | Ala | Leu | Gly | Tyr | Thr | Leu | His | Pro | Pro | Ser | Gln | Ala | |
| | | | | 355 | | | | | 360 | | | | | 365 | | |
| GTG | GAA | GGG | CAA | CAC | AAG | GAC | ATG | GTG | CGC | ATC | CCC | GTG | GGA | TCA | AGA | 1271 |
| Val | Glu | Gly | Gln | His | Lys | Asp | Met | Val | Arg | Ile | Pro | Val | Gly | Ser | Arg | |
| | | | 370 | | | | | 375 | | | | | 380 | | | |

```
GAG ACC TTC TAC AGG ATC TCC AAG ACG GAT GGC GTT TGT GAA TGG AAA    1319
Glu Thr Phe Tyr Arg Ile Ser Lys Thr Asp Gly Val Cys Glu Trp Lys
        385                 390                 395

TTT TTC TCT TCC ATG CCC CGT GGA TCT GCC AGG ATT ACA GTG TCC AAA    1367
Phe Phe Ser Ser Met Pro Arg Gly Ser Ala Arg Ile Thr Val Ser Lys
400                 405                 410

GAC CAA TCC TCC TGT ACC ACA GCC CGG GTG AGA AGT AAA AGC TTT TTG    1415
Asp Gln Ser Ser Cys Thr Thr Ala Arg Val Arg Ser Lys Ser Phe Leu
415                 420                 425                 430

CAG GTC TGC TGC TGT GTA GGG CCC TCA ACC CCC AGC CTT GAC AAG AAC    1463
Gln Val Cys Cys Cys Val Gly Pro Ser Thr Pro Ser Leu Asp Lys Asn
                435                 440                 445

CAT CAA GTT CCA ACC ATT AAG GTC CAC ACC ATC TCC CTC AGT GAG AAC    1511
His Gln Val Pro Thr Ile Lys Val His Thr Ile Ser Leu Ser Glu Asn
            450                 455                 460

GGG GAG GAA GTC TAGGACAGGA AAGATGCAGA GGAAAGGGGA ATATCTTAGG        1563
Gly Glu Glu Val
            465

TACCATACCC TGGAGTTCTA GAGGATTCCT CGACAAGCTT ATTCCGATCC AGACATGATA  1623

GATACATTGA TGAGTT                                                  1639
```

( 2 ) INFORMATION FOR SEQ ID NO:6:

( i ) SEQUENCE CHARACTERISTICS:
        ( A ) LENGTH: 466 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Val Phe Leu Ser Gly Asn Ala Ser Asp Ser Ser Asn Cys Thr Gln
1               5                   10                  15

Pro Pro Ala Pro Val Asn Ile Ser Lys Ala Ile Leu Leu Gly Val Ile
            20                  25                  30

Leu Gly Gly Leu Ile Leu Phe Gly Val Leu Gly Asn Ile Leu Val Ile
        35                  40                  45

Leu Ser Val Ala Cys His Arg His Leu His Ser Val Thr His Tyr Tyr
    50                  55                  60

Ile Val Asn Leu Ala Val Ala Asp Leu Leu Leu Thr Ser Thr Val Leu
65                  70                  75                  80

Pro Phe Ser Ala Ile Phe Glu Val Leu Gly Tyr Trp Ala Phe Gly Arg
                85                  90                  95

Val Phe Cys Asn Ile Trp Ala Ala Val Asp Val Leu Cys Cys Thr Ala
            100                 105                 110

Ser Ile Met Gly Leu Cys Ile Ile Ser Ile Asp Arg Tyr Ile Gly Val
        115                 120                 125

Ser Tyr Pro Leu Arg Tyr Pro Thr Ile Val Thr Gln Arg Arg Gly Leu
    130                 135                 140

Met Ala Leu Leu Cys Val Trp Ala Leu Ser Leu Val Ile Ser Ile Gly
145                 150                 155                 160

Pro Leu Phe Gly Trp Arg Gln Pro Ala Pro Glu Asp Glu Thr Ile Cys
                165                 170                 175

Gln Ile Asn Glu Glu Pro Gly Tyr Val Leu Phe Ser Ala Leu Gly Ser
            180                 185                 190

Phe Tyr Leu Pro Leu Ala Ile Ile Leu Val Met Tyr Cys Arg Val Tyr
        195                 200                 205
```

```
Val  Val  Ala  Lys  Arg  Glu  Ser  Arg  Gly  Leu  Lys  Ser  Gly  Leu  Lys  Thr
     210                     215                    220

Asp  Lys  Ser  Asp  Ser  Glu  Gln  Val  Thr  Leu  Arg  Ile  His  Arg  Lys  Asn
225                      230                    235                         240

Ala  Pro  Ala  Gly  Gly  Ser  Gly  Met  Ala  Ser  Ala  Lys  Thr  Lys  Thr  His
               245                      250                         255

Phe  Ser  Val  Arg  Leu  Leu  Lys  Phe  Ser  Arg  Glu  Lys  Lys  Ala  Ala  Lys
               260                      265                    270

Thr  Leu  Gly  Ile  Val  Val  Gly  Cys  Phe  Val  Leu  Cys  Trp  Leu  Pro  Phe
          275                      280                    285

Phe  Leu  Val  Met  Pro  Ile  Gly  Ser  Phe  Phe  Pro  Asp  Phe  Lys  Pro  Ser
     290                      295                    300

Glu  Thr  Val  Phe  Lys  Ile  Val  Phe  Trp  Leu  Gly  Tyr  Leu  Asn  Ser  Cys
305                      310                    315                         320

Ile  Asn  Pro  Ile  Ile  Tyr  Pro  Cys  Ser  Ser  Gln  Glu  Phe  Lys  Lys  Ala
               325                      330                    335

Phe  Gln  Asn  Val  Leu  Arg  Ile  Gln  Cys  Leu  Cys  Arg  Lys  Gln  Ser  Ser
               340                      345                    350

Lys  His  Ala  Leu  Gly  Tyr  Thr  Leu  His  Pro  Pro  Ser  Gln  Ala  Val  Glu
          355                      360                    365

Gly  Gln  His  Lys  Asp  Met  Val  Arg  Ile  Pro  Val  Gly  Ser  Arg  Glu  Thr
     370                      375                    380

Phe  Tyr  Arg  Ile  Ser  Lys  Thr  Asp  Gly  Val  Cys  Glu  Trp  Lys  Phe  Phe
385                      390                    395                         400

Ser  Ser  Met  Pro  Arg  Gly  Ser  Ala  Arg  Ile  Thr  Val  Ser  Lys  Asp  Gln
               405                      410                    415

Ser  Ser  Cys  Thr  Thr  Ala  Arg  Val  Arg  Ser  Lys  Ser  Phe  Leu  Gln  Val
               420                      425                    430

Cys  Cys  Cys  Val  Gly  Pro  Ser  Thr  Pro  Ser  Leu  Asp  Lys  Asn  His  Gln
               435                      440                    445

Val  Pro  Thr  Ile  Lys  Val  His  Thr  Ile  Ser  Leu  Ser  Glu  Asn  Gly  Glu
     450                      455                    460

Glu  Val
465
```

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CACTCAAGTA CCCAGCCATC ATGAC 25

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CGGAGAGCGA GCTGCGGAAG GTGTG 25

( 2 ) INFORMATION FOR SEQ ID NO:9:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GCAAGGCCTC CGAGGTGGTG CTGCGCATCC ACTGTCGCGG CGCGG     45

( 2 ) INFORMATION FOR SEQ ID NO:10:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

TGCCGTGCGC CCCGTCGGCG CCCGTGGCCG CGCCGCGACA GTGGATG     47

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CAACGATGAC AAGGAGTGCG GGGTCAC     27

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

TTTGACAGCT ATGGAACTCC TGGGG     25

( 2 ) INFORMATION FOR SEQ ID NO:13:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

AAGGAGCTGA CCCTGAGGAT CCATTCCAAG AACTTTCACG AGGAC     45

( 2 ) INFORMATION FOR SEQ ID NO:14:

( i ) SEQUENCE CHARACTERISTICS:

( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CCTTGGCCTT GGTACTGCTA AGGGTGTCCT CGTGAAAGTT CTTGG 45

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CCAACCATCG TCACCCAGAG GAG 23

( 2 ) INFORMATION FOR SEQ ID NO:16:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

TCTCCCGGGA GAACTTGAGG AGCCTCAC 28

( 2 ) INFORMATION FOR SEQ ID NO:17:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

TCCGCATCCA TCGGAAAAAC GCCCCGGCAG GAGGCAGCGG GATGG 45

( 2 ) INFORMATION FOR SEQ ID NO:18:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

GAAGTGCGTC TTGGTCTTGG CGCTGGCCAT CCCGCTGCCT CCTGCC 46

( 2 ) INFORMATION FOR SEQ ID NO:19:

( i ) SEQUENCE CHARACTERISTICS:
        ( A ) LENGTH: 521 amino acids
        ( B ) TYPE: amino acid
        ( C ) STRANDEDNESS: single
        ( D ) TOPOLOGY: linear (i i) MOLECULE TYPE: protein (x i) SEQUENCE DESCRIPTION: SEQ ID NO:19:

| Met | Ala | Ala | Ala | Leu | Arg | Ser | Val | Met | Met | Ala | Gly | Tyr | Leu | Ser | Glu |
|---|---|---|---|---|---|---|---|---|---|---|---|---|---|---|---|
| 1 | | | | 5 | | | | | 10 | | | | | 15 | |
| Trp | Arg | Thr | Pro | Thr | Tyr | Arg | Ser | Thr | Glu | Met | Val | Gln | Arg | Leu | Arg |
| | | | 20 | | | | 25 | | | | | 30 | | | |
| Met | Glu | Ala | Val | Gln | His | Ser | Thr | Ser | Thr | Ala | Ala | Val | Gly | Gly | Leu |
| | | 35 | | | | | 40 | | | | | 45 | | | |
| Val | Val | Ser | Ala | Gln | Gly | Val | Gly | Val | Gly | Val | Phe | Leu | Ala | Ala | Phe |
| | 50 | | | | | 55 | | | | | 60 | | | | |
| Ile | Leu | Thr | Ala | Val | Ala | Gly | Asn | Leu | Leu | Val | Ile | Leu | Ser | Val | Ala |
| 65 | | | | | 70 | | | | | 75 | | | | | 80 |
| Cys | Asn | Arg | His | Leu | Gln | Thr | Val | Thr | Asn | Tyr | Phe | Ile | Val | Asn | Leu |
| | | | | 85 | | | | | 90 | | | | | 95 | |
| Ala | Val | Ala | Asp | Leu | Leu | Leu | Ser | Ala | Ala | Val | Leu | Pro | Phe | Ser | Ala |
| | | | 100 | | | | | 105 | | | | | 110 | | |
| Thr | Met | Glu | Val | Leu | Gly | Phe | Trp | Ala | Phe | Gly | Arg | Thr | Phe | Cys | Asp |
| | | 115 | | | | | 120 | | | | | 125 | | | |
| Val | Trp | Ala | Ala | Val | Asp | Val | Leu | Cys | Cys | Thr | Ala | Ser | Ile | Leu | Ser |
| | 130 | | | | | 135 | | | | | 140 | | | | |
| Leu | Cys | Thr | Ile | Ser | Val | Asp | Arg | Tyr | Val | Gly | Val | Arg | His | Ser | Leu |
| 145 | | | | | 150 | | | | | 155 | | | | | 160 |
| Lys | Tyr | Pro | Ala | Ile | Met | Thr | Glu | Arg | Lys | Ala | Ala | Ala | Ile | Leu | Ala |
| | | | | 165 | | | | | 170 | | | | | 175 | |
| Leu | Leu | Trp | Ala | Val | Ala | Leu | Val | Val | Ser | Val | Gly | Pro | Leu | Leu | Gly |
| | | | 180 | | | | | 185 | | | | | 190 | | |
| Trp | Lys | Glu | Pro | Val | Pro | Pro | Asp | Glu | Arg | Phe | Cys | Gly | Ile | Thr | Glu |
| | | 195 | | | | | 200 | | | | | 205 | | | |
| Glu | Val | Gly | Tyr | Ala | Ile | Phe | Ser | Ser | Val | Cys | Ser | Phe | Tyr | Leu | Pro |
| | 210 | | | | | 215 | | | | | 220 | | | | |
| Met | Ala | Val | Ile | Val | Val | Met | Tyr | Cys | Arg | Val | Tyr | Val | Val | Ala | Arg |
| 225 | | | | | 230 | | | | | 235 | | | | | 240 |
| Ser | Thr | Thr | Arg | Ser | Leu | Glu | Ala | Gly | Ile | Lys | Arg | Glu | Pro | Gly | Lys |
| | | | | 245 | | | | | 250 | | | | | 255 | |
| Ala | Ser | Glu | Val | Val | Leu | Arg | Ile | His | Cys | Arg | Gly | Ala | Ala | Thr | Ser |
| | | | 260 | | | | | 265 | | | | | 270 | | |
| Ala | Asp | Gly | Ala | His | Gly | Met | Arg | Ser | Ala | Lys | Gly | His | Thr | Phe | Arg |
| | | 275 | | | | | 280 | | | | | 285 | | | |
| Ser | Ser | Leu | Ser | Val | Arg | Leu | Leu | Lys | Phe | Ser | Arg | Glu | Lys | Lys | Ala |
| | 290 | | | | | 295 | | | | | 300 | | | | |
| Ala | Lys | Thr | Leu | Ala | Ile | Val | Val | Gly | Val | Phe | Val | Leu | Cys | Trp | Phe |
| 305 | | | | | 310 | | | | | 315 | | | | | 320 |
| Pro | Phe | Phe | Phe | Val | Leu | Pro | Leu | Gly | Ser | Leu | Phe | Pro | Gln | Leu | Lys |
| | | | | 325 | | | | | 330 | | | | | 335 | |
| Pro | Ser | Glu | Gly | Val | Phe | Lys | Val | Ile | Phe | Trp | Leu | Gly | Tyr | Phe | Asn |
| | | | 340 | | | | | 345 | | | | | 350 | | |
| Ser | Cys | Val | Asn | Pro | Leu | Ile | Tyr | Pro | Cys | Ser | Ser | Arg | Glu | Phe | Lys |
| | | 355 | | | | | 360 | | | | | 365 | | | |
| Arg | Ala | Phe | Leu | Arg | Leu | Leu | Arg | Cys | Gln | Cys | Arg | Arg | Arg | Arg | Arg |
| | 370 | | | | | 375 | | | | | 380 | | | | |
| Arg | Arg | Pro | Leu | Trp | Arg | Val | Tyr | Gly | His | His | Trp | Arg | Ala | Ser | Thr |
| 385 | | | | | 390 | | | | | 395 | | | | | 400 |
| Ser | Gly | Leu | Arg | Gln | Asp | Cys | Ala | Pro | Ser | Ser | Gly | Asp | Ala | Pro | Pro |

|     |     |     |     | 405 |     |     |     | 410 |     |     |     | 415 |     |     |
|-----|-----|-----|-----|-----|-----|-----|-----|-----|-----|-----|-----|-----|-----|-----|
| Gly | Ala | Pro | Ala<br>420 | Leu | Thr | Ala | Leu | Pro<br>425 | Asp | Pro | Asp | Pro<br>430 | Glu | Pro | Pro |
| Gly | Thr | Pro<br>435 | Glu | Met | Gln | Ala | Pro<br>440 | Val | Ala | Ser | Arg | Arg<br>445 | Ser | His | Pro |
| Ala | Pro | Ser<br>450 | Ala | Ser | Gly | Gly<br>455 | Cys | Gln | Gly | Arg | Ser<br>460 | Gly | Asp | Pro | Arg |
| Pro<br>465 | Ser | Cys | Ala | Pro | Lys<br>470 | Ser | Pro | Ala | Cys | Arg<br>475 | Thr | Arg | Ser | Pro | Pro<br>480 |
| Gly | Ala | Arg | Ser | Ala<br>485 | Gln | Arg | Gln | Arg | Ala<br>490 | Pro | Ser | Ala | Gln | Arg<br>495 | Trp |
| Arg | Leu | Cys | Pro<br>500 | Ser | Leu | Val | Pro | Ala<br>505 | Glu | Cys | Gln | Ala | Tyr<br>510 | Glu | Asp |
| Tyr | Ser | Asn<br>515 | Leu | Arg | Glu | Thr | Asp<br>520 | Ile |     |     |     |     |     |     |     |

( 2 ) INFORMATION FOR SEQ ID NO:20:

( i ) SEQUENCE CHARACTERISTICS:
        ( A ) LENGTH: 559 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:20:

| Met<br>1 | Thr | Phe | Arg | Asp<br>5 | Ile | Leu | Ser | Val | Thr<br>10 | Phe | Glu | Gly | Pro | Arg<br>15 | Ser |
|---|---|---|---|---|---|---|---|---|---|---|---|---|---|---|---|
| Ser | Ser | Ser | Thr<br>20 | Gly | Gly | Ser | Gly | Ala<br>25 | Gly | Gly | Gly | Ala | Gly<br>30 | Thr | Val |
| Gly | Pro | Glu<br>35 | Gly | Gly | Ala | Val | Gly<br>40 | Gly | Val | Pro | Gly | Ala<br>45 | Thr | Gly | Gly |
| Gly | Ala<br>50 | Val | Val | Gly | Thr | Gly<br>55 | Ser | Gly | Glu | Asp | Asn<br>60 | Gln | Ser | Ser | Thr |
| Gly<br>65 | Glu | Pro | Gly | Ala | Ala<br>70 | Ala | Ser | Gly | Glu | Val<br>75 | Asn | Gly | Ser | Ala | Ala<br>80 |
| Val | Gly | Gly | Leu | Val<br>85 | Val | Ser | Ala | Gln | Gly<br>90 | Val | Gly | Val | Gly | Val<br>95 | Phe |
| Leu | Ala | Ala | Phe<br>100 | Ile | Leu | Thr | Ala | Val<br>105 | Ala | Gly | Asn | Leu | Leu<br>110 | Val | Ile |
| Leu | Ser | Val<br>115 | Ala | Cys | Asn | Arg | His<br>120 | Leu | Gln | Thr | Val | Thr<br>125 | Asn | Tyr | Phe |
| Ile | Val<br>130 | Asn | Leu | Ala | Val | Ala<br>135 | Asp | Leu | Leu | Leu | Ser<br>140 | Ala | Ala | Val | Leu |
| Pro<br>145 | Phe | Ser | Ala | Thr | Met<br>150 | Glu | Val | Leu | Gly | Phe<br>155 | Trp | Ala | Phe | Gly | Arg<br>160 |
| Thr | Phe | Cys | Asp | Val<br>165 | Trp | Ala | Ala | Val | Asp<br>170 | Val | Leu | Cys | Cys | Thr<br>175 | Ala |
| Ser | Ile | Leu | Ser | Leu<br>180 | Cys | Thr | Ile | Ser | Val<br>185 | Asp | Arg | Tyr | Val | Gly<br>190 | Val |
| Arg | His | Ser<br>195 | Leu | Lys | Tyr | Pro | Ala<br>200 | Ile | Met | Thr | Glu | Arg<br>205 | Lys | Ala | Ala |
| Ala | Ile<br>210 | Leu | Ala | Leu | Leu | Trp<br>215 | Ala | Val | Ala | Leu | Val<br>220 | Val | Ser | Val | Gly |
| Pro<br>225 | Leu | Leu | Gly | Trp | Lys<br>230 | Glu | Pro | Val | Pro | Pro<br>235 | Asp | Glu | Arg | Phe | Cys<br>240 |

| | | | | | | | | | | | | | | | |
|---|---|---|---|---|---|---|---|---|---|---|---|---|---|---|---|
|Gly|Ile|Thr|Glu|Glu|Val|Gly|Tyr|Ala|Ile|Phe|Ser|Ser|Val|Cys|Ser|
| | | |245| | | | |250| | | | |255| | |
|Phe|Tyr|Leu|Pro|Met|Ala|Val|Ile|Val|Val|Met|Tyr|Cys|Arg|Val|Tyr|
| | | |260| | | |265| | | | |270| | | |
|Val|Val|Ala|Arg|Ser|Thr|Thr|Arg|Ser|Leu|Glu|Ala|Gly|Ile|Lys|Arg|
| | |275| | | |280| | | |285| | | | | |
|Glu|Pro|Gly|Lys|Ala|Ser|Val|Leu|Arg|Ile|His|Cys|Arg|Gly|Ala| |
| |290| | | | |295| | | |300| | | | | |
|Thr|Thr|Ser|Ala|Lys|Gly|Tyr|Pro|Gly|Thr|Gln|Ser|Ser|Lys|Gly|His|
|305| | | | |310| | | |315| | | | | |320|
|Thr|Leu|Arg|Ser|Ser|Leu|Ser|Val|Arg|Leu|Leu|Lys|Phe|Ser|Arg|Glu|
| | | |325| | | |330| | | | |335| | | |
|Lys|Lys|Ala|Ala|Lys|Thr|Leu|Ala|Ile|Val|Val|Gly|Val|Phe|Val|Leu|
| | |340| | | |345| | | |350| | | | | |
|Cys|Trp|Phe|Pro|Phe|Phe|Phe|Val|Leu|Pro|Leu|Gly|Ser|Leu|Phe|Pro|
| |355| | | | |360| | | |365| | | | | |
|Gln|Leu|Lys|Pro|Ser|Glu|Gly|Val|Phe|Lys|Val|Ile|Phe|Trp|Leu|Gly|
| |370| | | | |375| | | |380| | | | | |
|Tyr|Phe|Asn|Ser|Cys|Val|Asn|Pro|Leu|Ile|Tyr|Pro|Cys|Ser|Ser|Arg|
|385| | | | |390| | | |395| | | | | |400|
|Glu|Phe|Lys|Arg|Ala|Phe|Leu|Arg|Leu|Leu|Arg|Cys|Gln|Cys|Arg|Arg|
| | | |405| | | | |410| | | | |415| | |
|Arg|Arg|Arg|Arg|Leu|Trp|Ser|Leu|Arg|Pro|Pro|Leu|Ala|Ser|Leu|Asp|
| | | |420| | | |425| | | | |430| | | |
|Arg|Arg|Arg|Ala|Phe|Arg|Leu|Arg|Pro|Gln|Pro|Ser|His|Arg|Ser|Pro|
| | |435| | | |440| | | |445| | | | | |
|Arg|Gly|Pro|Ser|Ser|Pro|His|Cys|Thr|Pro|Gly|Cys|Gly|Leu|Gly|Arg|
| |450| | | |455| | | |460| | | | | | |
|His|Ala|Gly|Asp|Ala|Gly|Phe|Gly|Leu|Gln|Gln|Ser|Lys|Ala|Ser|Leu|
|465| | | |470| | | |475| | | | | | |480|
|Arg|Leu|Arg|Glu|Trp|Arg|Leu|Leu|Gly|Pro|Leu|Gln|Arg|Pro|Thr|Thr|
| | | |485| | | |490| | | | |495| | | |
|Gln|Leu|Arg|Ala|Lys|Val|Ser|Ser|Leu|Ser|His|Lys|Ile|Arg|Ser|Gly|
| | |500| | | |505| | | |510| | | | | |
|Ala|Arg|Arg|Ala|Glu|Thr|Ala|Cys|Ala|Leu|Arg|Ser|Glu|Val|Glu|Ala|
| | |515| | | |520| | | |525| | | | | |
|Val|Ser|Leu|Asn|Val|Pro|Gln|Asp|Gly|Ala|Glu|Ala|Val|Ile|Cys|Gln|
| |530| | | |535| | | |540| | | | | | |
|Ala|Tyr|Glu|Pro|Gly|Asp|Tyr|Ser|Asn|Leu|Arg|Glu|Thr|Asp|Ile| |
|545| | | |550| | | |555| | | | | | | |

( 2 ) INFORMATION FOR SEQ ID NO:21:

( i ) SEQUENCE CHARACTERISTICS:
        ( A ) LENGTH: 513 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:21:

| | | | | | | | | | | | | | | | |
|---|---|---|---|---|---|---|---|---|---|---|---|---|---|---|---|
|Met|Asn|Pro|Asp|Leu|Asp|Thr|Gly|His|Asn|Thr|Ser|Ala|Pro|Ala|His|
|1| | | |5| | | |10| | | |15| | | |
|Trp|Gly|Glu|Leu|Lys|Asp|Asp|Asn|Phe|Thr|Gly|Pro|Asn|Gln|Thr|Ser|
| | | |20| | | |25| | | | |30| | | |

| | | | | | | | | | | | | | |
|---|---|---|---|---|---|---|---|---|---|---|---|---|---|
| Ser | Asn | Ser 35 | Thr | Leu | Pro | Gln 40 | Leu | Asp | Val | Thr | Arg 45 | Ala | Ile | Ser | Val |
| Gly | Leu 50 | Val | Leu | Gly | Ala | Phe 55 | Ile | Leu | Phe | Ala | Ile 60 | Val | Gly | Asn | Ile |
| Leu 65 | Val | Ile | Leu | Ser | Val 70 | Ala | Cys | Asn | Arg | His 75 | Leu | Arg | Thr | Pro | Thr 80 |
| Asn | Tyr | Phe | Ile | Val 85 | Asn | Leu | Ala | Ile | Ala 90 | Asp | Leu | Leu | Leu | Ser 95 | Phe |
| Thr | Val | Leu | Pro 100 | Phe | Ser | Ala | Thr | Leu 105 | Glu | Val | Leu | Gly | Tyr 110 | Trp | Val |
| Leu | Gly | Arg 115 | Ile | Phe | Cys | Asp | Ile 120 | Trp | Ala | Ala | Val | Asp 125 | Val | Leu | Cys |
| Cys | Thr 130 | Ala | Ser | Ile | Leu | Ser 135 | Leu | Cys | Ala | Ile | Ser 140 | Ile | Asp | Arg | Tyr |
| Ile 145 | Gly | Val | Arg | Tyr | Ser 150 | Leu | Gln | Tyr | Pro | Thr 155 | Leu | Val | Thr | Arg | Arg 160 |
| Lys | Ala | Ile | Leu | Ala 165 | Leu | Leu | Ser | Val | Trp 170 | Val | Leu | Ser | Thr | Val 175 | Ile |
| Ser | Ile | Gly | Pro 180 | Leu | Leu | Gly | Trp | Lys 185 | Glu | Pro | Ala | Pro | Asn 190 | Asp | Asp |
| Lys | Glu | Cys 195 | Gly | Val | Thr | Glu | Glu 200 | Pro | Phe | Cys | Ala | Leu 205 | Phe | Cys | Ser |
| Leu | Gly 210 | Ser | Phe | Tyr | Ile | Pro 215 | Leu | Ala | Val | Ile | Leu 220 | Val | Met | Tyr | Cys |
| Arg 225 | Val | Tyr | Ile | Val | Ala 230 | Lys | Arg | Thr | Thr | Lys 235 | Asn | Leu | Glu | Ala | Gly 240 |
| Val | Met | Lys | Glu | Met 245 | Ser | Asn | Ser | Lys | Glu 250 | Leu | Thr | Leu | Thr | Ile 255 | His |
| Ser | Lys | Asn | Phe 260 | His | Glu | Asp | Thr | Leu 265 | Ser | Ser | Thr | Lys | Ala 270 | Lys | Gly |
| His | Asn | Pro 275 | Arg | Ser | Ser | Ile | Ala 280 | Val | Lys | Leu | Phe | Lys 285 | Phe | Ser | Arg |
| Glu | Lys 290 | Lys | Ala | Ala | Lys | Thr 295 | Leu | Gly | Ile | Val | Val 300 | Gly | Met | Phe | Ile |
| Leu 305 | Cys | Trp | Leu | Pro | Phe 310 | Phe | Ile | Ala | Leu | Pro 315 | Leu | Gly | Ser | Leu | Phe 320 |
| Ser | Thr | Leu | Lys | Pro 325 | Pro | Asp | Ala | Val | Phe 330 | Lys | Val | Val | Phe | Trp 335 | Leu |
| Gly | Tyr | Phe | Asn 340 | Ser | Cys | Leu | Asn | Pro 345 | Ile | Ile | Tyr | Pro | Cys 350 | Ser | Ser |
| Lys | Glu | Phe 355 | Lys | Arg | Ala | Phe | Met 360 | Arg | Ile | Leu | Gly | Cys 365 | Gln | Cys | Arg |
| Arg | Arg 370 | Arg | Arg | Arg | Arg | Arg 375 | Arg | Leu | Gly | Ala | Cys 380 | Ala | Tyr | Thr | Tyr |
| Arg 385 | Pro | Trp | Thr | Arg | Gly 390 | Gly | Ser | Leu | Glu | Arg 395 | Ser | Gln | Ser | Arg | Lys 400 |
| Asp | Ser | Leu | Asp | Asp 405 | Ser | Gly | Ser | Cys | Met 410 | Ser | Gly | Gln | Lys | Arg 415 | Thr |
| Leu | Pro | Ser | Ala 420 | Ser | Pro | Ser | Pro | Gly 425 | Tyr | Leu | Gly | Arg | Gly 430 | Thr | Gln |
| Pro | Pro | Val 435 | Glu | Leu | Cys | Ala | Phe 440 | Pro | Glu | Trp | Lys | Pro 445 | Gly | Ala | Leu |
| Leu | Ser 450 | Leu | Pro | Glu | Pro | Pro 455 | Gly | Arg | Arg | Gly | Arg 460 | Leu | Asp | Ser | Gly |

```
Pro  Leu  Phe  Thr  Phe  Lys  Leu  Leu  Gly  Asp  Pro  Glu  Ser  Pro  Gly  Thr
465                 470                      475                           480

Glu  Ala  Thr  Ala  Ser  Asn  Gly  Gly  Cys  Asp  Thr  Thr  Thr  Asp  Leu  Ala
                    485                      490                      495

Asn  Gly  Gln  Pro  Gly  Phe  Lys  Ser  Asn  Met  Pro  Leu  Gly  Pro  Gly  His
               500                      505                      510

Phe
```

(2) INFORMATION FOR SEQ ID NO:22:

(i) SEQUENCE CHARACTERISTICS:
      (A) LENGTH: 515 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:22:

```
Met  Asn  Pro  Asp  Leu  Asp  Thr  Gly  His  Asn  Thr  Ser  Ala  Pro  Ala  Gln
1                   5                        10                      15

Trp  Gly  Glu  Leu  Lys  Asp  Ala  Asn  Phe  Thr  Gly  Pro  Asn  Gln  Thr  Ser
               20                       25                      30

Ser  Asn  Ser  Thr  Leu  Pro  Gln  Leu  Asp  Val  Thr  Arg  Ala  Ile  Ser  Val
          35                       40                      45

Gly  Leu  Val  Leu  Gly  Ala  Phe  Ile  Leu  Phe  Ala  Ile  Val  Gly  Asn  Ile
     50                       55                      60

Leu  Val  Ile  Leu  Ser  Val  Ala  Cys  Asn  Arg  His  Leu  Arg  Thr  Pro  Thr
65                       70                      75                           80

Asn  Tyr  Phe  Ile  Val  Asn  Leu  Ala  Ile  Ala  Asp  Leu  Leu  Leu  Ser  Phe
                    85                       90                      95

Thr  Val  Leu  Pro  Phe  Ser  Ala  Thr  Leu  Glu  Val  Leu  Gly  Tyr  Trp  Val
               100                      105                     110

Leu  Gly  Arg  Ile  Phe  Cys  Asp  Ile  Trp  Ala  Ala  Val  Asp  Val  Leu  Cys
          115                      120                     125

Cys  Thr  Ala  Ser  Ile  Leu  Ser  Leu  Cys  Ala  Ile  Ser  Ile  Asp  Arg  Tyr
     130                      135                     140

Ile  Gly  Val  Arg  Tyr  Ser  Leu  Gln  Tyr  Pro  Thr  Leu  Val  Thr  Arg  Arg
145                      150                     155                          160

Lys  Ala  Ile  Leu  Ala  Leu  Leu  Ser  Val  Trp  Val  Leu  Ser  Thr  Val  Ile
                    165                      170                     175

Ser  Ile  Gly  Pro  Leu  Leu  Gly  Trp  Lys  Glu  Pro  Ala  Pro  Asn  Asp  Asp
               180                      185                     190

Lys  Glu  Cys  Gly  Val  Thr  Glu  Glu  Pro  Phe  Tyr  Ala  Leu  Phe  Ser  Ser
          195                      200                     205

Leu  Gly  Ser  Phe  Tyr  Ile  Pro  Leu  Ala  Val  Ile  Leu  Val  Met  Tyr  Cys
     210                      215                     220

Arg  Val  Tyr  Ile  Val  Ala  Lys  Arg  Thr  Thr  Lys  Asn  Leu  Glu  Ala  Gly
225                      230                     235                          240

Val  Met  Lys  Glu  Met  Ser  Asn  Ser  Lys  Glu  Leu  Thr  Leu  Arg  Ile  His
                    245                      250                     255

Ser  Lys  Asn  Phe  His  Glu  Asp  Thr  Leu  Ser  Ser  Thr  Lys  Ala  Lys  Gly
               260                      265                     270

His  Asn  Pro  Arg  Ser  Ser  Ile  Ala  Val  Lys  Leu  Phe  Lys  Phe  Ser  Arg
          275                      280                     285

Glu  Lys  Lys  Ala  Ala  Lys  Thr  Leu  Gly  Ile  Val  Val  Gly  Met  Phe  Ile
```

-continued

|   |   |   |   | 290 |   |   |   | 295 |   |   |   | 300 |   |   |   |
|---|---|---|---|---|---|---|---|---|---|---|---|---|---|---|---|
| Leu 305 | Cys | Trp | Leu | Pro 310 | Phe | Ile | Ala | Leu 315 | Pro | Leu | Gly | Ser | Leu | Phe 320 |   |
| Ser | Thr | Leu | Lys | Pro 325 | Pro | Asp | Ala | Val 330 | Phe | Lys | Val | Val | Phe | Trp 335 | Leu |
| Gly | Tyr | Phe | Asn 340 | Ser | Cys | Leu | Asn | Pro 345 | Ile | Ile | Tyr | Pro | Cys 350 | Ser | Ser |
| Lys | Glu | Phe 355 | Lys | Arg | Ala | Phe | Met 360 | Arg | Ile | Leu | Gly | Cys 365 | Gln | Cys | Arg |
| Ser | Gly 370 | Arg | Arg | Arg | Arg | Arg 375 | Arg | Arg | Leu | Gly 380 | Ala | Cys | Ala | Tyr |   |
| Thr 385 | Tyr | Arg | Pro | Trp | Thr 390 | Arg | Gly | Gly | Ser | Leu 395 | Glu | Arg | Ser | Gln | Ser 400 |
| Arg | Lys | Asp | Ser | Leu 405 | Asp | Asp | Ser | Gly | Ser 410 | Cys | Met | Ser | Gly | Ser 415 | Gln |
| Arg | Thr | Leu | Pro 420 | Ser | Ala | Ser | Pro | Ser 425 | Pro | Gly | Tyr | Leu | Gly 430 | Arg | Gly |
| Ala | Gln | Pro 435 | Pro | Leu | Glu | Leu | Cys 440 | Ala | Tyr | Pro | Glu | Trp 445 | Lys | Ser | Gly |
| Ala | Leu 450 | Leu | Ser | Leu | Pro | Glu 455 | Pro | Pro | Gly | Arg 460 | Arg | Gly | Arg | Leu | Asp |
| Ser 465 | Gly | Pro | Leu | Phe | Thr 470 | Phe | Lys | Leu | Leu | Gly 475 | Glu | Pro | Glu | Ser | Pro 480 |
| Gly | Thr | Glu | Gly | Asp 485 | Ala | Ser | Asn | Gly | Gly 490 | Cys | Asp | Ala | Thr | Thr 495 | Asp |
| Leu | Ala | Asn | Gly 500 | Gln | Pro | Gly | Phe | Lys 505 | Ser | Asn | Met | Pro | Leu 510 | Ala | Pro |
| Gly | His | Phe 515 |   |   |   |   |   |   |   |   |   |   |   |   |   |

( 2 ) INFORMATION FOR SEQ ID NO:23:

( i ) SEQUENCE CHARACTERISTICS:
        ( A ) LENGTH: 466 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:23:

| Met 1 | Val | Phe | Leu | Ser 5 | Gly | Asn | Ala | Ser | Asp 10 | Ser | Ser | Asn | Cys | Thr 15 | His |
|---|---|---|---|---|---|---|---|---|---|---|---|---|---|---|---|
| Pro | Pro | Pro | Pro 20 | Val | Asn | Ile | Ser | Lys 25 | Ala | Ile | Leu | Leu | Gly 30 | Val | Ile |
| Leu | Gly | Gly 35 | Leu | Glu | Leu | Phe | Gly 40 | Val | Leu | Gly | Asn | Ile 45 | Leu | Val | Ile |
| Leu | Ser 50 | Val | Ala | Cys | His | Arg 55 | His | Leu | His | Ser | Val 60 | Thr | His | Tyr | Tyr |
| Ile 65 | Val | Asn | Leu | Ala | Val 70 | Ala | Asp | Leu | Leu | Leu 75 | Thr | Ser | Thr | Val | Leu 80 |
| Pro | Phe | Ser | Ala | Ile 85 | Phe | Glu | Ile | Leu | Gly 90 | Tyr | Trp | Ala | Phe | Gly 95 | Arg |
| Val | Phe | Cys | Asn 100 | Val | Trp | Ala | Ala | Val 105 | Asp | Val | Leu | Cys | Cys 110 | Thr | Ala |
| Ser | Ile | Met 115 | Gly | Leu | Cys | Ile | Ile 120 | Ser | Ile | Asp | Arg | Tyr 125 | Ile | Gly | Val |

-continued

| | | | | | | | | | | | | | | |
|---|---|---|---|---|---|---|---|---|---|---|---|---|---|---|
| Ser | Tyr 130 | Pro | Leu | Arg | Tyr 135 | Pro | Thr | Ile | Val | Thr 140 | Gln | Lys | Arg | Gly | Leu |
| Met 145 | Ala | Leu | Leu | Cys | Val 150 | Trp | Ala | Leu | Ser | Val 155 | Leu | Ile | Ser | Ile | Gly 160 |
| Pro | Leu | Phe | Gly | Trp 165 | Arg | Gln | Pro | Ala | Pro 170 | Glu | Asp | Glu | Thr | Ile 175 | Cys |
| Gln | Ile | Asn | Glu 180 | Glu | Pro | Gly | Tyr | Val 185 | Leu | Phe | Ser | Ala | Leu 190 | Gly | Ser |
| Phe | Tyr | Val 195 | Pro | Leu | Thr | Ile | Ile 200 | Leu | Val | Met | Tyr | Cys 205 | Arg | Val | Tyr |
| Val | Val 210 | Ala | Lys | Arg | Glu | Ser 215 | Arg | Gly | Leu | Lys | Ser 220 | Gly | Leu | Lys | Thr |
| Asp 225 | Lys | Ser | Asp | Ser | Glu 230 | Gln | Val | Thr | Leu | Arg 235 | Ile | His | Arg | Lys | Asn 240 |
| Ala | Gln | Val | Gly | Gly 245 | Ser | Gly | Val | Thr | Ser 250 | Ala | Lys | Asn | Lys | Thr 255 | His |
| Phe | Ser | Val | Arg 260 | Leu | Leu | Lys | Phe | Ser 265 | Arg | Glu | Lys | Lys | Ala 270 | Ala | Lys |
| Thr | Leu | Gly 275 | Ile | Val | Val | Gly | Cys 280 | Phe | Val | Leu | Cys | Trp 285 | Leu | Pro | Phe |
| Phe | Leu 290 | Val | Met | Pro | Ile | Gly 295 | Ser | Phe | Phe | Pro | Asp 300 | Phe | Arg | Pro | Ser |
| Glu 305 | Thr | Val | Phe | Lys | Ile 310 | Ala | Phe | Trp | Leu | Gly 315 | Tyr | Leu | Asn | Ser | Cys 320 |
| Ile | Asn | Pro | Ile | Ile 325 | Tyr | Pro | Cys | Ser | Ser 330 | Gln | Glu | Phe | Lys | Lys 335 | Ala |
| Phe | Gln | Asn | Val 340 | Leu | Arg | Ile | Gln | Cys 345 | Leu | Arg | Arg | Lys | Gln 350 | Ser | Ser |
| Lys | His | Thr 355 | Leu | Gly | Tyr | Thr | Leu 360 | His | Ala | Pro | Ser | His 365 | Val | Leu | Glu |
| Gly | Gln 370 | His | Lys | Asp | Leu | Val 375 | Arg | Ile | Pro | Val | Gly 380 | Ser | Ala | Glu | Thr |
| Phe 385 | Tyr | Lys | Ile | Ser | Lys 390 | Thr | Asp | Gly | Val | Cys 395 | Glu | Trp | Lys | Ile | Phe 400 |
| Ser | Ser | Leu | Pro | Arg 405 | Gly | Ser | Ala | Arg | Met 410 | Ala | Val | Ala | Arg | Asp 415 | Pro |
| Ser | Ala | Cys | Thr 420 | Thr | Ala | Arg | Val | Arg 425 | Ser | Lys | Ser | Phe | Leu 430 | Gln | Val |
| Cys | Cys | Cys 435 | Leu | Gly | Pro | Ser | Thr 440 | Pro | Ser | His | Gly | Glu 445 | Asn | His | Gln |
| Ile | Pro 450 | Thr | Ile | Lys | Ile | His 455 | Thr | Ile | Ser | Leu | Ser 460 | Glu | Asn | Gly | Glu |
| Glu 465 | Val | | | | | | | | | | | | | | |

What is claimed:

1. An isolated nucleic acid molecule encoding a human α$_{1a}$ adrenergic receptor, wherein the α$_{1a}$ adrenergic receptor has an amino acid sequence as shown in SEQ ID No. 2.

2. An isolated nucleic acid molecule encoding a human α$_{1b}$ adrenergic receptor, wherein the α$_{1b}$ adrenergic receptor has an amino acid sequence as shown in SEQ ID No. 4.

3. The nucleic acid molecule of claim 1 or 2, wherein the nucleic acid molecule is a DNA molecule.

4. The DNA molecule of claim 3, wherein the DNA molecule is a cDNA molecule.

5. A vector comprising a DNA molecule of claim 3.

6. A plasmid comprising the vector of claim 5.

7. The vector of claim 5 adapted for expression in a bacterial cell which comprises the regulatory elements necessary for expression of the DNA in a bacterial cell so located relative to the DNA encoding a human α$_1$ adrenergic receptor as to permit expression thereof.

8. The vector of claim 5 adapted for expression in a yeast cell which comprises the regulatory elements necessary for the expression of the DNA in a yeast cell so located relative to the DNA encoding a human $\alpha_1$ adrenergic receptor as to permit expression thereof.

9. The vector of claim 5 adapted for expression in a mammalian cell which comprises the regulatory elements necessary for expression of the DNA in the mammalian cell so located relative to the DNA encoding a human $\alpha_1$ adrenergic receptor as to permit expression thereof.

10. The plasmid of claim 6 adapted for expression in a mammalian cell which comprises the regulatory elements necessary for expression of the DNA in the mammalian cell so located relative to the DNA encoding a human $\alpha_1$ adrenergic receptor as to permit expression thereof.

11. A plasmid designated pcEXV-$\alpha_{1a}$.

12. A plasmid designated pcEXV-$\alpha_{1b}$.

13. A mammalian cell comprising the plasmid of claim 6.

14. The mammalian cell of claim 13, wherein the mammalian cell is an LM (tk−) cell.

15. An LM (tk−) cell comprising the plasmid of claim 10.

* * * * *